US010265434B2

(12) United States Patent
Klofta et al.

(10) Patent No.: US 10,265,434 B2
(45) Date of Patent: Apr. 23, 2019

(54) ABSORBENT ARTICLES COMPRISING GLYCERIDE COPOLYMERS

(71) Applicant: The Procter & Gamble Company, Cincinnati, OH (US)

(72) Inventors: Thomas James Klofta, Cincinnati, OH (US); Randall Glenn Marsh, Hamilton, OH (US); Victor Nicholas Vega, Cincinnati, OH (US); Philip Andrew Sawin, Cincinnati, OH (US); Beth Ann Schubert, Maineville, OH (US); Luke Andrew Zannoni, West Chester, OH (US); Joseph Jay Kemper, Cincinnati, OH (US); Robert John Strife, West Chester, OH (US); Jeffrey John Scheibel, Glendale, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 45 days.

(21) Appl. No.: 15/713,762

(22) Filed: Sep. 25, 2017

(65) Prior Publication Data
US 2018/0161474 A1   Jun. 14, 2018

Related U.S. Application Data

(60) Provisional application No. 62/401,474, filed on Sep. 29, 2016.

(51) Int. Cl.
| | |
|---|---|
| *A61L 15/46* | (2006.01) |
| *A61L 15/26* | (2006.01) |
| *C08G 63/06* | (2006.01) |
| *A61L 15/60* | (2006.01) |
| *A61L 15/40* | (2006.01) |

(Continued)

(52) U.S. Cl.
CPC .............. *A61L 15/26* (2013.01); *A61F 13/47* (2013.01); *A61F 13/496* (2013.01); *A61F 13/51113* (2013.01); *A61F 13/84* (2013.01); *A61F 13/8405* (2013.01); *A61L 15/18* (2013.01); *A61L 15/20* (2013.01); *A61L 15/22* (2013.01); *A61L 15/225* (2013.01); *A61L 15/40* (2013.01); *A61L 15/46* (2013.01); *A61L 15/60* (2013.01); *B01J 20/264* (2013.01); *C08G 63/06* (2013.01); *C08G 63/52* (2013.01); *A61F 2013/8408* (2013.01); *A61F 2013/8458* (2013.01); *A61F 2013/8464* (2013.01); *A61L 2300/102* (2013.01); *A61L 2300/22* (2013.01); *A61L 2300/30* (2013.01); *A61L 2300/428* (2013.01);
(Continued)

(58) Field of Classification Search
CPC ....................................................... A61L 15/24
See application file for complete search history.

(56) References Cited

U.S. PATENT DOCUMENTS

| | | |
|---|---|---|
| 3,860,003 A | 1/1975 | Buell |
| 3,935,862 A | 2/1976 | Kraskin |
| (Continued) | | |

FOREIGN PATENT DOCUMENTS

| | | |
|---|---|---|
| EP | 0922452 | 6/1999 |
| EP | 0922456 | 6/1999 |
| (Continued) | | |

*Primary Examiner* — Benjamin J Packard
(74) *Attorney, Agent, or Firm* — Andrew J. Hagerty

(57) ABSTRACT

The present invention relates to absorbent articles comprising species of glyceride copolymers that provide unexpectedly improved softening performance and formulability.

1 Claim, 3 Drawing Sheets

(51) Int. Cl.
*A61L 15/20* (2006.01)
*A61L 15/22* (2006.01)
*A61L 15/18* (2006.01)
*A61F 13/84* (2006.01)
*A61F 13/47* (2006.01)
*A61F 13/496* (2006.01)
*B01J 20/26* (2006.01)
*C08G 63/52* (2006.01)
*A61F 13/511* (2006.01)

(52) U.S. Cl.
CPC ..... *A61L 2300/434* (2013.01); *A61L 2400/04* (2013.01); *B01J 2220/68* (2013.01)

(56) References Cited

U.S. PATENT DOCUMENTS

| | | |
|---|---|---|
| 4,011,389 A | 3/1977 | Langdon et al. |
| 4,556,560 A | 12/1985 | Buckingham |
| 5,059,282 A | 10/1991 | Ampulski et al. |
| 5,091,193 A | 2/1992 | Enjolras et al. |
| 5,221,274 A | 6/1993 | Buell et al. |
| 5,376,655 A | 12/1994 | Imaki et al. |
| 5,409,903 A | 4/1995 | Polak et al. |
| 5,554,145 A | 9/1996 | Roe et al. |
| 5,569,234 A | 10/1996 | Buell et al. |
| 5,580,411 A | 12/1996 | Nease et al. |
| 5,700,254 A | 12/1997 | McDowall et al. |
| 6,004,306 A | 12/1999 | Roe et al. |
| 6,066,673 A | 5/2000 | Underiner et al. |
| 6,632,504 B1 | 10/2003 | Gillespie et al. |
| 8,642,824 B2 | 2/2014 | Lemke et al. |
| 8,692,006 B2 | 4/2014 | Uptain et al. |
| 2008/0312622 A1 | 12/2008 | Hundorf et al. |
| 2011/0113679 A1 | 5/2011 | Cohen et al. |
| 2011/0160472 A1 | 6/2011 | Lemke et al. |
| 2014/0275595 A1 | 9/2014 | Wampler et al. |
| 2014/0275681 A1 | 9/2014 | Cohen et al. |

FOREIGN PATENT DOCUMENTS

| | | |
|---|---|---|
| WO | WO 95/10996 | 4/1995 |
| WO | WO 2000/59430 | 10/2000 |
| WO | WO 02/067809 | 9/2002 |
| WO | WO 2009/020665 | 2/2009 |
| WO | WO 2009/020667 | 2/2009 |

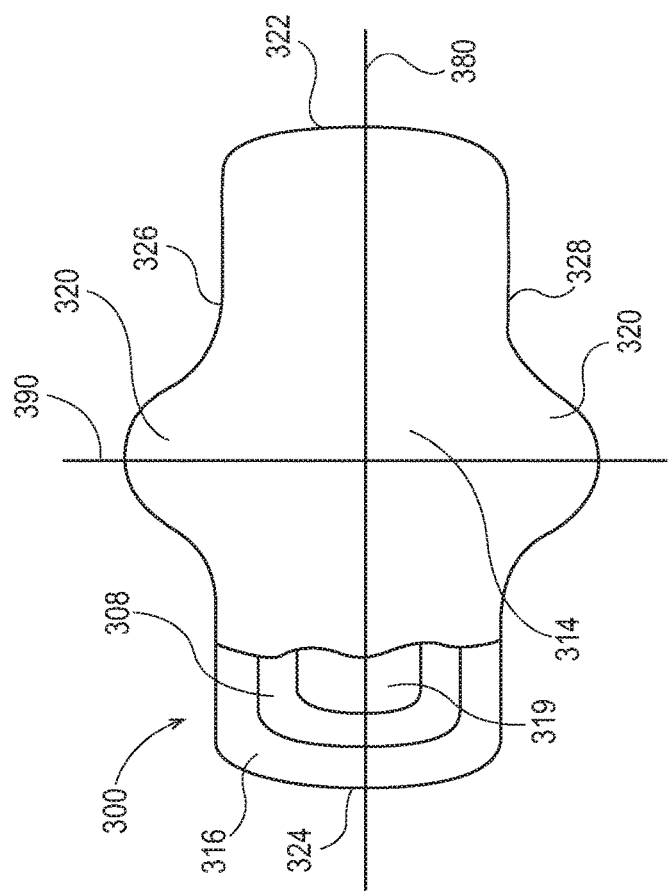

ABSORBENT ARTICLES COMPRISING GLYCERIDE COPOLYMERS

CROSS REFERENCE TO RELATED APPLICATION

This application claims the benefit of U.S. Provisional Application No. 62/401,474, filed on Sep. 29, 2016.

FIELD OF THE INVENTION

The present invention relates to absorbent articles as well as methods of using same.

BACKGROUND OF THE INVENTION

Absorbent articles for personal hygiene, such as disposable diapers for infants, training pants for toddlers, adult incontinence undergarments, and/or sanitary napkins are designed to absorb and contain bodily exudates, in particular large quantities of urine, runny BM, and/or menses (together the "fluids"). These absorbent articles may comprise several layers providing different functions, for example, a topsheet, a backsheet, and an absorbent core disposed between the topsheet and the backsheet, among other layers, if desired. Ideally, the parts of the article that can be felt by the consumer and/or the wearer connote softness. These parts include the topsheet, backsheet, barrier cuffs, waist band, and/or wings. There is a continuing need for articles with improved softness that can benefit contact with the wearer's skin. Applicants recognize that glyceride copolymers can serve as such a softening active.

While not being bound by theory, Applicants believe that the uncharged nature and/or the low degree of oligomerization of the disclosed glyceride copolymers result in the desired improved softness.

SUMMARY OF THE INVENTION

The present invention relates to absorbent articles comprising species of glyceride copolymers that provide unexpectedly improved softening performance and formulability.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting forms of the disclosure taken in conjunction with the accompanying drawings, wherein:

FIG. 3 is a top view of an absorbent article, wearer-facing surface facing the viewer, that is a sanitary napkin with some of the layers cut away in accordance with the present disclosure.

DETAILED DESCRIPTION OF THE INVENTION

Definitions

Figure 1:
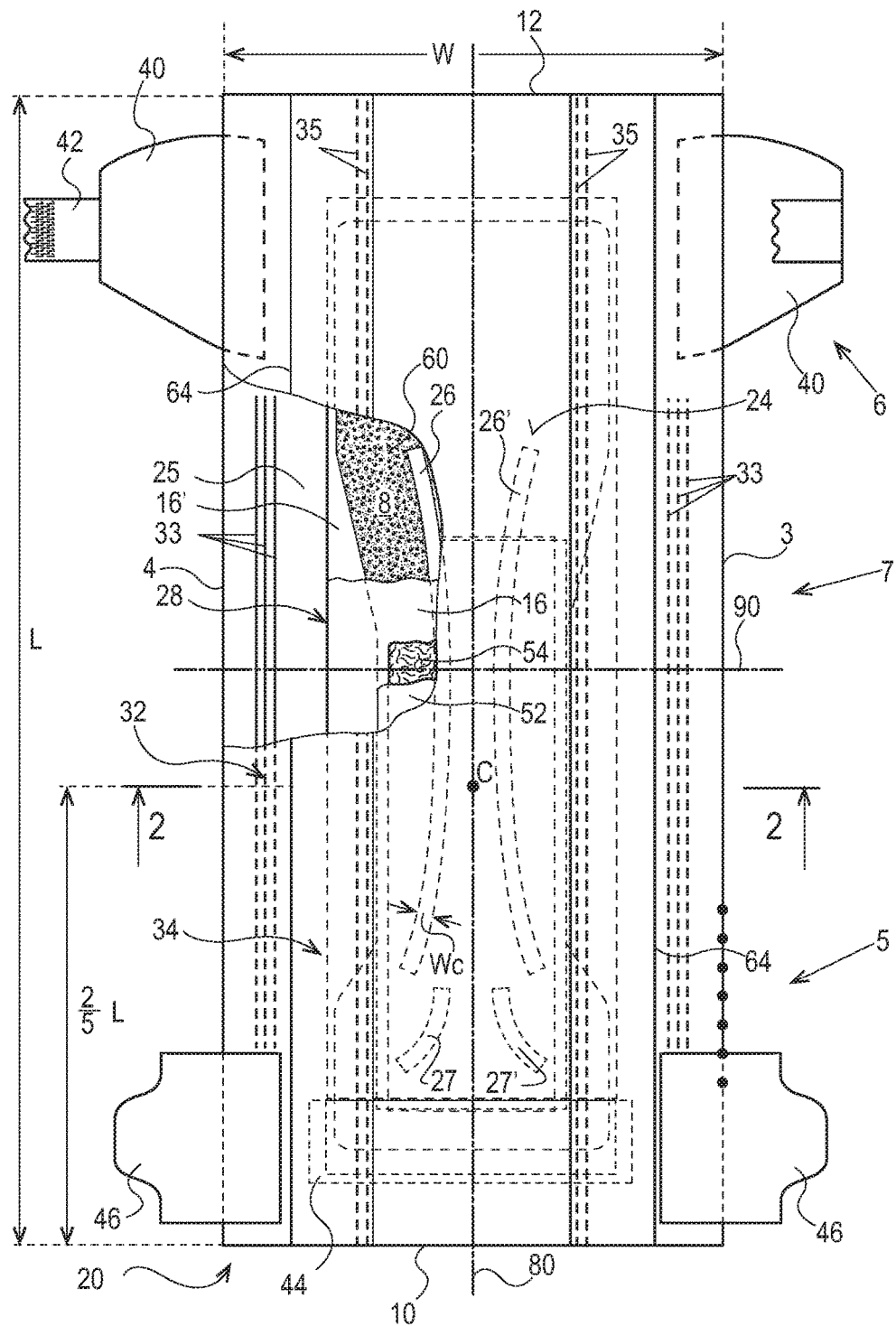
FIG. 1 is a top view of an absorbent article, wearer-facing surface facing the viewer, with some layers partially removed in accordance with the present disclosure.

As used herein, "natural oil", "natural feedstocks," or "natural oil feedstocks" refers to oils obtained from plants or animal sources. The term "natural oil" includes natural oil derivatives, unless otherwise indicated. The terms also include modified plant or animal sources (e.g., genetically modified plant or animal sources), and derivatives produced or modified by fermentation or enzymatic processes, unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include low erucic acid rapeseed oil (canola oil), high erucic acid rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil.

The term "natural oil glyceride" refers to a glyceryl ester of a fatty acid obtained from a natural oil. Such glycerides include monoacylglycerides, diacylglycerides, and triacylglyceriedes (triglycerides). In some embodiments, the natural oil glycerides are triglycerides. Analogously, the term "unsaturated natural oil glyceride" refers to natural oil glycerides, wherein at least one of its fatty acid residues contains unsaturation. For example, a glyceride of oleic acid is an unsaturated natural oil glyceride. The term "unsaturated alkenylized natural oil glyceride" refers to an unsaturated natural oil glyceride (as defined above) that is derivatized via a metathesis reaction with a sort-chain olefin (as defined below). In some cases, olefinizing process shortens one or more of the fatty acid chains in the compound. For example, a glyceride of 9-decenoic acid is an unsaturated alkenylized natural oil glyceride. Similarly, butenylized (e.g., with 1-butene and/or 2-butene) canola oil is a natural oil glyceride that has been modified via metathesis to contain some short-chain unsaturated $C_{10-15}$ ester groups.

The term "natural oil derivatives" refers to derivatives thereof derived from natural oil. The methods used to form these natural oil derivatives may include one or more of addition, neutralization, overbasing, saponification, transesterification, interesterification, esterification, amidation, hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification or a combination of two or more thereof. Examples of natural derivatives thereof may include carboxylic acids, gums, phospholipids, soapstock, acidulated soapstock, distillate or distillate sludge, fatty acids, fatty acid esters, as well as hydroxy substituted variations thereof, including unsaturated polyol esters. In some embodiments, the natural oil derivative may comprise an unsaturated carboxylic acid having from about 5 to about 30 carbon atoms, having one or more carbon-carbon double bonds in the hydrocarbon (alkene) chain. The natural oil derivative may also comprise an unsaturated fatty acid alkyl (e.g., methyl) ester derived from a glyceride of natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized oil (i.e., RBD soybean oil).

As used herein, the term "unsaturated polyol ester" refers to a compound having two or more hydroxyl groups wherein at least one of the hydroxyl groups is in the form of an ester and wherein the ester has an organic group including at least one carbon-carbon double bond.

The term "oligomeric glyceride moiety" is a moiety comprising two or more, in one aspect, up to 20, in another aspect, up to 10 constitutional units formed via olefin metathesis from natural oil glycerides and/or alkenylized natural oil glycerides.

The term "free hydrocarbon" refers to any one or combination of unsaturated or saturated straight, branched, or cyclic hydrocarbons in the $C_{2-30}$ range.

The term "metathesis monomer" refers to a single entity that is the product of an olefin metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis). In some embodiments, the term refers to a triglyceride or other unsaturated polyol ester that has not yet undergone an alkylidene unit interchange but contains at least one $C_{4-17}$ ester having a carbon-carbon double bond in the "omega minus n" position, where n=0, 1, 2, 3, 4, 5, or 6 and where the the ester moiety has at least n+3 carbon atoms.

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds. In some embodiments, the term "metathesis oligomer" may include metathesis reactions wherein greater than ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing greater than ten bonded groups derived from the reactant compounds.

As used herein, "metathesis" refers to olefin metathesis. As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. These higher order oligomers may comprise one or more of: metathesis monomers, metathesis dimers, metathesis trimers, metathesis tetramers, metathesis pentamers, and higher order metathesis oligomers (e.g., metathesis hexamers, metathesis, heptamers, metathesis octamers, metathesis nonamers, metathesis decamers, and higher than metathesis decamers and above). Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, the term "olefinized natural polyol ester and/or olefinized synthetic polyol ester" refers to the product produced by metathesizing a natural and/or synthetic polyol ester with a $C_{2-14}$ olefin, preferably $C_{2-6}$ olefin, more preferably $C_{3-4}$ olefin, and mixtures and isomers thereof.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin" or an "alpha-olefin," while an olefin having a non-terminal carbon-carbon double bond can be referred to as an "internal olefin." In some embodiments, the alpha-olefin is a terminal alkene, which is an alkene (as defined below) having a terminal carbon-carbon double bond. Additional carbon-carbon double bonds can be present.

The number of carbon atoms in any group or compound can be represented by the terms: "$C_z$", which refers to a group of compound having z carbon atoms; and "$C_{x-y}$", which refers to a group or compound containing from x to y, inclusive, carbon atoms. For example, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. As a further example, a "$C_{4-10}$ alkene" refers to an alkene molecule having from 4 to 10 carbon atoms, and, for example, includes, but is not limited to, 1-butene, 2-butene, isobutene, 1-pentene, 1-hexene, 3-hexene, 1-heptene, 3-heptene, 1-octene, 4-octene, 1-nonene, 4-nonene, and 1-decene.

As used herein, the terms "short-chain alkene" or "short-chain olefin" refer to any one or combination of unsaturated straight, branched, or cyclic hydrocarbons in the $C_{2-14}$ range, or the $C_{2-12}$ range, or the $C_{2-10}$ range, or the $C_{2-8}$ range. Such olefins include alpha-olefins, wherein the unsaturated carbon-carbon bond is present at one end of the compound. Such olefins also include dienes or trienes. Such olefins also include internal olefins. Examples of short-chain alkenes in the $C_{2-6}$ range include, but are not limited to: ethylene, propylene, 1-butene, 2-butene, isobutene, 1-pentene, 2-pentene, 2-methyl-1-butene, 2-methyl-2-butene, 3-methyl-1-butene, cyclopentene, 1,4-pentadiene, 1-hexene, 2-hexene, 3-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of short-chain alkenes in the $C_{7-9}$ range include 1,4-heptadiene, 1-heptene, 3,6-nonadiene, 3-nonene, 1,4,7-octatriene. In certain embodiments, it is preferable to use a mixture of olefins, the mixture comprising linear and branched low-molecular-weight olefins in the $C_{4-10}$ range. In some embodiments, it may be preferable to use a mixture of linear and branched $C_4$ olefins (i.e., combinations of: 1-butene, 2-butene, and/or isobutene). In other embodiments, a higher range of $C_{11-14}$ may be used.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group.

As used herein, "direct bond" refers to an embodiment where the identified moiety is absent from the structure, and is replaced by a bond between other moieties to which it is connected. For example, if the specification or claims recite A-D-E and D is defined as a direct bond, the resulting structure is A-E.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, the term "polyol" means an organic material comprising at least two hydroxy moieties.

As used herein, the term "$C_{10-14}$ unsaturated fatty acid ester" means a fatty acid ester that comprises 10, 11, 12, 13 or 14 carbon atoms, wherein the fatty acid ester chain has at least one carbon-carbon double bond.

In some instances herein, organic compounds are described using the "line structure" methodology, where chemical bonds are indicated by a line, where the carbon atoms are not expressly labeled, and where the hydrogen atoms covalently bound to carbon (or the C—H bonds) are not shown at all. For example, by that convention, the formula

represents n-propane. In some instances herein, a squiggly bond is used to show the compound can have any one of two or more isomers. For example, the structure

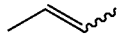

can refer to (E)-2-butene or (Z)-2-butene. The same is true when olefinic structures are drawn that are ambiguous as to which isomer is referred to. For example, $CH_3$—CH═CH—$CH_3$ can refer to (E)-2-butene or (Z)-2-butene.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

As used herein, the term "absorbent article" refers to disposable devices such as infant, child, or adult diapers, adult incontinence products, training pants, sanitary napkins, and the like which are placed against or in proximity to a body of a wearer to absorb and contain the various fluids (urine, menses, and/or runny BM) or bodily exudates (generally solid BM) discharged from the body.

As used herein, the term "nonwoven web" means a manufactured sheet, web, or batt of directionally or randomly orientated fibers, bonded by friction, and/or cohesion, and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers may have diameters ranging from less than about 0.001 mm to more than about 0.2 mm and may come in several different forms such as short fibers (known as staple, or chopped), continuous single fibers (filaments or monofilaments), untwisted bundles of continuous filaments (tow), and twisted bundles of continuous filaments (yarn). Nonwoven webs may be formed by many processes such as meltblowing, spunbonding, solvent spinning, electrospinning, carding, and airlaying. The basis weight of nonwoven webs is usually expressed in grams per square meter ($g/m^2$ or gsm).

As used herein, the terms "joined", "bonded", or "attached" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "machine direction" or "MD" is the direction that is substantially parallel to the direction of travel of a substrate as it is made. The "cross direction" or "CD" is the direction substantially perpendicular to the MD and in the plane generally defined by the substrate.

As used herein, the articles including "a" and "an" when used in a claim, are understood to mean one or more of what is claimed or described.

As used herein, the terms "include", "includes" and "including" are meant to be non-limiting.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated with the proviso that the sum of the percentage of all ingredients for a respective mixture/formula cannot exceed or be less than 100%.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Absorbent Article

Figure 2:
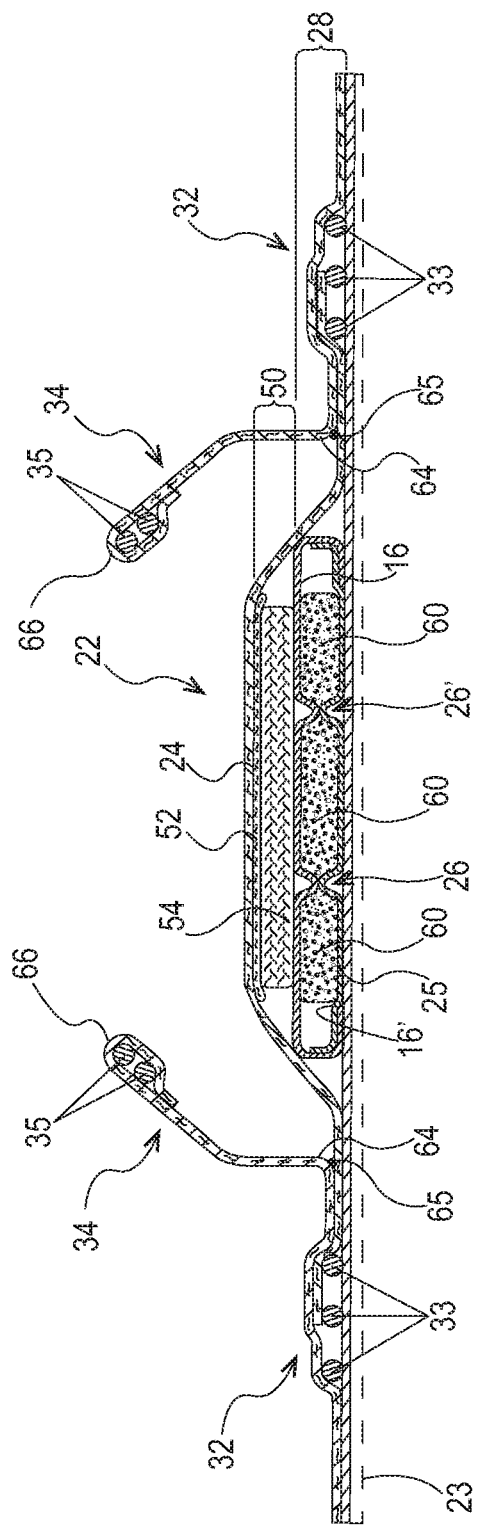
FIG. 2 is a cross-sectional view of the absorbent article taken about line 2-2 of FIG. 1 in accordance with the present disclosure.

An example absorbent article in the form of a diaper 20 is represented in FIGS. 1-3. FIG. 1 is a plan view of the example diaper 20, in a flat-out state, with portions of the structure being cut-away to more clearly show the construction of the diaper 20. The wearer-facing surface of the diaper 20 of FIG. 1 is facing the viewer. This diaper 20 is shown for illustration purpose only as the three-dimensional substrates of the present disclosure may be used as one or more components of an absorbent article.

The absorbent article 20 may comprise a liquid permeable topsheet 24, a liquid impermeable backsheet 25, an absorbent core 28 positioned at least partially intermediate the topsheet 24 and the backsheet 25, and barrier leg cuffs 34. The absorbent article may also comprise an acquisition and/or distribution system ("ADS") 50, which in the example represented comprises a distribution layer 54 and an acquisition layer 52, which will be further detailed below. The absorbent article may also comprise elasticized gasketing cuffs 32 comprising elastics 33 joined to a chassis of the absorbent article, typically via the topsheet and/or backsheet, and substantially planar with the chassis of the diaper.

The figures also show typical taped diaper components such as a fastening system comprising tabs 42 attached towards the rear edge of the article and cooperating with a landing zone 44 on the front of the absorbent article. The absorbent article may also comprise other typical elements, which are not represented, such as a rear elastic waist feature, a front elastic waist feature, transverse barrier cuff(s), and/or a lotion application, for example.

The absorbent article 20 comprises a front waist edge 10, a rear waist edge 12 longitudinally opposing the front waist edge 10, a first side edge 3, and a second side edge 4 laterally opposing the first side edge 3. The front waist edge 10 is the edge of the article which is intended to be placed towards the front of the user when worn, and the rear waist edge 12 is the opposite edge. The absorbent article may have a longitudinal axis 80 extending from the lateral midpoint of the front waist edge 10 to a lateral midpoint of the rear waist edge 12 of the article and dividing the article in two substantially symmetrical halves relative to the longitudinal axis 80, with the article placed flat and viewed from above as in FIG. 1. The absorbent article may also have a lateral axis 90 extending from the longitudinal midpoint of the first side edge 3 to the longitudinal midpoint of the second side edge 4. The length, L, of the article may be measured along the longitudinal axis 80 from the front waist edge 10 to the rear waist edge 12. The width, W, of the article may be measured along the lateral axis 90 from the first side edge 3 to the second side edge 4. The article may comprise a crotch point C defined herein as the point placed on the longitudinal axis at a distance of two fifth (2/5) of L starting from the front edge 10 of the article 20. The article may comprise a front waist region 5, a rear waist region 6, and a crotch region 7. The front waist region 5, the rear waist region 6, and the crotch region 7 each define 1/3 of the longitudinal length, L, of the absorbent article.

The topsheet 24, the backsheet 25, the absorbent core 28, and the other article components may be assembled in a variety of configurations, in particular by gluing or heat embossing, for example. Example absorbent article configurations are described generally in U.S. Pat. No. 3,860,003, U.S. Pat. No. 5,221,274, U.S. Pat. No. 5,554,145, U.S. Pat. No. 5,569,234, U.S. Pat. No. 5,580,411, and U.S. Pat. No. 6,004,306.

The absorbent core 28 may comprise an absorbent material comprising at least 80% by weight, at least 90% by weight, at least 95% by weight, or at least 99% by weight of superabsorbent polymers and a core wrap enclosing the superabsorbent polymers. The core wrap may typically comprise two materials, substrates, or nonwoven materials 16 and 16' for the top side and bottom side of the core. The core may comprises one or more channels, represented in FIG. 1 as the four channels 26, 26' and 27, 27'. The channels 26, 26', 27, and 27' are optional features. Instead, the core may not have any channels or may have any number of channels.

These and other components of the example absorbent article will now be discussed in more details.

Topsheet

The topsheet 24 may be the part of the absorbent article that is in contact with the wearer's skin. The topsheet 24 may be joined to the backsheet 25, the core 28 and/or any other layers as is known to those of skill in the art. Usually, the topsheet 24 and the backsheet 25 are joined directly to each other in some locations (e.g., on or close to the periphery of the absorbent article) and are indirectly joined together in other locations by directly joining them to one or more other elements of the article 20.

The topsheet 24 may be compliant, soft-feeling, and non-irritating to the wearer's skin. Further, a portion of, or all of, the topsheet 24 may be liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet 24 includes fibers, the fibers may be spunbond, carded, wet-laid, melt-blown, hydroentangled, or otherwise processed as is known in the art. A suitable topsheet comprising a web of staple-length polypropylene fibers is manufactured by Veratec, Inc., a Division of International Paper Company, of Walpole, Mass. under the designation P-8.

Any portion of the topsheet 24 may be coated with a lotion and/or a skin care composition as is generally disclosed in the art. The topsheet 24 may also comprise or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of fluids therethrough. The size of at least the primary apertures is important in achieving the desired fluid encapsulation performance. If the primary apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased. Typically, the total area of the apertures at the surface of a diaper may have an area of between about 10 cm$^2$ and about 50 cm$^2$ or between about 15 cm$^2$ and 35 cm$^2$. Examples of apertured topsheets are disclosed in U.S. Pat. No. 6,632,504, assigned to BBA NONWOVENS SIMPSONVILLE. Typical diaper topsheets have a basis weight of from about 10 to about 25 gsm or from about 12 to about 20 gsm, but other basis weights are within the scope of the present disclosure.

Backsheet

The backsheet 25 is generally that portion of the absorbent article 20 positioned adjacent the garment-facing surface of the absorbent core 28 and which prevents, or at least inhibits, the fluids and bodily exudates absorbed and contained therein from soiling articles such as bedsheets and undergarments. The backsheet 25 is typically impermeable, or at least substantially impermeable, to fluids (e.g., urine).

The backsheet may, for example, be or comprise a thin plastic film such as a thermoplastic film having a thickness of about 0.012 mm to about 0.051 mm. Example backsheet films include those manufactured by Tredegar Corporation, based in Richmond, Va., and sold under the trade name CPC2 film. Other suitable backsheet materials may include breathable materials which permit vapors to escape from the absorbent article 20 while still preventing, or at least inhibiting, fluids from passing through the backsheet 25. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

Any portion of the backsheet 25 may be coated with a lotion and/or a skin care composition as is generally disclosed in the art. The backsheet 25 may be joined to the topsheet 24, the absorbent core 28, and/or any other element of the absorbent article 20 by any attachment methods known to those of skill in the art. Suitable attachment methods are described above with respect to methods for joining the topsheet 24 to other elements of the article 20.

An outer cover 23 may cover at least a portion of, or all of, the backsheet 25 to form a soft garment-facing surface of the absorbent article. The outer cover 23 may be formed of one or more nonwoven materials. The outer cover 23 is illustrated in dash in FIG. 2, as an example. The outer cover 23 may be joined to at least a portion of the backsheet 25 through mechanical bonding, adhesive bonding, or other suitable methods of attachment.

Absorbent Core

As used herein, the term "absorbent core" refers to the component of the absorbent article having the most absorbent capacity and comprising an absorbent material and a core wrap or core bag enclosing the absorbent material. The term "absorbent core" does not include the acquisition and/or distribution system or any other components of the article which are not either integral part of the core wrap or core bag or placed within the core wrap or core bag. The absorbent core may comprise, consist essentially of, or consist of, a core wrap, an absorbent material (e.g., superabsorbent polymers) as discussed, and glue.

The absorbent core 28 may comprise an absorbent material with a high amount of superabsorbent polymers (herein abbreviated as "SAP") enclosed within the core wrap. The SAP content may represent 70%-100% or at least 70%, 75%, 80%, 85%, 90%, 95%, 99%, or 100%, by weight of the absorbent material, contained in the core wrap. The core wrap is not considered as absorbent material for the purpose of assessing the percentage of SAP in the absorbent core. The core may also contain airfelt or cellulosic fibers with or without SAP.

By "absorbent material" it is meant a material which has some absorbency property or liquid retaining properties, such as SAP, cellulosic fibers as well as synthetic fibers. Typically, glues used in making absorbent cores have no or little absorbency properties and are not considered as absorbent material. The SAP content may be higher than 80%, for example at least 85%, at least 90%, at least 95%, at least 99%, and even up to and including 100% of the weight of the absorbent material contained within the core wrap. This provides a relatively thin core compared to a conventional core typically comprising between 40-60% SAP and high content of cellulose fibers. The conventional cores are also within the scope of the present disclosure. The absorbent material may in particular comprises less than 15% weight percent or less than 10% weight percent of natural, cellulosic, or synthetic fibers, less than 5% weight percent, less than 3% weight percent, less than 2% weight percent, less than 1% weight percent, or may even be substantially free of natural, cellulosic, and/or synthetic fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

The SAP may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The fibers may also be in the form of a long filament that may be woven. SAP may be spherical-like particles. The absorbent core may comprise one or more types of SAP.

For most absorbent articles, liquid discharges from a wearer occur predominately in the front half of the absorbent article, in particular for a diaper. The front half of the article (as defined by the region between the front edge and a transversal line placed at a distance of half L from the front waist edge 10 or rear waist edge 12 may therefore may comprise most of the absorbent capacity of the core. Thus, at least 60% of the SAP, or at least 65%, 70%, 75%, 80%, or 85% of the SAP may be present in the front half of the absorbent article, while the remaining SAP may be disposed in the rear half of the absorbent article. Alternatively, the SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m$^2$. The areas of the channels (e.g., 26, 26', 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. The core wrap may be formed by any materials suitable for receiving and containing the absorbent material. Typical substrate materials used in the production of conventional cores may be used, in particular paper, tissues, films, wovens or nonwovens, or laminates or composites of any of these.

If the core wrap is formed by two substrates 16, 16', four seals may be used to enclose the absorbent material 60 within the core wrap. For example, a first substrate 16 may be placed on one side of the core (the top side as represented in the Figures) and extend around the core's longitudinal edges to at least partially wrap the opposed bottom side of the core. The second substrate 16' may be present between the wrapped flaps of the first substrate 16 and the absorbent material 60. The flaps of the first substrate 16 may be glued to the second substrate 16' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. In an example, neither the first nor the second substrates need to be shaped, so that they may be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 8 may be defined by the periphery of the layer formed by the absorbent material 60 within the core wrap, as seen from the top side of the absorbent core. The absorbent material deposition area 8 may have various shapes, in particular, a so-called "dog bone" or "hour-glass" shape, which shows a tapering along its width towards the middle or "crotch" region of the core. In this way, the absorbent material deposition area 8 may have a relatively narrow width in an area of the core intended to be placed in the crotch region of the absorbent article, as illustrated in FIG. 1. This may provide better wearing comfort. The absorbent material deposition area 8 may also be generally rectangular, but other deposition areas, such as a rectangular, "T," "Y," "sand-hour," or "dog-bone" shapes are also within the scope of the present disclosure. The absorbent material may be deposited using any suitable techniques, which may allow relatively precise deposition of SAP at relatively high speed.

Channels

The absorbent material deposition area 8 may comprise at least one channel 26, which is at least partially oriented in the longitudinal direction of the article 80 (i.e., has a longitudinal vector component). Other channels may be at least partially oriented in the lateral direction (i.e., has a lateral vector component) or in any other direction. In the following, the plural form "channels" will be used to mean "at least one channel". The channels may have a length L' projected on the longitudinal axis 80 of the article that is at least 10% of the length L of the article. The channels may be formed in various ways. For example, the channels may be formed by zones within the absorbent material deposition area 8 which may be substantially free of, or free of, absorbent material, in particular SAP. In addition or alternatively, the channel(s) may also be formed by continuously or discontinuously bonding the top side of the core wrap to the bottom side of the core wrap through the absorbent material deposition area 8. The channels may be continuous but it is also envisioned that the channels may be intermittent. The acquisition-distribution system or layer 50, or another layer of the article, may also comprise channels, which may or not correspond to the channels of the absorbent core.

In some instances, the channels may be present at least at the same longitudinal level as the crotch point C or the lateral axis 60 in the absorbent article, as represented in FIG. 1 with the two longitudinally extending channels 26, 26'. The channels may also extend from the crotch region 7 or may be present in the front waist region 5 and/or in the rear waist region 6 of the article.

The absorbent core 28 may also comprise more than two channels, for example, at least 3, at least 4, at least 5, or at least 6 or more.

In order to reduce the risk of fluid leakages, the longitudinal main channels may not extend up to any of the edges of the absorbent material deposition area 8, and may therefore be fully encompassed within the absorbent material deposition area 8 of the core. The smallest distance between a channel and the closest edge of the absorbent material deposition area 8 may be at least 5 mm.

The channels may have a width Wc along at least part of their length which is at least 2 mm, at least 3 mm, at least 4 mm, up to for example 20 mm, 16 mm, or 12 mm, for example. The width of the channel(s) may be constant through substantially the whole length of the channel or may vary along its length. At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 16 and the second substrate 16') and/or the topsheet 24 to the backsheet 25 together through the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

Barrier Leg Cuffs

The absorbent article may comprise a pair of barrier leg cuffs 34. Each barrier leg cuff may be formed by a piece of material which is bonded to the article so it may extend upwards from a wearer-facing surface of the absorbent article and provide improved containment of fluids and other body exudates approximately at the junction of the torso and legs of the wearer. The barrier leg cuffs are delimited by a proximal edge 64 joined directly or indirectly to the topsheet 24 and/or the backsheet 25 and a free terminal edge 66, which is intended to contact and form a seal with the wearer's skin. The barrier leg cuffs 34 extend at least partially between the front waist edge 10 and the rear waist edge 12 of the absorbent article on opposite sides of the longitudinal axis 80 and are at least present at the level of the crotch point (C) or crotch region. The barrier leg cuffs may be joined at the proximal edge 64 with the chassis of the article by a bond 65 which may be made by gluing, fusion bonding, or a combination of other suitable bonding processes. The bond 65 at the proximal edge 64 may be continuous or intermittent. The bond 65 closest to the raised section of the leg cuffs delimits the proximal edge 64 of the standing up section of the leg cuffs.

The barrier leg cuffs may be integral with the topsheet 24 or the backsheet 25 or may be a separate material joined to the article's chassis. Each barrier leg cuff 34 may comprise one, two or more elastic strings 35 close to the free terminal edge 66 to provide a better seal.

In addition to the barrier leg cuffs 34, the article may comprise gasketing cuffs 32, which are joined to the chassis of the absorbent article, in particular to the topsheet 24 and/or the backsheet 25 and are placed externally relative to the barrier leg cuffs. The gasketing cuffs 32 may provide a better seal around the thighs of the wearer. Each gasketing leg cuff may comprise one or more elastic strings or elastic elements 33 in the chassis of the absorbent article between the topsheet 24 and backsheet 25 in the area of the leg openings. All, or a portion of, the barrier leg cuffs and/or gasketing cuffs may be treated with a lotion or another skin care composition.

Acquisition-Distribution System

The absorbent articles of the present disclosure may comprise an acquisition-distribution layer or system 50 ("ADS"). One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise two layers: a distribution layer 54 and an acquisition layer 52 disposed between the absorbent core and the topsheet, but the present disclosure is not so limited.

The ADS may comprise SAP as this may slow the acquisition and distribution of the fluids. Suitable ADS are described in WO 2000/59430 (Daley), WO 95/10996 (Richards), U.S. Pat. No. 5,700,254 (McDowall), and WO 02/067809 (Graef), for example.

The distribution layer of the ADS may comprise at least 50% by weight of cross-linked cellulose fibers. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under wearer weight. This may provide the core with a higher void volume, permeability, and liquid absorption, and hence reduced leakage and improved dryness.

The distribution layer comprising the cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In still another example, the layer may comprise about 68% by weight chemically cross-linked cellulose fibers, about 16% by weight untreated pulp fibers, and about 16% by weight PET fibers. In yet another example, the layer of cross-linked cellulose fibers may comprise from about 90 to about 100% by weight chemically cross-linked cellulose fibers.

The ADS 50 may comprise an acquisition layer 52. The acquisition layer may be disposed between the distribution layer 54 and the topsheet 24. The acquisition layer 52 may be or may comprise a nonwoven material, such as an SMS or SMMS material, comprising a spunbonded, a melt-blown and a further spunbonded layer or alternatively a carded chemical-bonded nonwoven. The nonwoven material may be latex bonded.

A further acquisition layer may be used in addition to a first acquisition layer described above. For example, a tissue layer may be placed between the first acquisition layer and the distribution layer. The tissue may have enhanced capillarity distribution properties compared to the acquisition layer described above.

Fastening System

The absorbent article may include a fastening system. The fastening system may be used to provide lateral tensions about the circumference of the absorbent article to hold the absorbent article on the wearer as is typical for taped diapers. This fastening system may not be necessary for training pant articles since the waist region of these articles is already bonded. The fastening system may comprise a fastener such as tape tabs, hook and loop fastening components, interlocking fasteners such as tabs & slots, buckles, buttons, snaps, and/or hermaphroditic fastening components, although any other suitable fastening mechanisms are also within the scope of the present disclosure. A landing zone 44 is normally provided on the garment-facing surface of the front waist region 5 for the fastener to be releasably attached thereto.

Pants

An alternate configuration for absorbent articles is one for absorbent pants in which the central chassis structure does not extend to, or form, the front and rear waist edges of the pant. Rather, an elasticized belt structure entirely encircles the wearer's waist and forms the waist edge about the entire pant, and the side/hip panels. The central chassis is joined to the belt structure, usually on the inside thereof, with its ends disposed at locations in the front and rear waist regions somewhat below the waist edges of the belt structure. The elastic belt is usually relatively wide (in the longitudinal direction) and elastically stretchable in the lateral direction. It entirely encircles the wearer's waist, and thereby covers a relatively large amount of the wearer's skin. This configuration is sometimes known as a "belt" or "balloon" configuration (hereinafter, "belt" configuration).

In more detail, an absorbent article may have a front region, a rear region, and a crotch region disposed therebetween, further comprising a liquid permeable topsheet, a backsheet, and an absorbent core disposed between the topsheet and the backsheet. The article then may have a central chassis occupying the crotch region, and a belt structure disposed about the central chassis, the belt structure overlaying the backsheet to the outside thereof in the front and rear regions, and the belt structure overlapping and extending laterally and longitudinally outward from the chassis. The belt structure may comprise an outer nonwoven and an inner nonwoven and have elastic strands therebetween. The belt structure may further have a front belt portion having a front waist edge, and front left and right side edges; and a rear belt portion having a rear waist edge and rear left and right side edges, wherein the respective front and rear left side edges and the respective front and rear right side edges are joined, forming a waist opening and left and right leg openings.

Any pant configuration may have any of the article components described herein, for example, the topsheet, backsheet, core, barrier cuffs, and/or liquid management system layers described herein, along with any of the lotion compositions described herein. Further descriptions and embodiments of pant configurations may be found in U.S. Ser. No. 62/210,635.

Front and Rear Ears

The absorbent article may comprise front ears 46 and rear ears 40. The ears may be an integral part of the chassis, such as formed from the topsheet 24 and/or backsheet 26 as side panels. Alternatively, as represented on FIG. 1, the ears may be separate elements attached by gluing, heat embossing, and/or pressure bonding. The rear ears 40 may be stretchable to facilitate the attachment of the tabs 42 to the landing zone 44 and maintain the taped diapers in place around the wearer's waist. The rear ears 40 may also be elastic or extensible to provide a more comfortable and contouring fit by initially conformably fitting the absorbent article to the wearer and sustaining this fit throughout the time of wear well past when absorbent article has been loaded with fluids or other bodily exudates since the elasticized ears allow the sides of the absorbent article to expand and contract.

Elastic Waist Feature

The absorbent article 20 may also comprise at least one elastic waist feature (not represented) that helps to provide improved fit and containment. The elastic waist feature is generally intended to elastically expand and contract to dynamically fit the wearer's waist. The elastic waist feature may extend at least longitudinally outwardly from at least one waist edge of the absorbent core 28 and generally forms at least a portion of the end edge of the absorbent article. Disposable diapers may be constructed so as to have two elastic waist features, one positioned in the front waist region and one positioned in the rear waist region. Any portion of a waist region may be coated with a lotion and/or a skin care composition as is generally disclosed in the art.

Relations Between the Layers

Typically, adjacent layers and components may be joined together using conventional bonding methods, such as adhesive coating via slot coating or spraying on the whole or part of the surface of the layer, thermo-bonding, pressure bonding, or combinations thereof. This bonding is not represented in the Figures (except for the bonding between the raised element of the leg cuffs 65 with the topsheet 24) for clarity and readability, but bonding between the layers of the article should be considered to be present unless specifically excluded. Adhesives may be used to improve the adhesion of the different layers between the backsheet 25 and the core wrap. The glue may be any suitable hotmelt glue known in the art.

Sanitary Napkin

The three-dimensional substrates of the present disclosure may form a portion of a topsheet, form the topsheet, form a portion of, or all of a secondary topsheet, or be positioned on or joined to at least a portion of the topsheet of a sanitary napkin. Referring to FIG. 9, the absorbent article may comprise a sanitary napkin 300. The sanitary napkin 300 may comprise a liquid permeable topsheet 314, a liquid impermeable, or substantially liquid impermeable, backsheet 316, and an absorbent core 308. The absorbent core 308 may have any or all of the features described herein with respect to the absorbent cores 28 and, in some forms, may have a secondary topsheet instead of the acquisition-distribution system disclosed above. The sanitary napkin 300 may also comprise wings 320 extending outwardly with respect to a longitudinal axis 380 of the sanitary napkin 300. Any portion of the wings may be coated with a lotion and/or a skin care composition as is generally disclosed in the art. The sanitary napkin 300 may also comprise a lateral axis 390. The wings 320 may be joined to the topsheet 314, the backsheet 316, and/or the absorbent core 308. The sanitary napkin 300 may also comprise a front edge 322, a rear edge 324 longitudinally opposing the front edge 322, a first side edge 326, and a second side edge 328 longitudinally opposing the first side edge 326. The longitudinal axis 380 may extend from a midpoint of the front edge 322 to a midpoint of the rear edge 324. The lateral axis 390 may extend from a midpoint of the first side edge 326 to a midpoint of the second side edge 328. The sanitary napkin 300 may also be provided with additional features commonly found in sanitary napkins as is generally known in the art, such as a secondary topsheet 319, for example.

Any of the compositions described herein may be applied to or be part of a composition applied to at least one component of an absorbent article, wherein said absorbent article components are selected from the group consisting of a topsheet, a secondary topsheet, back sheet, barrier cuff, waist band, wing, and waist feature.

Compositions, Articles, Methods of Use and Treated Articles Paragraphs (a) Through (vv)

The following compositions, methods of use and treated articles are disclosed:

(a) A composition comprising,
    A) a material selected from the group consisting of:
        (i) a first glyceride copolymer having formula (I):

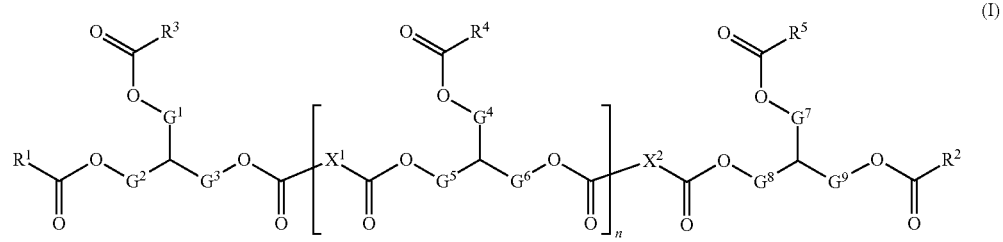

wherein:
each $R^1$, $R^2$, $R^3$, $R^4$, and $R^5$ in first glyceride copolymer is independently selected from the group consisting of an oligomeric glyceride moiety, a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties; and/or wherein each of the following combinations of moieties may each independently be covalently linked:
$R^1$ and $R^3$,
$R^2$ and $R^5$,
$R^1$ and an adjacent $R^4$,
$R^2$ and an adjacent $R^4$,
$R^3$ and an adjacent $R^4$,
$R^5$ and an adjacent $R^4$, or
any two adjacent $R^4$
such that the covalently linked moieties form an alkenylene moiety;
each $X^1$ and $X^2$ in said first glyceride copolymer is independently selected from the group consisting of a $C_{1-32}$ alkylene, a substituted $C_{1-32}$ alkylene wherein the substituent is one or more —OH moieties, a $C_{2-32}$ alkenylene or a substituted $C_{2-32}$ alkenylene wherein the substituent is one or more —OH moieties;
two of $G^1$, $G^2$, and $G^3$ are —$CH_2$—, and one of $G^1$, $G^2$, and $G^3$ is a direct bond;
for each individual repeat unit in the repeat unit having index n, two of $G^4$, $G^5$, and $G^6$ are —$CH_2$—, and one of $G^4$, $G^5$, and $G^6$ is a direct bond, and the values $G^4$, $G^5$, and $G^6$ for each individual repeat unit are independently selected from the values of $G^4$, $G^5$, and $G^6$ in other repeating units;
two of $G^7$, $G^8$, and $G^9$ are —$CH_2$—, and one of $G^7$, $G^8$, and $G^9$ is a direct bond;
n is an integer from 3 to 250;
with the proviso for each of said first glyceride copolymers at least one of $R^1$, $R^2$, $R^3$, and $R^5$, and/or at least one $R^4$ in one individual repeat unit of said repeat unit having index n, is selected from the group consisting of: 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-octadecatrienyl; 9-methyl-8-decenyl; 9-methyl-8-undecenyl; 10-methyl-8-undecenyl; 12-methyl-8,11-tridecadienyl; 12-methyl-8,11-tetradecadienyl; 13-methyl-8,11-tetradecadienyl; 15-methyl-8,11,14-hexadecatrienyl; 15-methyl-8,11,14-heptadecatrienyl; 16-methyl-8,11,14-heptadecatrienyl; 12-tridecenyl; 12-tetradecenyl; 12-pentadecenyl; 12-hexadecenyl; 13-methyl-12-tetradecenyl; 13-methyl-12-pentadecenyl; and 14-methyl-12-pentadecenyl; in one aspect, said first glyceride copolymer comprises based on total weight of first glyceride copolymer, from about 3% to about 30%, from about 3% to about 25%, or from about 5% to about 20% $C_{9-13}$ alkenyl moieties; in one aspect, said first glyceride copolymer comprises, based on total weight of first glyceride copolymer, from about 3% to about 30%, from about 3% to about 25%, or from about 3% to about 20% $C_{9-12}$ alkenyl moieties; in one aspect, said first glyceride copolymer comprises, based on total weight of first glyceride copolymer, from about 0.1% to about 30%, from about 0.1% to about 25%, from about 0.2% to about 20%, or from about 0.5% to about 15% $C_{9-10}$ alkenyl moieties; and
(ii) optionally, a second glyceride copolymer, which comprises constitutional units formed from reacting, in the presence of a metathesis catalyst, one or more compounds from each of the compounds having the following formulas:

Formula (IIa)

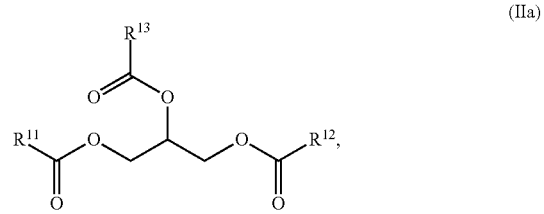

Formula (IIb)

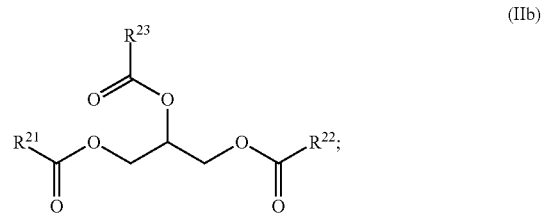

wherein,
each $R^{11}$, $R^{12}$, and $R^{13}$ is independently a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties with the proviso that at least one of $R^{11}$, $R^{12}$, and $R^{13}$ is a $C_{2-24}$ alkenyl or a substituted $C_{2-24}$ alkenyl wherein the substituent is one or more —OH moieties; and
each $R^{21}$, $R^{22}$, and $R^{23}$ is independently a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties, with the proviso that at least one of $R^{21}$, $R^{22}$, and $R^{23}$ is 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-octadecatrienyl; 9-methyl-8-decenyl; 9-methyl-8-undecenyl; 10-methyl-8-undecenyl; 12-methyl-8,11-tridecadienyl; 12-methyl-8,11-tetradecadienyl; 13-methyl-8,11-tetradecadienyl; 15-methyl-8,11,14-hexadecatrienyl; 15-methyl-8,11,14-heptadecatrienyl; 16-methyl-8,11,14-heptadecatrienyl; 12-tridecenyl; 12-tetradecenyl; 12-pentadecenyl; 12-hexadecenyl; 13-methyl-12-tetradecenyl; 13-methyl-12-pentadecenyl; and 14-methyl-12-pentadecenyl;
wherein the number ratio of constitutional units formed from monomer compounds of formula (IIa) to constitutional units formed from monomer compounds of formula (IIb) is no more than 10:1; and (iv) mixtures thereof; and
B) optionally a material selected from the group consisting of emollients, structuring agents, viscosity enhancers, surfactants, skin care ingredients, vitamins, moisturizers, perfumes, aesthetic ingredients, enzyme inhibitors, and combinations thereof.
(b) The composition of Paragraph (a) wherein said first and second glyceride copolymers have a weight average molecular weight of from about 4,000 g/mol to about 150,000 g/mol, from about 5,000 g/mol to about 130,000 g/mol, from about 6,000 g/mol to about 100,000 g/mol, from about 7,000 g/mol to about 50,000 g/mol, from about 8,000 g/mol to about 30,000 g/mol, or from about 8,000 g/mol to about 20,000 g/mol.
(c) The composition according to Paragraphs (a) through (b) wherein said first and second glyceride copolymers are produced by a process comprising metathesis; in one aspect, said process comprises reacting two or more monomers in the presence of the metathesis catalyst as part of a reaction mixture, wherein the weight-to-weight ratio of the monomer compounds of formula (IIa) to the monomer compounds of formula (IIb) in the reaction mixture is no more than 10:1, no more than 9:1, no more than 8:1, no more than 7:1, no more than 6:1, no more than 5:1, no more than 4:1, no more than 3:1, no more than 2:1, or no more than 1:1; in one aspect, the metathesis catalyst is an organo-ruthenium compound, an organo-osmium compound, an organo-tungsten compound, or an organo-molybdenum compound.
(d) The composition according to Paragraphs (a) through (c), wherein for said first glyceride copolymer at least one of $R^1$, $R^2$, $R^3$, $R^4$, or $R^5$ is a $C_{9-13}$ alkenyl, in one aspect, at least one of $R^1$, $R^2$, $R^3$, $R^4$, or $R^5$ is a $C_{9-12}$ alkenyl, in another aspect, at least one of $R^1$, $R^2$, $R^3$, $R^4$, or $R^5$ is a $C_{9-10}$ alkenyl.
(e) The composition according to Paragraphs (a) through (d), wherein for said second glyceride copolymer at least one of $R^{11}$, $R^{12}$, $R^{13}$, $R^{21}$, $R^{22}$ or $R^{23}$ is a $C_{9-13}$ alkenyl, in one aspect, at least one $R^{11}$, $R^{12}$, $R^{13}$, $R^{21}$, $R^{22}$, or $R^{23}$ is a $C_{9-12}$ alkenyl, in another aspect, at least one of $R^{11}$, $R^{12}$, $R^{13}$, $R^{21}$, $R^{22}$, or $R^{23}$ is a $C_{9-10}$ alkenyl.
(f) The composition according to Paragraphs (a) through (e), wherein the first glyceride copolymer's $G^1$ and $G^2$ moieties are —$CH_2$— and $G^3$ is a direct bond.
(g) The composition according to any of Paragraphs (a) through (e), wherein the first glyceride copolymer's $G^1$ and $G^3$ moieties are —$CH_2$— and $G^2$ is a direct bond.
(h) The composition according to any of Paragraphs (a) through (e), wherein the first glyceride copolymer's $G^2$ and $G^3$ moieties are —$CH_2$— and $G^1$ is a direct bond.
(I) The composition according to Paragraphs (a) through (h), wherein for the first glyceride copolymer, at least one of, $G^4$ and $G^5$ are —$CH_2$— and $G^6$ is a direct bond.
(j) The composition according to any of Paragraphs (a) through (h), wherein for the first glyceride copolymer, at least one of, $G^4$ and $G^6$ are —$CH_2$— and $G^5$ is a direct bond.
(k) The composition according to any of Paragraphs (a) through (h), wherein for the first glyceride copolymer, at least one of, $G^5$ and $G^6$ are —$CH_2$— and $G^4$ is a direct bond.
(l) The composition according to any of Paragraphs (a) through (k), wherein for the first glyceride copolymer, at least one of, $G^7$ and $G^8$ are —$CH_2$— and $G^9$ is a direct bond.
(m) The composition according to Paragraphs (a) through (k), wherein for the first glyceride copolymer, at least one of $G^7$ and $G^9$ are —$CH_2$— and $G^8$ is a direct bond.
(n) The composition according to Paragraphs (a) through (k), wherein for the first glyceride copolymer, at least one of $G^8$ and $G^9$ are —$CH_2$— and $G^7$ is a direct bond.
(o) The composition according to any of Paragraphs (a) through (n), wherein for the first glyceride copolymer, each $X^1$ is independently selected from the group consisting of —$(CH_2)_{16}$—, —$(CH_2)_{18}$—, —$(CH_2)_{19}$—, —$(CH_2)_{20}$—, —$(CH_2)_{22}$—, —$(CH_2)_{24}$—, —$(CH_2)_{25}$—, —$(CH_2)_{28}$—, —$(CH_2)_7$—CH=CH—$(CH_2)_7$—, —$(CH_2)_7$—CH=CH—$CH_2$—CH=CH—$(CH_2)_7$—, —$(CH_2)_7$—CH=CH—$CH_2$—CH=CH—$CH_2$—CH=CH—$(CH_2)_7$—, —$(CH_2)_7$—CH=CH—$CH_2$—CH=CH—$CH_2$—CH=CH—$(CH_2)_7$—, —$(CH_2)_7$—CH=CH—$CH_2$—CH=CH—$CH_2$—CH=CH—$CH_2$—CH=CH—$(CH_2)_7$—, —$(CH_2)_{11}$—CH=CH—$(CH_2)_{11}$—, —$(CH_2)_7$—CH=CH—$CH_2$—CH=CH—$(CH_2)_{11}$—, —$(CH_2)_{11}$—CH=CH—$CH_2$—CH=CH—$(CH_2)_7$—, —$(CH_2)_7$—CH=CH—$CH_2$—CH=CH—$CH_2$—CH=CH—$(CH_2)_{11}$—, —$(CH_2)_{11}$—CH=CH—$CH_2$—CH=CH—$CH_2$—CH=CH—$(CH_2)_7$—, —$(CH_2)_9$—CH=CH—$(CH_2)_7$—, —$(CH_2)_7$—CH=CH—$(CH_2)_9$—, —$(CH_2)_{11}$—CH=CH—$(CH_2)_7$—, or —$(CH_2)_7$—CH=CH—$(CH_2)_{11}$—.
(p) The composition according to any of Paragraphs (a) through (m), wherein for the first glyceride copolymer, each $X^2$ is independently selected from the group consisting of —$(CH_2)_{16}$—, —$(CH_2)_{18}$—, —$(CH_2)_{19}$—, —$(CH_2)_{20}$—, —$(CH_2)_{22}$—, —$(CH_2)_{24}$—, —$(CH_2)_{25}$—, —$(CH_2)_{28}$—, —$(CH_2)_7$—CH=CH—$(CH_2)_7$—, —$(CH_2)_7$—CH=CH—$CH_2$—CH=CH—$(CH_2)_7$—, —$(CH_2)_7$—CH=CH—$CH_2$—CH=CH—$CH_2$—CH=CH—$(CH_2)_7$—, —$(CH_2)_7$—CH=CH—$CH_2$—CH=CH—$CH_2$—CH=CH—$(CH_2)_7$—, —$(CH_2)_7$—CH=CH—$CH_2$—CH=CH—$CH_2$—CH=CH—$CH_2$—CH=CH—$(CH_2)_7$—, —$(CH_2)_{11}$—CH=CH—$(CH_2)_{11}$—, —$(CH_2)_7$—CH=CH—$CH_2$—CH=CH—$(CH_2)_{11}$—, —$(CH_2)_{11}$—CH=CH—$CH_2$—CH=CH—$(CH_2)_7$—, —$(CH_2)_7$—CH=CH—$CH_2$—CH=CH—$CH_2$—CH=CH—$(CH_2)_{11}$—, —$(CH_2)_{11}$—CH=CH—$CH_2$—CH=CH—$CH_2$—CH=CH—$(CH_2)_7$—, —$(CH_2)_9$—CH=CH—$(CH_2)_7$—, —$(CH_2)_7$—CH=CH—$(CH_2)_9$—, —$(CH_2)_{11}$—CH=CH—$(CH_2)_7$—, or —$(CH_2)_7$—CH=CH—$(CH_2)_{11}$—.
(q) The composition according to any of Paragraphs (a) through (p), wherein for the first glyceride copolymer, $R^1$ is a $C_{1-24}$ alkyl or a $C_{2-24}$ alkenyl; in one aspect, $R^1$ is selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl, in another aspect, $R^1$ is selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(r) The composition according to any of Paragraphs (a) through (q), wherein for the first glyceride copolymer, $R^2$ is a $C_{1-24}$ alkyl or a $C_{2-24}$ alkenyl; in one aspect, $R^2$ is selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in another aspect, $R^2$ is selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(s) The composition according to any of Paragraphs (a) through (r), wherein for the first glyceride copolymer, $R^3$ is a $C_{1-24}$ alkyl or a $C_{2-24}$ alkenyl; in one aspect, $R^3$ is selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11, 14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in another aspect, $R^3$ is selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(t) The composition according to any of Paragraphs (a) through (s), wherein for the first glyceride copolymer, each $R^4$ is independently selected from a $C_{1-24}$ alkyl and a $C_{2-24}$ alkenyl; in one aspect, each $R^4$ is independently selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11, 14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in another aspect, each $R^4$ is independently selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(u) The composition according to any of Paragraphs (a) through (t), wherein for the first glyceride copolymer, $R^5$ is a $C_{1-24}$ alkyl or a $C_{2-24}$ alkenyl; in one aspect, $R^5$ is selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11, 14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in another aspect, $R^5$ is selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(v) The composition according to any of Paragraphs (a) through (u), wherein for the first glyceride copolymer, n is an integer from 3 to 250, from 5 to 180, from 6 to 140, from 8 to 70, from 9 to 40, or from 9 to 26.

(w) The composition according to Paragraphs (a) through (c), wherein for the second glyceride copolymer, $R^{11}$, $R^{12}$, and $R^{13}$ are each independently selected from the group consisting of pentadecyl, heptadecyl, 8-heptadecenyl, 8,11-heptadecadienyl, and 8,11,14-heptadecatrienyl.

(x) The composition according to Paragraphs (a) through (c) and (w), wherein for the second glyceride copolymer, two of $R^{21}$, $R^{22}$, and $R^{23}$ are independently selected from the group consisting of pentadecyl, heptadecyl, 8-heptadecenyl, 8,11-heptadecadienyl, and 8,11,14-heptadecatrienyl; and wherein one of $R^{21}$, $R^{22}$, and $R^{23}$ is selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in one aspect, one of $R^{21}$, $R^{22}$, and $R^{23}$ is selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(y) The composition according to Paragraphs (a) through (c) and (w), wherein for the second glyceride copolymer, one of $R^{21}$, $R^{22}$, and $R^{23}$ is selected from the group consisting of pentadecyl, heptadecyl, 8-heptadecenyl, 8,11-heptadecadienyl, and 8,11,14-heptadecatrienyl; and wherein two of $R^{21}$, $R^{22}$, and $R^{23}$ are independently selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in one aspect, two of $R^{21}$, $R^{22}$, and $R^{23}$ are independently selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.

(z) A composition comprising a glyceride copolymer, which comprises constitutional units formed from reacting:
  a) at least an unsaturated natural oil glyceride, and a unsaturated alkenylized natural oil glyceride in the presence of a metathesis catalyst;
  b) at least an unsaturated synthetic polyol ester, and a unsaturated alkenylized natural oil glyceride in the presence of a metathesis catalyst;
  c) at least an unsaturated natural oil glyceride, and a unsaturated alkenylized synthetic polyol ester in the presence of a metathesis catalyst;
  d) at least an unsaturated synthetic polyol ester, and a unsaturated alkenylized synthetic polyol ester in the presence of a metathesis catalyst;
  e) at least an unsaturated alkenylized synthetic polyol ester, and a unsaturated alkenylized synthetic polyol ester in the presence of a metathesis catalyst;
  f) at least an unsaturated alkenylized natural oil glyceride, and a unsaturated alkenylized natural oil glyceride in the presence of a metathesis catalyst;
  wherein the composition may be applied to at least one component of an absorbent article, wherein said absorbent article components are selected from the group consisting of a topsheet, a secondary topsheet, back sheet, barrier cuff, waist band, wing, and waist feature.

In one aspect, any of said glyceride copolymers comprises a $C_{10-14}$ unsaturated fatty acid ester.

In one aspect said catalyst is selected from the group consisting of an organo-ruthenium compound, an organo-osmium compound, an organo-tungsten compound, an organo-molybdenum compound and mixtures thereof;

In one aspect the unsaturated alkenylized natural oil glyceride is formed from the reaction of a unsaturated natural oil glyceride with a short-chain alkene in the presence of a metathesis catalyst, in one aspect, said catalyst is selected from the group consisting of an organo-ruthenium compound, an organo-osmium compound, an organo-tungsten compound, an organo-molybdenum compound and mixtures thereof, in one aspect, the short-chain alkene is selected from the group consisting of ethylene, propylene, 1-butene, 2-butene, isobutene, 1-pentene, 2-pentene, 1-hexene, 2-hexene, 3-hexene and mixtures thereof, in one aspect, the short-chain alkene is selected from the group consisting of ethylene, propylene, 1-butene, and 2-butene, and mixtures thereof, in one aspect, the unsaturated alkenylized natural oil glyceride has a lower molecular weight than the first unsaturated natural oil glyceride;

In one aspect, the unsaturated natural oil glyceride is obtained from a natural oil; in one aspect, from vegetable oil, animal fat, and/or algae oil; in one aspect, from Abyssinian oil, Almond Oil, Apricot Oil, Apricot Kernel oil, Argan oil, Avocado Oil, Babassu Oil, Baobab Oil, Black Cumin Oil, Black Currant Oil, Borage Oil, Camelina oil, Carinata oil, Canola oil, Castor oil, Cherry Kernel Oil, Coconut oil, Corn oil, Cottonseed oil, Echium Oil, Evening Primrose Oil, Flax Seed Oil, Grape Seed Oil, Grapefruit Seed Oil, Hazelnut Oil, Hemp Seed Oil, Jatropha oil, Jojoba Oil, Kukui Nut Oil, Linseed Oil, Macadamia Nut Oil, Meadowfoam Seed Oil, Moringa Oil, Neem Oil, Olive Oil, Palm Oil, Palm Kernel Oil, Peach Kernel Oil, Peanut Oil, Pecan Oil, Pennycress oil, Perilla Seed Oil, Pistachio Oil, Pomegranate Seed Oil, Pongamia oil, Pumpkin Seed Oil, Raspberry Oil, Red Palm Olein, Rice Bran Oil, Rosehip Oil, Safflower Oil, Seabuckthorn Fruit Oil, Sesame Seed Oil, Shea Olein, Sunflower Oil, Soybean Oil, Tonka Bean Oil, Tung Oil, Walnut Oil, Wheat Germ Oil, High Oleoyl Soybean Oil, High Oleoyl Sunflower Oil, High Oleoyl Safflower Oil, High Erucic Acid Rapeseed Oil, and mixtures thereof;

In one aspect, said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, for example, sucrose, and mixtures thereof In one aspect, the glyceride copolymer has a weight average molecular weight ranging from 4,000 g/mol to 150,000 g/mol, from 5,000 g/mol to 130,000 g/mol, from 6,000 g/mol to 100,000 g/mol, from 7,000 g/mol to 50,000 g/mol, from 8,000 g/mol to 30,000 g/mol, or from 8,000 g/mol to 20,000 g/mol.

(aa) The composition of Paragraph (z), wherein the short-chain alkene is ethylene (bb) The composition of Paragraph (z), wherein the short-chain alkene is propylene.

(cc) The composition of Paragraph (z), wherein the short-chain alkene is 1-butene.

(dd) The composition of Paragraph (z), wherein the short-chain alkene is 2-butene.

(ee) A composition according to Paragraphs (a) through (c) wherein the first glyceride copolymer is derived from a natural polyol ester and/or a synthetic polyol ester, in one aspect, said natural polyol ester is selected from the group consisting of a vegetable oil, a animal fat, a algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, for example, sucrose, and mixtures thereof.

(ff) A composition according to any of Paragraphs (a) through (ee), said composition comprising, based on total composition weight, from about 0.1% to about 50%, from about 0.5% to about 30%, or from about 1% to about 20% of a glyceride copolymer, selected from the group consisting of the first glyceride copolymer and the second glyceride copolymer, and mixtures thereof.

(gg) A composition according to any of Paragraphs (a) through (ff), comprising one or more of the following:
  a) from about 1% to about 90%, from about 5% to about 50%, or from about 10% to about 25% of an emollient or emollient system;
  b) from about 1% to about 50%, from about 5% to about 30%, or from about 10% to about 20% of a immobilizing (structuring) agent;
  c) from about 1% to about 50%, from about 1% to about 20%, or from about 2% to about 10% of a viscosity enhancer;
  d) from about 1% to about 50%, from about 1% to about 20%, or from about 2% to about 10% of a surfactant;
  e) from about 0.1% to about 90%, from about 0.1% to about 20%, or from about 1% to about 10% of a skin care ingredient;

f) from about 0.1% to about 30%, from about 0.1% to about 10%, or from about 0.1% to about 5% of an enzyme inhibitor;
g) from about 0.1% to about 10%, from about 0.1% to about 5%, or from about 0.1% to about 1% of a vitamin;
h) from about 1% to about 50%, from about 1% to about 20%, or from about 2% to about 10% of a moisturizer or humectant;
i) from about 0.01% to about 5%, from about 0.1% to about 2%, or from about 0.1% to about 1% of a perfume;
j) from about 0.02% to about 10%, from about 0.2% to about 5%, or from about 0.2% to about 2% of a perfume delivery system;
k) from about 1% to about 90%, from about 1% to about 50%, or from about 1% to about 25% of a skin aesthetics/skin feel ingredient; and
l) mixtures thereof.
(hh) A composition according to any of Paragraphs (a) through (gg), said composition comprising an emulsion, a gel network or lamellar phase, in one aspect, said composition comprises vesicles.
(ii) A composition according to any of Paragraphs (a) through (ii), wherein either of said first and second glyceride copolymers have a free hydrocarbon content, based on the weight of glyceride copolymer of from about 0% to about 5%, from about 0.1% to about 5%, from about 0.1% to about 4%, from about 0.1 to about 3%, or from about 0.1% to about 1%.
(jj) The composition according to any of Paragraphs (a) through (c) and (w), wherein for either of said first and second glyceride copolymers, $R^{21}$, $R^{22}$, and $R^{23}$ are each independently selected from the group consisting of: 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl; in one aspect, $R^{21}$, $R^{22}$, and $R^{23}$ are each independently selected from the group consisting of 8-nonenyl, 8-decenyl, 8-undecenyl, 8,11-dodecadienyl, 8,11-tridecadienyl, 8,11-tetradecadienyl, 8,11,14-pentadecatrienyl, 8,11,14-hexadecatrienyl, 12-tridecenyl, 12-tetradecenyl, and 12-pentadecenyl.
(kk) An absorbent article comprising a composition according to any of Paragraphs (a) through (jj), wherein the composition may be applied to at least one component of said absorbent article, wherein said absorbent article components are selected from the group consisting of a topsheet, a secondary topsheet, back sheet, barrier cuff, waist band, wing, and waist feature.

Consumer Product Adjunct Materials

The disclosed compositions may include additional adjunct ingredients that include: emollients, structuring agents, viscosity enhancers, surfactants, skin care ingredients, vitamins, moisturizers, perfumes, aesthetic ingredients, enzyme inhibitors, and combinations thereof.

Emollients

Emollients useful in the present invention can be petroleum-based, fatty acid ester type, alkyl ethoxylate type, fatty acid ester ethoxylates, fatty alcohol type, polysiloxane type, or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for lotion compositions of the present invention.

Suitable fatty acid ester type emollients include those derived from C14-C28 fatty acids, preferably C16-C22 saturated fatty acids, and short chain (C1-C8, preferably C1-C3) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols (C14-C28, preferably C14-C16) and shorter chain fatty acids e.g., lactic acid, such as lauryl lactate and cetyl lactate.

Suitable alkyl ethoxylate type emollients include C14-C22 fatty alcohol ethoxylates having an average degree of ethoxylation of 4 or less. Preferably, the fatty alcohol ethoxylate emollient is selected from the group consisting of lauryl, cetyl, and stearyl ethoxylates, and mixtures thereof, having an average degree of ethoxylation ranging from about of 4 or less. These alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4. For each of the compositions disclosed herein, having an average degree of ethoxylation of 4 or less enables the lotion of the present invention to exhibit a significant hydrophobicity, and typically exhibits an HLB of less than about 7. The hydrophobicity of the lotion is a property in delivering the benefit of cleaner skin and hair, i.e., less menses on the skin and hair or hair of the wearer.

Suitable fatty alcohol type emollients include C14-C22 fatty alcohols, preferably C16-C18 fatty alcohols. Representative examples include cetyl alcohol and stearyl alcohol, and mixtures thereof. These fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use in the present invention include polysiloxane compounds. In general suitable polysiloxane materials for use in the present invention include those having monomeric siloxane units of the following structure:

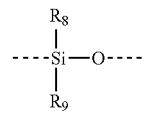

wherein, R1 and R2, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstantiated. R1 and R2 radicals of any particular monomeric unit may differ from the corresponding functionalities of the next adjoining monomeric unit. Additionally, the polysiloxane can be either a straight chain, a branched chain or have a cyclic structure. The radicals R1 and R2 can additionally independently be other silaceous functionalities such as, but not limited to siloxanes, polysiloxanes, silanes, and polysilanes. The radicals R1 and R2 may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes may vary as widely as the viscosity of polysiloxanes in general vary, so long as the polysiloxane is flowable or can be made to be flowable for application to the sanitary napkin topsheet. This includes, but is not limited to, viscosity as low as 5 centistokes (at 37 degrees C. as measured by a glass viscometer) to about 20,000,000 centistokes. Preferably the polysiloxanes have a viscosity at 37 degrees C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the sanitary napkin topsheets.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the lotion compositions of the present invention include phenyl-functional polymethylsiloxane compounds (e.g., Dow Corning 556 Cosmetic-Grade Fluid: polyphenylme-thylsiloxane) and cetyl or stearyl fictionalized dimethicones such as Dow 2502 and Dow 2503 polysiloxane fluids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Besides petroleum-based emollients, fatty acid ester emollients, fatty acid ester ethoxylates, alkyl ethoxylate emollients fatty alcohol emollients, and polysiloxanes, the emollients useful in the present invention can include minor amounts (e.g., up to about 10% of the total emollient) of other, conventional emollients. These other, conventional emollients include spermaceti or other waxes, fatty acids, and fatty alcohol ethers having from 14 to 28 carbon atoms in their fatty chain, such as stearic acid, propoxylated fatty alcohols; other fatty esters of polyhydroxy alcohols; lanolin and its derivatives. These other emollients should be included in a manner such that the solid or semisolid characteristics of the lotion composition are maintained.

The amount of emollient that can be included in the lotion composition will depend on a variety of factors, including the particular emollient involved, the lotion-like benefits desired, the other components in the lotion composition and like factors. The lotion composition can comprise from about 10 to about 95% of the emollient. Preferably, the lotion composition comprises from about 20 to about 80%, most preferably from about 40 to about 75%, of the emollient.

Immobilizing (Structuring) Agent

The immobilizing agent counteracts this tendency of the emollient to migrate or flow by keeping the emollient primarily localized on the surface of the sanitary napkin top sheet to which the lotion composition is applied. This is believed to be due, in part, to the fact that the immobilizing agent raises the melting point of the lotion composition above that of the emollient. Since the immobilizing agent is also miscible with the emollient (or solubilized in the emollient with the aid of an appropriate emulsifier), it entraps the emollient on the surface of the sanitary napkin topsheet as well.

It is also advantageous to "lock" the immobilizing agent on the surface of the sanitary napkin topsheet. This can be accomplished by using immobilizing agents which quickly crystallize (i.e., solidify) at the surface of the topsheet. In addition, outside cooling of the treated sanitary napkin topsheet via blowers, fans, etc. can speed up crystallization of the immobilizing agent.

In addition to being miscible with (or solubilized in) the emollient, the immobilizing agent needs to have a melting point of at least about 35 degrees C. This is so the immobilizing agent itself will not have a tendency to migrate or flow. Preferred immobilizing agents will have melting points of at least about 40 degrees C. Typically, the immobilizing agent will have a melting point in the range of from about 50 degrees to about 150 degrees C.

Suitable immobilizing agents for the present invention can comprise a member selected from the group consisting of C14-C22 fatty alcohols, C14-C22 fatty acids, and C14-C22 fatty alcohol ethoxylates having an average degree of ethoxylation of 4 or less, and mixtures thereof. Preferred immobilizing agents include C16-C18 fatty alcohols, most preferably selected from the group consisting of cetyl alcohol, stearyl alcohol, and mixtures thereof. Mixtures of cetyl alcohol and stearyl alcohol are particularly preferred. Other preferred immobilizing agents include C16-C18 fatty acids, most preferably selected from the group consisting of palmitic acid, stearic acid, and mixtures thereof. Mixtures of palmitic acid and stearic acid are particularly preferred. Still other preferred immobilizing agents include C16-C18 fatty alcohol ethoxylates having an average degree of ethoxylation for 4 or less. Preferably, the fatty alcohols, fatty acids and fatty alcohols are linear. Again, as noted above, having an average degree of ethoxylation of 4 or less enables the lotion of the present invention to exhibit significant hydrophobicity, and typically exhibits an HLB of less than about 7. The hydrophobicity of the lotion is a property in delivering the benefit of cleaner skin and hair, i.e., less menses on the skin and hair or hair of the wearer.

Other types of immobilizing agents can be used either alone or in combination with the fatty alcohols, fatty acids, and fatty alcohol ethoxylates described above. Examples of these other types of immobilizing agents includes polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin and hair sensitivity of those using sanitary napkin topsheets to which the lotion composition is applied, these esters and amides should also be relatively mild and non-irritating to the skin and hair.

Suitable polyhydroxy fatty acid esters for use in the present invention will have the formula:

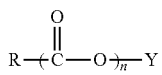

where in R is a C5-C31 hydrocarbyl group, preferably straight chain C7-C19 alkyl or alkenyl, more preferably straight chain C9-C17 alkyl or alkenyl, most preferably straight chain C11-C17 alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of C16-C22 saturated fatty acids. Because of the manner in which they are typically manufactured, these sorbitan esters usually comprise mixtures of mono-, di-, tri-o etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di- and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tet-raester) such as SPAN 60, and sorbitan stearates sold under the trade name GLYCOMUL-S by Lonza, Inc. Although these sorbitan esters typically contain mixtures of mono-, di- and trimesters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of C16-C22 saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid ester for use in the present invention comprise certain sucrose fatty acid esters, preferably the C14-C22 saturated fatty acid esters of sucrose. Sucrose monoesters and diesters are particularly preferred and include sucrose mono- and di-strearate and sucrose mono- and di-laurate.

Suitable polyhydroxy fatty acid amides for use in the present invention will have the formula:

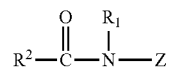

where-in R1 is H, C1-C4 hydrocarbyl, 2-hydroxyethyl, 2-hydroxypropyl, methoxyethyl, methoxypropyl or a mixture thereof, preferably C1-C4 alkyl, methoxyethyl or methoxypropyl, more preferably C1 or C2 alkyl or methoxypropyl, most preferably C1 alkyl (i.e., methyl) or methoxypropyl; and R2 is a C5-C31 hydrocarbyl group, preferably straight chain C7-C19 alkyl or alkenyl, more preferably straight chain C9-C17 alkyl or alkenyl, most preferably straight chain C1-C17 alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maitose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$-$CH_2OH$, —CH($CH_2OH$)—[(CHOH)$_{n-1}$]—$CH_2OH$, —$CH_2OH$—$CH_2$—(CHOH)$_2$(CHOR3)(CHOH)—$CH_2OH$, where n is an integer from 3 to 5, and R3 is H or a cyclic or aliphatic monosaccharide. Most preferred are the glycityls where n is 4, particularly —$CH_2$—(CHOH)$_4$-$CH_2OH$.

In the above formula, R1 can be, for example, N-methyl, N-ethyl, N-propyl, N-isopropyl, N-butyl, N-2-hydroxyethyl, N-methoxypropyl or N-2-hydroxypropyl, R2 can be selected to provide, for example, cocamides, stearamides, oleamides, lauramides, myristamides, capricamides, palmitamides, tallowamides, etc. The Z moiety can be 1-deoxyglucityl, 2-eoxyfructityl, 1-deoxymaltityl, 1-deoxy-lactityl, 1-deoxygalactityl, 1-deoxymannityl, 1-deoxymaltotriotityl.

Other types of ingredients that can be used as immobilizing agents, either alone, or in combination with the above-mentioned immobilizing agents, include waxes such as carnauba, beeswax, catidelilla, paraffin, ceresin, esparto, ouricuri, rezowax, and other known waxes. Preferably the wax is a paraffin wax. An example of a particularly preferred paraffin wax is Parrafin S. P. 434 from Strahl and Pitsch Inc. P.O. Box 1098 West Babylon, N.Y. 11704.

The amount of immobilizing agent that should be included in the lotion composition will depend on a variety of factors, including the particular emollient involved, the particular immobilizing agent involved, whether an emulsifier is required to solubilize the immobilizing agent in the emollient, the other components in the lotion composition and like factors. The lotion composition can comprise from about 5 to about 90% of the immobilizing agent. Preferably, the lotion composition comprises from about 5 to about 50%, most preferably from about 10 to about 40%, of the immobilizing agent.

Viscosity Enhancers

In addition to the components already described, the compositions of the invention may further include from about 0.1 to about 40 percent by weight of one or more compounds acting as viscosity enhancers that increase the meltpoint viscosity of the emollients of the composition. More specifically, the compositions include from about 5 to about 20 percent by weight of one or more viscosity enhancers. Even more specifically, the compositions include from about 10 to about 15 percent by weight of viscosity enhancer(s). The viscosity enhancer increases the meltpoint viscosity of the compositions to have a high viscosity under low shear and at the "hot box car" stability temperature of approximately 54.5° C. Having high viscosity (>50,000 centipoise) at elevated temperatures prevents the compositions from migrating into or away from the materials to which they are applied. However, the viscosity enhancer component also provides a low viscosity (<5,000 centipoise) for the compositions under high shear and at processing temperatures. The viscosity enhancers of the invention are capable of providing a desirable viscosity, depending on shear and temperature conditions, for compositions having a range of melting points. While it is desirable for compositions of the invention to have increased viscosity under "hot box car" stability conditions, the increased viscosity can be maintained, in part, through the use of one or more viscosity enhancers up to the melting point of the particular composition. Typically, process temperatures are approximately 5° C. above the melting point of the composition. Examples of suitable viscosity enhancers include polyolefin resins, lipophilic/oil thickeners, ethylene/vinyl acetate copolymers, organically modified clays, polyethylene, silica, silica silylate, silica methyl silylate, colloidal silicone dioxide, alkyl hydroxy ethyl cellulose, other organically modified celluloses, PVP/decane copolymer, PVM/MA decadiene crosspolymer, PVP/eicosene copolymer, PVP/hexadecane copolymer, microcrystalline wax, hexadecyl-cosanyl-hexacosanate, shellac wax, glycol montanate, PEG-12 carnauba, synthetic paraffin, ozokerite, C20-C40 alkyl hydroxystearyl stearate, polyperfluoromethylisopropylether montan wax and mixtures of these compounds. Many of the solidifying agents, also described herein, have been found to provide the same benefits to the compositions of the invention as the viscosity enhancers.

The viscosity enhancers are selected to influence the rheological properties of the compositions. For example, one or more viscosity enhancers can be selected so that the composition has a viscosity of greater than about 50,000 centipoise at temperatures of about 55° C. and lower under low shear. Additionally, one or more viscosity enhancers can be selected so that the composition has a viscosity less than about 5,000 centipoise at temperatures of about 60° C. and higher under shear for processing conditions.

Surfactants

As mentioned above, it is highly desirable that the article topsheet is made of a hydrophilic material to promote rapid transfer of liquids (e.g., urine) through the topsheet. Similarly, it is important that the lotion composition also be sufficiently wettable to ensure that liquids will transfer through the topsheet more rapidly. This diminishes the likelihood that body exudates will flow off the lotion coating rather than being drawn through the topsheet and being absorbed by the absorbent core. Depending upon the particular immobilizing agent used in the lotion composition of the present invention, an additional hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$-$C_{18}$ fatty alcohols having HLB values below about 7 will require addition of hydrophilic surfactant to improve wettability when the lotion composition is applied to article topsheets. Similarly, a hydrophobic emollient such as petrolatum will require the addition of a hydrophilic surfactant.

Suitable hydrophilic surfactants will be miscible with the emollient and the immobilizing agent so as to form homogeneous mixtures. Because of possible skin sensitivity of those using disposable absorbent products to which the lotion composition is applied, these surfactants should also be relatively mild and non-irritating to the skin. Typically, these hydrophilic surfactants are nonionic to be not only non-irritating to the skin, but also to avoid other undesirable effects on any underlying tissue laminate structure, e.g., reductions in tensile strength.

Suitable nonionic surfactants may be substantially non-migratory after the lotion composition is applied to the article topsheets and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in lotion compositions of the present invention include alkylglycosides; alkylglycoside ethers as described in U.S. Pat. No. 4,011,389 (Langdon, et al), issued Mar. 8, 1977; alkylpolyethoxylated esters such as Pegosperse 1000MS (available from Lonza, Inc., Fair Lawn, N.J.), ethoxylated sorbitan mono-, di- and/or tri-esters of $C_{12}$-$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$-$C_{15}$ linear alcohols with 9 moles of ethylene oxide), marketed by Union Carbide Corporation; KYRO EOB (condensation product of $C_{13}$-$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$-$C_{15}$ linear alcohols with 12 moles of ethylene oxide) and NEODOL 23-6.5T (condensation product of $C_{12}$-$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the present invention includes Aerosol OT, a dioctyl ester of sodium sulfosuccinic acid marketed by American Cyanamid Company.

Still another type of suitable surfactant for use in the present invention includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the lotion composition.

The amount of hydrophilic surfactant required to increase the wettability of the lotion composition to a desired level will depend upon the HLB value and level of immobilizing agent used, the HLB value of the surfactant used and like factors. The lotion composition can comprise from about 1 to about 50% of the hydrophilic surfactant when needed to increase the wettability properties of the composition. Preferably, the lotion composition comprises from about 1 to about 25%, most preferably from about 10 to about 20%, of the hydrophilic surfactant when needed to increase wettability.

Skin Care Ingredients

Various skin care ingredients that may be incorporated into the skin care compositions provide various skin benefits, such as reduction in redness, improvement in skin appearance and/or condition, formation of a barrier or protective layer, or reduction of irritants in body wastes. A host of skin care ingredients can be incorporated into a carrier and applied to the skin. These skin care ingredients include, but are not limited to, barrier substances (petrolatum), skin conditioning agents (oil, lanolin), proton donating agents, protease and/or enzyme inhibitors, and antimicrobials. The skin care composition may also contain humectants (glycerine, sorbitol), vitamins, skin soothing agents, such as aloe vera, or other ingredients from herbal, botanical or mineral sources, or multi-functional agents, such as zinc oxide.

A wide variety of topically effective ingredients can be incorporated into the stable composition. Such skin care ingredient provides visible benefits to the occluded skin under an absorbent article when applied. The skin care ingredients can be uniformly dispersed throughout the composition as insoluble particulates. Alternatively, the skin care ingredients can be solubilized in the substantially anhydrous carrier. The resultant composition is substantially stable (i.e., resistant to excessively large agglomeration, stratification and/or settling), has a solid or semi-solid consistency at room temperature that renders it readily transferable to the skin, and is suitable for topical application to the skin via a delivery vehicle such as an absorbent article or elements thereof.

Numerous materials that have been deemed safe and effective skin care ingredients are logical materials for use herein. Such materials include Category I and Category III actives as defined by the U.S. Food and Drug Administration's (FDA) Tentative Final Monograph on Skin Protectant Drug Products for Over-the-Counter Human Use (21 C.F.R. § 347). It will be recognized that several of the monographed actives listed below are "emollients" as defined herein. Category I actives presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Category III actives presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like. These monographed materials are known to provide multiple skin benefits, such as skin protectant, itch prevention, irritation prevention, via various mechanisms.

The skin care ingredients may also include, but are not limited to, pH control agents or proton donating agents, such as pH buffer systems, ammonium-neutralizing agents, organic acids, polymeric acids, inorganic acids, and their salts, anti-microbials; enzyme inhibitors, protease inhibitors, anti-coenzymes; chelating agents; and anti-bodies. Some nonlimiting examples of proton donating agents are described in U.S. application Ser. No. 09/041,509, by McOsker et al. filed on Mar. 12, 1998.

Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases. Some non-limiting examples of such protease inhibitors are described in U.S. application Ser. No. 09/041,232, by Rourke et al filed on Mar. 12, 1998, U.S. Pat. No. 5,091,193 issued to Enjolras et al, on Feb. 25, 1992, and U.S. Pat. No. 4,556,560 issued to Buckingham on Dec. 3, 1985, all are incorporated by reference herein.

Enzyme inhibitors are designed to inhibit specific enzymatic activities of various classes of proteases. Specifically useful for the present invention are inhibitors that interact with those proteolytic and lipolytic enzymes commonly present in feces, such as lipases, esterases, diesterases, ureases, amylases, elastases, nucleases. The enzyme inhibitors suitable for use in the present invention include, but are not limited to, chelating agents which bind to metal cofactors of specific enzymes, antibodies raised for specific enzymes, enzyme inhibitors for various enzymes or coenzymes, preferably of the proteolytic type, such as trypsin, chymotrypsin, aminopeptidase and elastase, serine, cysteine, lipases, bile salts (acting as coenzymes that enhance the activities of lipases), amylases, and/or ureases. Other enzyme inhibitors known to effectively reduce or interfere with enzyme activities are also contemplated to be within the scope of the present invention. Some non-limiting examples of such enzyme inhibitors are described in U.S.

application Ser. No. 09/041,266, by Roe et al. and U.S. application Ser. No. 09/041,196, by Underiner et al., both filed on Mar. 12, 1998, U.S. Pat. No. 5,376,655 issued to Imaki et al. on Dec. 27, 1994. U.S. Pat. No. 5,091,193 issued to Enjolras et al. on Feb. 25, 1992, U.S. Pat. No. 3,935,862 issued to Kraskin on Feb. 3, 1976, U.S. Pat. No. 5,409,903 issued to Polak et al. on Apr. 25, 1995, U.S. Pat. No. 4,556,560 issued to Buckingham on Dec. 3, 1985, Patent Application EP 97/120,699 and EP 97/120,700 both by Polumbo et al. and filed on Nov. 26, 1997, all are incorporated by reference herein.

The skin care ingredients in the present invention should preferably include at least one of the following: zinc oxide, talc, starch, allantoin, hexamidine and its salts and derivatives, hexamidine diisethionate, and its salts, triacetin, phytic acid, ethylenediamine tetraacetic acid (EDTA), and 4-(2-aminoethyl)-benzenesulfonylfluoride hydrochloride, chitosan, and mixtures thereof.

Generally, a safe and effective amount of a skin care ingredient is incorporated into the composition. The skin care compositions suitable for the present invention may contain skin care ingredients in a concentration of from about 0.001% to about 70% by weight, preferably from about 0.01% to about 45%, more preferably from about 0.1% to about 25%, and most preferably from about 0.1% to about 10%. The skin care ingredients may be used singly or as a mixture of skin care ingredients in a "cocktail". Because of the variety of skin care ingredients that may be used in the present invention, the effective concentration of each skin care ingredient should be separately determined, as known to those skilled in the art.

Where the ingredients are insoluble in the composition, the average particle size of the ingredients plays an important role in suspending the particles in the composition without substantial agglomeration, stratification and/or settling. The particles should be substantially free of excessively large agglomerates, i.e., there is negligible amount of particles larger than 1000 microns. The average particle size of the skin care ingredients should preferably be less than about 1000 microns, more preferably less than about 100 microns, and most preferably less than about 50 microns.

It is generally known that solid particles in neat form tend to form dumps or agglomerates, bound by static charges, interactions between functional groups, etc. It is often necessary to break up the clumps in order to disperse the particles, to reduce the settling effect, and to deliver skin benefits effectively. The break-up and dispersion can be accomplished by grinding or milling, by incorporation into a composition with agitation, by predispersing in a dispersant mixture, by predissolving in a carrier or by other methods known to persons skilled in the art.

The predispersant mixture preferably comprises a dispersant fluid and optionally, a wetting agent. The wetting agent is typically a surfactant having a hydrophilic end, which interacts with the functional groups on the surface of the ingredient particles, and a lipophilic end, which is compatible with the oil-based carrier of the present composition. Without intending to be bound by theory, it is believed that the wetting agent, along with external forces applied such as shear, agitation), facilitates the break-up of the clumps of the skin care ingredients and the mixing or dispersion of the particulate ingredients in the composition. It is also believed that the wetting agent, being a hydrophilic-lipophilic, surfactant-type material, bridges the interfaces between the particulate ingredients and the substantially anhydrous carrier. It is also believed that the dispersant fluid can serve as a diluent and/or a wetting agent for predispersing the particles. Additionally, the dispersant fluid preferably is miscible with the substantially anhydrous, oleaginous composition of the present invention. Nonlimiting examples of the dispersant fluid include mineral oil, dimethicone and other silicones, esters, preferably the condensation products a $C_1$-$C_2$, alcohols with $C_1$-$C_{22}$ acids. The predispersion preferably has a high solid or particle content in the range of 50% to 99% by weight solids, more preferably from 60% to 90% by weight solids, and most preferably from 70% to 80% by weight solids. Various grinding and/or milling techniques known in the art are sometimes used in the predispersing process to break down the particle size and disperse the particles.

In a preferred embodiment, the ingredient is zinc oxide dispersed, as insoluble particles, in the oleaginous, substantially anhydrous carrier of the present invention. More preferably, the zinc oxide particles are prepared as a predispersion. The skin care composition comprises from about 1 wt % to about 70 wt % of the zinc oxide predispersion, preferably from about 3 wt % to about 50 wt %, more preferably from about 5 wt % to about 30 wt %. The predispersion has preferably from about 90 wt % to about 50 wt % zinc oxide, from about 1 wt % to about 50 wt % dispersant fluid and from about 0.1 wt % to about 10 wt % wetting agent. A preferred embodiment comprises about 75 wt % zinc oxide particles dispersed in about 22 wt % of a dispersant fluid such as those described above and about 3 wt % of a polyglyceyl ester wetting agent. Suitable zinc oxide predispersion is available from Kobo Products, Inc., S. Plainfield, N.J. The zinc oxide pard cies of the present invention typically consist of agglomerates of primary particles. The particle size of the agglomerates ranges from about 0.1 to about 300 microns and the average agglomerate size is about 1.0 microns. The average particle size of the primary particles is about 0.12 microns. Typically the agglomerate comprises about 5 to about 8 primary particles.

Alternatively, a hydrophobic modification can be applied to the zinc oxide particles to "wet" the surface of the particles. In this process, surfactants are actually attached to the surface of the zinc oxide particles under high temperature or pressure. The modified or "wetted" zinc oxide particles with the lipophilic ends of the surfactants extending from their surfaces, become at least partially miscible in the oil-based carrier of the present compositions.

Additional skin care compositions may comprise panthenol triacetate (a derivative of vitamin B5), niacin, and hexamidine/hexamidine derivatives.

The skin care compositions may comprise hexamidine skin treatment, agent at concentrations ranging from about 0.001% to about 0.1% from about 0.005% to about 0.1%, or even from about 0.01% to about 0.1% by weight of the composition. The hexamidine skin treatment agents suitable for use herein include armatic diamines such as 4,4'-[1,6-Hexanediylbis(oxy)]bisbenzenecarboximidamide; 4,4'-(hexamethylenedioxy)dibenzamidine; and 4,4'-diamidino-α,ω-diphenoxyhexane. The most popular employed form of hexamidine is the general category of hexmidine salts, which include acetate, salicylate, lactate, gluconate, tartarate, citrate, phosphate, borate, nitrate, sulfate, and hydrochloride salts of hexamidine. Specific nonlimiting examples of hexamidine salts include hexamidine isethionate, hexamidine diisethionate, hexamidine hydrochloride, hexamidine gluconate, and mixtures thereof. Hexamidine isethionate and hexamidine diisethionate are β-hydroxyethane sulfonate salts of hexamidine which are preferred for use herein as a skin treatment agent in the prevention and/or treatment of skin disorders. Hexamidine diisethionate is the most preferred hexamidine compound suitable for use as the skin treatment agent herein and is available from Laboratories Serolobilogiques (Pulnoy, France) and the Cognis Incorporation (Cincinnati, Ohio) under the tradename ELASTAB HP100.

Hexamidine compounds are known as effective skin treatment agents that can control microbial growth that can lead to irritating and itching skin disorders. Therefore, these skin treatment agents are often referred to as antimicrobial agents. As used herein the term "antimicrobial agents" refer to materials which function to destroy or suppress the growth or metabolism of microbes, and include the general classification of antibacterial, antifungal, antiprotozoal, antiparasitic, and antiviral agents.

It has been found, however, that a low concentration (about 0.1% or less by weight) of hexamidine provides for improved reduction and/or prevention of skin irritating infections, especially when a low amount of hexamidine is combined with a low concentration of other antimicrobial agents such as zinc oxide and/or niacinamide. This combination of hexamidine and zinc oxide and/or niacinamide can be administered topically and internally at a total concentration less than an effective amount of an applied dosage of these individual compounds. As used herein the term "effective amount" refers to an amount with provides a therapeutic benefit with minimal or no adverse reaction in the reduction and/or prevention of any noticeable or unacceptable skin abnormality which causes irritating, acute, or chronic symptoms including itching and inflammation.

Other aromatic diamines are also suitable for use as a skin treatment agent herein. Such compounds include butamidine and derivatives thereof including butamidine isethionate; pentamidine and derivatives thereof including pentamidine isethionate and pentamidine hydrochloride; dibromopropamidine and derivatives thereof including dibromopropamidine isethionate; stilbamidine and derivatives thereof including hydroxystilbamidine, stilbamidine dihydrochloride, and stilbamidine isethionate: diaminodiamidines and derivatives thereof; and mixtures thereof.

Enzyme Inhibitors

Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carhoxypepidases, dipeptidases and aminopepidases. Some non-limiting examples of such protease inhibitors are described in U.S. application Ser. No. 09/041,232, by Rourke et al filed on Mar. 12, 1998, U.S. Pat. No. 5,091193 issued to Enjolras et al, on Feb. 25, 1992, and U.S. Pat. No. 4,556,560 issued to Buckingham on Dec. 3. 1985, all are incorporated by reference herein.

Enzyme inhibitors are designed to inhibit specific enzymatic activities of various classes of proteases. Specifically useful for the present invention are inhibitors that interact with those proteolytic and lipolytic enzymes commonly present in feces, such as lipases, esterases, diesterases, ureases, amylases, elastases, nucleases. The enzyme inhibitors suitable for use in the present invention include, but are not limited to, chelating agents which bind to metal cofactors of specific enzymes, antibodies raised for specific enzymes, enzyme inhibitors for various enzymes or coenzymes, preferably of the proteolytic type, such as trypsin, chymotrypsin, aminopeptidase and elastase, serine, cysteine, lipases, bile salts (acting as coenzymes that enhance the activities of lipases), amylases, and/or ureases. Other enzyme inhibitors known to effectively reduce or interfere with enzyme activities are also contemplated to be within the scope of the present invention. Some non-limiting examples of such enzyme inhibitors are described in U.S. application Ser. No. 09/041,266, by Roe et al. and U.S. application Ser. No. 09/041,196, by Underiner et al., both filed on Mar. 12, 1998, U.S. Pat. No. 5,376,655 issued to Imaki et al. on Dec. 27, 1994, U.S. Pat. No. 5,091,193 issued to Enjolras et al. on Feb. 25, 1992 U.S. Pat. No. 3,935,862 issued to Kraskin on Feb. 3, 1976, U.S. Pat. No. 5,409,903 issued to Polak et al. on Apr. 25, 1995, U.S. Pat. No. 4,556,560 issued to Buckingham on Dec. 3, 1985, Patent Application EP 97/120,699 and EP 97/120,700 both by Polumbo et al. and filed on Nov. 26, 1997, all are incorporated by reference herein. Protease is a common term employed to represent a group of proteolytic enzymes that are capable of splitting proteins and peptides into fragments by cleaving or hydrolyzing peptide bonds. Proteases can be subclassified into proteinases (endopeptidases) and the peptidases (exopeptidases). Peptidases act on peptide bonds adjacent to a free amino or carboxyl group on the end of a protein and thus cleave the protein from the outside. Among the principal types of peptidases are carboxypeptidases, dipeptidases and aminopeptidases. Proteinases act on specific; interior peptide bonds of proteins and can be subclassified into four kinds, i.e. serine proteases, metalloproteases, cysteine proteases, and aspartyl proteases. Among the principal types of proteinases are trypsin and chymotrypsin. Because proteases are widely distributed in plants, molds, bacteria, milk, milk products, and almost all animal tissues, as well as in digestive juices in the gastrointestinal tract, they are almost always present in the diapered area when it has been soiled by human waste. Each of the protease inhibitors included in the absorbent articles of the invention is a chemical substance which meets at least one of the seven criteria for $IC_{50}$ described above and reversibly or irreversibly inhibits the hydrolytic action of one or more proteases included among the foregoing functional subclasses of proteases normally found in human feces as well as among proteases whose substrate specificity is as yet undefined.

Protease inhibitors that may be employed in the embodiments of the invention include any naturally occurring inhibitor of plant, microbial and/or animal origin (including human), and synthetically manufactured chemical inhibitor that meets the criteria for $IC_{50}$ described above. Exemplary protease inhibitors that are believed to meet the $IC_{50}$ criteria and are further believed to inhibit the type of protease indicated in parentheses include, but are not limited to, soybean trypsin inhibitor and other plant-derived trypsin inhibitors such as lima bean protease inhibitor, corn protease inhibitor and the like; Bowman Birk inhibitor (serine, trypsin-like protease inhibitor); pancreatic trypsin inhibitor such as bovine pancreatic basic trypsin inhibitor and other animal-derived pancreatic trypsin inhibitors; egg white trypsin inhibitor (serine, trypsin-like protease inhibitor); ovomucoids containing ovoinhibitors such as from chicken or turkey egg white (trypsin and chymotrypsin inhibitors); chymostatin (serine, chymotrypsin-like protease inhibitor); aprotinin (serine protease inhibitor); leupeptin and its analogs such as propionyl -leupeptin, N-α-t-BOC-deacetylleupeptin (serine and cysteine protease inhibitor), bestatin and its analogs such as epibestatin and nitrobestatin (aminopeptidase metalloprotease inhibitor); amastatin and its analogs such as epiamastatin (aminopeptidase inhibitor); antipain (trypsin inhibitor); antithrombin III (serine protease inhibitor); 4-sulfamoylphenyl-4-guanidinobenzoate methanesulfonate (trypsin inhibitor); camostat (trypsin inhibitor); elafin (elastase inhibitor); hirudin (thrombin-like serine protease inhibitor); cystatin (egg white cysteine protease inhibitor); E-64 (trans-epoxysuccinyl-L-leucylamido-(4-guanidino)butane) and its analogs (cysteine protease inhibitor); $\alpha_2$-macroglobulin (universal endoprotease inhibitor); $\alpha_1$-antitypsin (trypsin inhibitor); pepstatin and its analogs such as acetyl pepstatin, pepstatin A, Nle-Sta-Ala-Sta (aspartyl protease inhibitor); apstatin (aminopeptidase P inhibitor); (2R)-2-mercaptomethyl-4-methylpentanoyl-b-(2-naphthyl)-Ala-Ala amide (matrix metalloprotease inhibitor); (2R)-2-mercaptomethyl-4-methylpentanoyl-Phe-Ala amide (matrix metalloprotease inhibitor); N-acetyl-Leu-Leu-methioninal (calpain inhibitor); N-acetyl-Leu-Leu-norleucinal (calpain inhibitor); p-aminobenzoyl-Gly-Pro-D-Leu-D-Ala hydroxamic add (matrix metalloprotease inhibitor); 2(R)-[N-(4-methoxyphenylsulfonyl)-N-(3-pyridylmethyl)amino]-3-methylbutano-hydroxamic acid (metalloprotease inhibitor); 4-(2-aminoethyl)-benzenesulfonylfluoride hydrochloride (broad spectrum/general protease inhibitor); and mixtures of any of the foregoing.

Among preferred protease inhibitors for use in the absorbent articles of the invention are compounds that exhibit inhibitory activity that is not necessarily restricted to a single class of proteases. Such compounds include, but are not limited to, hexamidine and its salts; pentamidine and its salts; benzamidine and its salts and derivatives, p-aminobenzamidine and its salts and derivatives; and guanidinobenzoic acid and its salts and derivatives such as those disclosed in U.S. Pat. No. 5,376,655 issued to Imaki et al. on Dec. 27, 1994, the disclosure of which is hereby incorporated by reference. Other preferred protease inhibitors include polymer derivatives of guanidinobenzoic acid disclosed and made in our co-pending U.S. patent application Ser. No. 09/041,196, filed Mar. 12, 1998 in the name of T. L. Underiner et al, co-filed with the present application, the disclosure of which co-pending application is hereby incorporated by reference.

The protease inhibitors may be employed singly or as a mixture of protease inhibitors such as a "cocktail" of inhibitors in a single absorbent article. Moreover, different protease inhibitors may be employed in different locations in a single absorbent article.

Because of the wide diversity of enzymes present in feces, it is reasonably predictable that materials such as those described above which inhibit fecal proteases may also inhibit enzymes that cleave substrates other than proteins and peptides. Hence protease inhibitors which also inhibit lipases and other esterases, amylases, and/or ureases are within the scope of the embodiments of the invention if the inhibitor meets the $IC_{50}$ criteria for protease inhibitory activity as described above.

Protease inhibitors that are preferred in the practice of the invention are soybean trypsin inhibitor, Bowman-Birk inhibitor, aprotinin, hexamidine (e.g., hexamidine diisethionate), p-aminobenzamidine, leupeptin, pepstatin A, chymostatin and polymer derivatives of guanidinobenzoic acid (disclosed and made in our copending U.S. patent application Ser. No. 09/041,196, incorporated by reference above. Particularly preferred protease inhibitors are soybean trypsin inhibitor, hexamidine, p-aminobenzamidine and the foregoing polymer derivatives of guanidinobenzoic.
Vitamins Various vitamins may be incorporated into the skin care compositions and lotions, including, but not limited to, Vitamin A and derivatives, Vitamin B derivatives (panthenol, niacinamide), Vitamin C and derivatives, Vitamin D and derivatives, and Vitamin E and derivatives.
Moisturizers/Humectants Depending on the skin condition to be treated, humectants may be included in the skin care compositions. Humectant is a type of moisturizing emollient which attracts moisture from the surrounding atmosphere and enhance water absorption of the stratum corneum (i.e., the outer, corny layer of the skin). Nonlimiting examples of humectants useful herein include glycerin; C2-C6 glycols, such as ethylene glycol, propylene glycol, butylene glycol, hexalene glycol; polyethylene glycols (PEGs), such as PEG-2, PEG-3, PEG-30, and PEG-50; polypropylene glycols (PPGs), such as PPG-9, PPG-12, PPG-15, PPG-17, PPG-20, PPG-26, PPG-30, and PPG-34; glycolic esters and ethers, such as C4-C20 alkylether of PEG or PPG, C1-C20 carboxylic acid esters of PEG or PPG, di-C8-C30 alkyl ethers of PEG or PPG; sorbitols and sorbitol esters, trihydroxystearin; polyhydric alcohols; other ethoxylated derivatives of lipids; and the like.
Perfumes/Fragrances The perfumes and compositions of this invention are the conventional ones known in the art. Selection of any perfume component, or amount of perfume, is based on functional and aesthetic considerations. Preferred perfume components useful in the present invention are the highly volatile, and the moderately volatile perfume ingredients, more preferably the highly volatile, low boiling perfumes.

The highly volatile, low boiling, perfume ingredients typically have boiling points of about 250° C. or lower. These highly volatile perfumes are fleeting and are quickly lost as they are released. Many of the more moderately volatile perfume ingredients are also quickly lost. The moderately volatile perfume ingredients are those having boiling points of from about 250° C. to about 300° C. Many of the perfume ingredients as discussed hereinafter, along with their odor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, neral, acetate, nonyl acetate, phenyl ethyl alcohol, alpha-pinene, beta-pinene, gamma-terpinene, alpha-terpineol, beta-terpineol, terpinyl acetate, and vertenex (para-tertiarybutyl) cyclohexyl acetate). Some natural oils also contain large percentages of highly volatile perfume ingredients. For example, lavandin contains as major components: linalool; linalyl acetate; geraniol; and citronellol, Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, for acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Other odor controlling organic compounds which can be used herein include particular other fragrance/masking/reacting components selected from the lists (c), (d) and (e).

Components from list (c) are menthol, menthyl acetate, menthyl lactate, menthyl propionate, menthyl butyrrate, menthone, mint terpenes, laevo-carvone, Cis-3-Hexenol & Cis-3-Hexenyl acetate, koavone, methyl dioxolan, ethylene brassylate, and salycilate esters. Salycilate esters are preferably selected from amyl salicylate, isoamyl salicylate, isobutyl salicylate, cis-3-hexenyl salicylate, hexyl salicylate, cyclohexyl salicylate, benzyl salicylate, phenylethyl salicylate, propyl salicylate, isopropyl salicylate or mixtures thereof.

These are all compounds which primary function is to mask malodors. This may occur through vapor pressure suppression of the malodor or by overwhelming the unpleasant malodor with the pleasant odor of the fragrance component. These materials, when used, may significantly reduce the ability to detect the malodors. The masking ability to hide malodors is possible due to the volatile nature of the materials selected, which are released from the complex in the absorbent article and are then inhaled into the nose of a consumer, generally within somewhat close range of the absorbent article, e.g. within about 0 to 10 meters of the article by normal breathing (although this should in no way be intended to limit the scope of the invention).

Components from list (d) are methyl-dihydrojasmonate, methyl jasmonate, eucalyptol, tetrahydro-linalool, phenylethyl alcohol, hexyl iso-butyrate, linalyl acetate, benzyl acetate, Benzyl alcohol, or mixture thereof. These are volatile materials which are well complexed with cyclodextrin and are released very quickly upon contact with a water based liquid. Their presence allows the absorbent article to respond even more quickly to an insult of malodorant liquid by releasing a compound that have a good general masking effect against malodors, in particular, being very volatile, reduces the vapor pressure of other malodorant compounds slowing down their evaporation rate.

List (e) includes other malodor masking and fragrance components which can be used as odor controlling organic compounds in the present invention:

e) camphor, p-menthane, limonene, cresol, linalool, myrcenol, tetra hydromyrcenol, di-hydromyrcenol, myrcene, citronellol, citronellyil derivatives, geraniol, geranyl derivatives, mugetanol, eugenol, jasmal, terpineol, pinanol, cedrene, damascone, beta pinene, cineole and its derivatives, nonadienol, ethylhexanal, octanol acetate, methyl furfural, terpinene, thujene, amylacetate, camphene, citronellal, hydroxycitronellal, ethyl maltol, methyl phenyl carbinyl acetate, dihydrocumarin, di-hydromyrcenyl acetate, geraniol, geranial, isoamylacetate, ethyl, and/or triethyl acetate, para-cresol, para-cymene, methyl abietate, hexyl-2-methyl butyrate, hexyl-2-methyl butyrate, and mixtures thereof.

The optional perfume component may comprise a component selected from the group consisting of (1) a perfume microcapsule, or a moisture-activated perfume microcapsule, comprising a perfume carrier and an encapsulated perfume composition, wherein said perfume carrier may be selected from the group consisting of cyclodextrins, starch microcapsules, porous carrier microcapsules, and mixtures thereof and wherein said encapsulated perfume composition may comprise low volatile perfume ingredients, high volatile perfume ingredients, and mixtures thereof;

(2) a pro-perfume;

(3) a low odor detection threshold perfume ingredients, wherein said low odor detection threshold perfume ingredients may comprise less than about 25%, by weight of the total neat perfume composition; and (4) mixtures thereof; and Porous Carrier Microcapsule—A portion of the perfume composition can also be absorbed onto and/or into a porous carrier, such as zeolites or clays, to form perfume porous carrier microcapsules in order to reduce the amount of free perfume in the multiple use fabric conditioning composition.

Pro-perfume—The perfume composition may additionally include a pro-perfume. Pro-perfumes may comprise nonvolatile materials that release or convert to a perfume material as a result of, e.g., simple hydrolysis, or may be pH-change-triggered pro-perfumes (e.g. triggered by a pH drop) or may be enzymatically releasable pro-perfumes, or light-triggered pro-perfumes. The pro-perfumes may exhibit varying release rates depending upon the pro-perfume chosen.

Skin Aesthetics/Skin Feel

Silk protein is composed of silk fiber and sericin. The silk protein is produced by species of the Phylum Arthropoda, classes Insecta and Arachnida. Sericin and/or silk amino acids and/or silk peptides are amenable to binding to the skin and hair, forming a resistant, moisturizing, and protective film on the skin/hair. The optional silk ingredient also provides for body benefits such as soothing, moisturizing, and conditioning. The lotion compositions may comprise the preferred optional silk protein or silk amino acids, or mixtures thereof at concentrations ranging from about 0.0001% to about 25% or from about 0.0005% to about 15% or from about 0.001% to about 10% by weight of the lotion.

In one embodiment, the lotion composition may comprise inorganic particles, including alumina silicates, silicates, silicas, mica and/or talc. Clays may also be used. However, in the present invention it may be preferred that the particulate material is an organic material. Preferably, the particles are a non-active and/or non-reactive material. The particles may be porous, or non-porous. The particles may have any shape, but preferably they have a smooth surface, and they may be preferably spherical or plate-like particles. The particles may comprise a coating agent on their surface or part thereof, for example a surfactant to change its properties, e.g. hydrophilicity. The particles, in particular when they are oleofinic, may include a melt-additive, which is added during the manufacturing of the particles.

Suitable materials include but are not limited to: polystyrene particles, polypropylene and/or polyethylene (co)polymer particles, polytetratiuoroethylene particles, polymethylsilses-quioxane particles, nylon particles. Suitable commercially available particulate materials include but are not limited to: polyethylene particles, available from Honeywell International of Morristown, N.J. under the trade name ACUMIST; polymethyl methacrylate particles (microspheres), available from KOBO of South Plainfield, N.J. as BPA; lactone cross polymer particles (microspheres), available from KOBO as BPD; nylon 12 particles (microspheres), available from KOBO as NYLON SP; polymethylsilsesquioxane particles (microspheres), available from KOBO as TOSPEARL; cellulose particles (microspheres), available from KOBO as CELLO-BEADS; polytetrafluoroethylene powders, available from Micro Powders, Inc. of Tarrytown, N.Y. as MICROSLIP; blends of natural wax and micronized polymers as are available from Micro Powders as MICROCARE and particles of a copolymer of vinylidene chloride, acrylonitrile and methylmethacrylate available as EXPANCEL from Expancel, Inc. of Duluth, Ga. Micronized waxes, such as are available from Micro Powders as MICROEASE may also be incorporated. Preferred are polyolefin particles (powders) as are available from Equistar Chemical Corp. Houston, Tex. as MICROTHENE. Particularly preferred is MICROTHENE FN510-00 from Equistar.

Methods of Making Compositions

The compositions of the present invention can be formulated into any suitable form and prepared by any process chosen by the formulator. For example, the glyceride copolymers can be combined directly with the composition's other ingredients without pre-emulsification and/or pre-mixing to form the finished products. Alternatively, the glyceride copolymers can be combined with surfactants or emulsifiers, solvents, suitable adjuncts, and/or any other suitable ingredients to prepare emulsions prior to compounding the finished products.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg A S (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Glyceride Oligomers

In one aspect, the disclosure provides glyceride copolymers of formula (I):

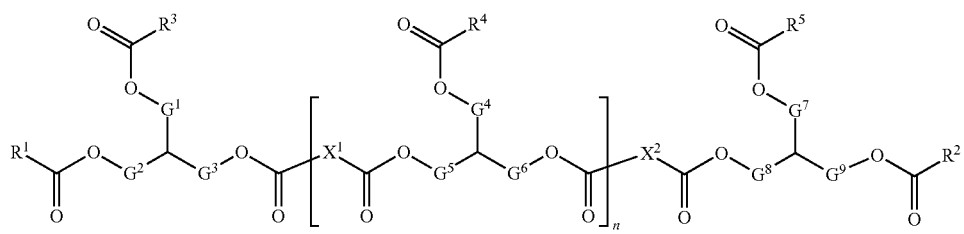

wherein: each $R^1$, $R^2$, $R^3$, $R^4$, and $R^5$ is independently selected from the group consisting of an oligomeric glyceride moiety, a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties; and/or each of the following combinations of moieties may each independently be covalently linked: $R^1$ and $R^3$, $R^2$ and $R^5$, $R^1$ and an adjacent $R^4$, $R^2$ and an adjacent $R^4$, $R^3$ and an adjacent $R^4$, $R^5$ and an adjacent $R^4$, or any two adjacent $R^4$ such that the covalently linked moieties forms an alkenylene moiety; each $X^1$ and $X^2$ is independently selected from the group consisting of a $C_{1-32}$ alkylene, a substituted $C_{1-32}$ alkylene wherein the substituent is one or more —OH moieties, a $C_{2-32}$ alkenylene or a substituted $C_{2-32}$ alkenylene wherein the substituent is one or more —OH moieties; two of $G^1$, $G^2$, and $G^3$ are —$CH_2$—, and one of $G^1$, $G^2$, and $G^3$ is a direct bond; for each individual repeat unit in the repeat unit having index n, two of $G^4$, $G^5$, and $G^6$ are —$CH_2$—, and one of $G^4$, $G^5$, and $G^6$ is a direct bond, and the values $G^4$, $G^5$, and $G^6$ for each individual repeat unit are independently selected from the values of $G^4$, $G^5$, and $G^6$ in other repeating units; two of $G^7$, $G^8$, and $G^9$ are —$CH_2$—, and one of $G^7$, $G^8$, and $G^9$ is a direct bond; and n is an integer from 3 to 250; with the proviso for each of said second glyceride copolymers at least one of $R^1$, $R^2$, $R^3$, and $R^5$, and/or at least one $R^4$ in one individual repeat unit of said repeat unit having index n, is selected from the group consisting of: 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-octadecatrienyl; 9-methyl-8-decenyl; 9-methyl-8-undecenyl; 10-methyl-8-undecenyl; 12-methyl-8,11-tridecadienyl; 12-methyl-8,11-tetradecadienyl; 13-methyl-8,11-tetradecadienyl; 15-methyl-8,11,14-hexadecatrienyl; 15-methyl-8,11,14-heptadecatrienyl; 16-methyl-8,11,14-heptadecatrienyl; 12-tridecenyl; 12-tetradecenyl; 12-pentadecenyl; 12-hexadecenyl; 13-methyl-12-tetradecenyl; 13-methyl-12-pentadecenyl; and 14-methyl-12-pentadecenyl.

$G^1$, $G^2$, and $G^3$ can have any suitable value. In some embodiments, $G^1$ and $G^2$ are —$CH_2$— and $G^3$ is a direct bond. In some other embodiments, $G^1$ and $G^3$ are —$CH_2$— and $G^2$ is a direct bond. In some other embodiments, $G^2$ and $G^3$ are —$CH_2$— and $G^1$ is a direct bond.

$G^4$, $G^5$, and $G^6$ can, in each instance, independently have any suitable value. In some embodiments of any of the aforementioned embodiments, in at least one instance, $G^4$ and $G^5$ are —$CH_2$— and $G^6$ is a direct bond. In some other embodiments of any of the aforementioned embodiments, in at least one instance, $G^4$ and $G^6$ are —$CH_2$— and $G^5$ is a direct bond. In some other embodiments of any of the aforementioned embodiments, in at least one instance, $G^5$ and $G^6$ are —$CH_2$— and $G^4$ is a direct bond.

$G^7$, $G^8$, and $G^9$ can have any suitable value. In some embodiments of any of the aforementioned embodiments, $G^7$ and $G^8$ are —$CH_2$— and $G^9$ is a direct bond. In some other embodiments of any of the aforementioned embodiments, $G^7$ and $G^9$ are —$CH_2$— and $G^8$ is a direct bond. In some other embodiments of any of the aforementioned embodiments, $G^8$ and $G^9$ are —$CH_2$— and $G^7$ is a direct bond. $X^1$ can have any suitable value. In some embodiments of any of the aforementioned embodiments, $X^1$ is —$(CH_2)_{16}$—, —$(CH_2)_{18}$—, —$(CH_2)_{19}$—, —$(CH_2)_{20}$—, —$(CH_2)_{22}$—, —$(CH_2)_{24}$—, —$(CH_2)_{25}$—, —$(CH_2)_{28}$—, —$(CH_2)_7$—CH=CH—$(CH_2)_7$—, —$(CH_2)_7$—CH=CH—$CH_2$—CH=CH—$(CH_2)_7$—, —$(CH_2)_7$—CH=CH—$CH_2$—CH=CH—$CH_2$—CH=CH—$(CH_2)_7$—, —$(CH_2)_7$—CH=CH—$CH_2$—CH=CH—$CH_2$—CH=CH—$CH_2$—CH=CH—$(CH_2)_7$—, —$(CH_2)_7$—CH=CH—$(CH_2)_7$—, —$(CH_2)_7$—CH=CH—$CH_2$—CH=CH—$CH_2$—CH=CH—$CH_2$—CH=CH—$(CH_2)_7$—, —$(CH_2)_{11}$—CH=CH—

$-(CH_2)_{11}-$, $-(CH_2)_7-CH=CH-CH_2-CH=CH-(CH_2)_{11}-$, $-(CH_2)_{11}-CH=CH-CH_2-CH=CH-(CH_2)_7-$, $-(CH_2)_7-CH=CH-CH_2-CH=CH-CH_2-CH=CH-(CH_2)_{11}-$, $-(CH_2)_{11}-CH=CH-CH_2-CH=CH-CH_2-CH=CH-(CH_2)_7-$, $-(CH_2)_9-CH=CH-(CH_2)_7-$, $-(CH_2)_7-CH=CH-(CH_2)_9-$, $-(CH_2)_{11}-CH=CH-(CH_2)_7-$, or $-(CH_2)_7-CH=CH-(CH_2)_{11}-$. In some such embodiments, $X^1$ is $-(CH_2)_{16}-$, $-(CH_2)_{18}-$, $-(CH_2)_{19}-$, $-(CH_2)_{22}-$, $-(CH_2)_{25}-$, $-(CH_2)_{28}-$, $-(CH_2)_7-CH=CH-(CH_2)_7-$, $-(CH_2)_9-CH=CH-(CH_2)_7-$, $-(CH_2)_7-CH=CH-(CH_2)_9-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some such embodiments, $X^1$ is $-(CH_2)_{16}-$, $-(CH_2)_{19}-$, $-(CH_2)_{22}-$, $-(CH_2)_{25}-$, $-(CH_2)_{28}-$, $-(CH_2)_7-CH=CH-(CH_2)_7-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some further such embodiments, $X^1$ is $-(CH_2)_7-CH=CH-(CH_2)_7-$, $-(CH_2)_9-CH=CH-(CH_2)_7-$, $-(CH_2)_7-CH=CH-(CH_2)_9-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some further such embodiments, $X^1$ is $-(CH_2)_7-CH=CH-(CH_2)_7-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, $-(CH_2)_7-CH=CH-CH_2-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$.

$X^2$ can have any suitable value. In some embodiments of any of the aforementioned embodiments, $X^2$ is $-(CH_2)_{16}-$, $-(CH_2)_{18}-$, $-(CH_2)_{19}-$, $-(CH_2)_{20}-$, $-(CH_2)_{22}-$, $-(CH_2)_{24}-$, $-(CH_2)_{25}-$, $-(CH_2)_{28}-$, $-(CH_2)_7-CH=CH-(CH_2)_7-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, $-(CH_2)_7-CH=CH-CH_2-CH=CH-CH_2-CH=CH-CH_2-CH=CH-(CH_2)_7-$, $-(CH_2)_{11}-CH=CH-(CH_2)_{11}-$, $-(CH_2)_7-CH=CH-CH_2-CH=CH-(CH_2)_{11}-$, $-(CH_2)_{11}-CH=CH-CH_2-CH=CH-(CH_2)_7-$, $-(CH_2)_7-CH=CH-CH_2-CH=CH-CH_2-CH=CH-(CH_2)_{11}-$, $-(CH_2)_{11}-CH=CH-CH_2-CH=CH-CH_2-CH=CH-(CH_2)_7-$, $-(CH_2)_9-CH=CH-(CH_2)_7-$, $-(CH_2)_7-CH=CH-(CH_2)_9-$, $-(CH_2)_{11}-CH=CH-(CH_2)_7-$, or $-(CH_2)_7-CH=CH-(CH_2)_{11}-$. In some such embodiments, $X^2$ is $-(CH_2)_{16}-$, $-(CH_2)_{18}-$, $-(CH_2)_{19}-$, $-(CH_2)_{22}-$, $-(CH_2)_{25}-$, $-(CH_2)_{28}-$, $-(CH_2)_7-CH=CH-(CH_2)_7-$, $-(CH_2)_9-CH=CH-(CH_2)_7-$, $-(CH_2)_7-CH=CH-(CH_2)_9-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some such embodiments, $X^2$ is $-(CH_2)_{16}-$, $-(CH_2)_{19}-$, $-(CH_2)_{22}-$, $-(CH_2)_{25}-$, $-(CH_2)_{28}-$, $-(CH_2)_7-CH=CH-(CH_2)_7-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some further such embodiments, $X^2$ is $-(CH_2)_7-CH=CH-(CH_2)_7-$, $-(CH_2)_9-CH=CH-(CH_2)_7-$, $-(CH_2)_7-CH=CH-(CH_2)_9-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$. In some further such embodiments, $X^2$ is $-(CH_2)_7-CH=CH-(CH_2)_7-$, $-(CH_2)_7-CH=CH-CH_2-CH=CH-(CH_2)_7-$, $-(CH_2)_7-CH=CH-CH_2-CH=CH-CH_2-CH=CH-(CH_2)_7-$, or $-(CH_2)_7-CH=CH-CH_2-CH=CH-CH_2-CH=CH-CH_2-CH=CH-(CH_2)_7-$.

$R^1$ can have any suitable value. In some embodiments of any of the aforementioned embodiments, $R^1$ is $C_{1-24}$ alkyl, or $C_{11-24}$ alkyl, or $C_{13-24}$ alkyl, or $C_{15-24}$ alkyl. In some such embodiments, $R^1$ is undecyl, tridecyl, pentadecyl, or heptadecyl. In some further such embodiments, $R^1$ is pentadecyl or heptadecyl. In some embodiments of any of the aforementioned embodiments, $R^1$ is $C_{2-24}$ alkenyl or $C_{9-24}$ alkenyl. In some such embodiments, $R^1$ is 8-heptadecenyl, 10-heptadecenyl, 12-heneicosenyl, 8,11-heptadecadienyl, 8,11,14-heptadecatrienyl, 8-nonenyl, 8-decenyl, 8-undecenyl, 10-undecenyl, 8-dodecenyl, 12-tridecenyl, 12-tetradecenyl, 12-pentadecenyl, 12-hexadecenyl, 9-methyl-8-decenyl, 9-methyl-8-undecenyl, 10-methyl-8-undecenyl, 13-methyl-12-tetradecenyl, 13-methyl-12-pentadecenyl, 14-methyl-12-pentadecenyl, 8,11-dodecadienyl, 8,11-tridecadienyl, 8,11-tetradecadienyl, 8,11-pentadecadienyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 8,11,14-pentadecatrienyl, 8,11,14-hexadecatrienyl, 8,11,14-heptadecatrienyl, or 8,11,14-octadecatrienyl. In some further such embodiments, $R^1$ is 8-heptadecenyl, 10-heptadecenyl, 8,11-heptadecadienyl, or 8,11,14-heptadecatrienyl. In some further such embodiments, $R^1$ is 8-heptadecenyl, 8,11-heptadecadienyl, or 8,11,14-heptadecatrienyl. In some such embodiments, $R^1$ is 8-nonenyl, 8-decenyl, 8-undecenyl, 10-undecenyl, 8-dodecenyl, 8,11-dodecadienyl, 8,11-tridecadienyl, 12-tridecenyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^1$ is 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^1$ is 8-nonenyl, 8-undecenyl, 8,11-dodecadienyl, 8,11-tetradecadienyl, or 8,11,14-pentadecatrienyl. In some embodiments, $R^1$ is an oligomeric glyceride moiety.

$R^2$ can have any suitable value. In some embodiments of any of the aforementioned embodiments, $R^2$ is $C_{1-24}$ alkyl, or $C_{11-24}$ alkyl, or $C_{13-24}$ alkyl, or $C_{15-24}$ alkyl. In some such embodiments, $R^2$ is undecyl, tridecyl, pentadecyl, or heptadecyl. In some further such embodiments, $R^2$ is pentadecyl or heptadecyl. In some embodiments of any of the aforementioned embodiments, $R^2$ is $C_{2-24}$ alkenyl or $C_{9-24}$ alkenyl In some such embodiments, $R^2$ is 8-heptadecenyl, 10-heptadecenyl, 12-heneicosenyl, 8,11-heptadecadienyl, 8,11,14-heptadecatrienyl, 8-nonenyl, 8-decenyl, 8-undecenyl, 10-undecenyl, 8-dodecenyl, 12-tridecenyl, 12-tetradecenyl, 12-pentadecenyl, 12-hexadecenyl, 9-methyl-8-decenyl, 9-methyl-8-undecenyl, 10-methyl-8-undecenyl, 13-methyl-12-tetradecenyl, 13-methyl-12-pentadecenyl, 14-methyl-12-pentadecenyl, 8,11-dodecadienyl, 8,11-tridecadienyl, 8,11-tetradecadienyl, 8,11-pentadecadienyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 8,11,14-pentadecatrienyl, 8,11,14-hexadecatrienyl, 8,11,14-heptadecatrienyl, or 8,11,14-octadecatrienyl. In some further such embodiments, $R^2$ is 8-heptadecenyl, 10-heptadecenyl, 8,11-heptadecadienyl, or 8,11,14-heptadecatrienyl. In some further such embodiments, $R^2$ is 8-heptadecenyl, 8,11-heptadecadienyl, or 8,11,14-heptadecatrienyl. In some such embodiments, $R^2$ is 8-nonenyl, 8-decenyl, 8-undecenyl, 10-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^2$ is 8-nonenyl, 8-decenyl, 8-undecenyl, 8-dodecenyl, 8,11-dodecadienyl, 8,11-tridecadienyl, 12-tridecenyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^2$ is 8-nonenyl, 8-undecenyl, 8,11-dodecadienyl, 8,11-tetradecadienyl, or 8,11,14-pentadecatrienyl. In some embodiments, $R^2$ is an oligomeric glyceride moiety.

$R^3$ can have any suitable value. In some embodiments of any of the aforementioned embodiments, $R^3$ is $C_{1-24}$ alkyl, or $C_{11-24}$ alkyl, or $C_{13-24}$ alkyl, or $C_{15-24}$ alkyl. In some such embodiments, $R^3$ is undecyl, tridecyl, pentadecyl, or heptadecyl. In some further such embodiments, $R^3$ is pentadecyl or heptadecyl. In some embodiments of any of the aforementioned embodiments, $R^3$ is $C_{2-24}$ alkenyl or $C_{9-24}$ alkenyl. In some such embodiments, $R^3$ is 8-heptadecenyl, 10-heptadecenyl, 12-heneicosenyl, 8,11-heptadecadienyl, 8,11,14-heptadecatrienyl, 8-nonenyl, 8-decenyl, 8-undecenyl, 10-undecenyl, 8-dodecenyl, 12-tridecenyl, 12-tetradecenyl, 12-pentadecenyl, 12-hexadecenyl, 9-methyl-8-decenyl, 9-methyl-8-undecenyl, 10-methyl-8-undecenyl, 13-methyl-12-tetradecenyl, 13-methyl-12-pentadecenyl, 14-methyl-12-pentadecenyl, 8,11-dodecadienyl, 8,11-tridecadienyl, 8,11-tetradecadienyl, 8,11-pentadecadienyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 8,11,14-pentadecatrienyl, 8,11,14-hexadecatrienyl, 8,11,14-heptadecatrienyl, or 8,11,14-octadecatrienyl. In some further such embodiments, $R^3$ is 8-heptadecenyl, 10-heptadecenyl, 8,11-heptadecadienyl, or 8,11,14-heptadecatrienyl. In some further such embodiments, $R^3$ is 8-heptadecenyl, 8,11-heptadecadienyl, or 8,11,14-heptadecatrienyl. In some such embodiments, $R^3$ is 8-nonenyl, 8-decenyl, 8-undecenyl, 10-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^3$ is 8-nonenyl, 8-decenyl, 8-undecenyl, 8-dodecenyl, 8,11-dodecadienyl, 8,11-tridecadienyl, 12-tridecenyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^3$ is 8-nonenyl, 8-undecenyl, 8,11-dodecadienyl, 8,11-tetradecadienyl, or 8,11,14-pentadecatrienyl. In some embodiments, $R^3$ is an oligomeric glyceride moiety.

$R^4$ can, in each of its instances, have any suitable value. In some embodiments of any of the aforementioned embodiments, $R^4$, in at least one instance, is $C_{1-24}$ alkyl, or $C_{11-24}$ alkyl, or $C_{13-24}$ alkyl, or $C_{15-24}$ alkyl. In some such embodiments, $R^4$ is, in at least one instance, undecyl, tridecyl, pentadecyl, or heptadecyl. In some further such embodiments, $R^4$ is, in at least one instance, pentadecyl or heptadecyl. In some embodiments of any of the aforementioned embodiments, $R^4$ is, in at least one instance, $C_{2-24}$ alkenyl or $C_{9-24}$ alkenyl. In some such embodiments, $R^4$ is, in at least one instance, 8-heptadecenyl, 10-heptadecenyl, 12-heneicosenyl, 8,11-heptadecadienyl, 8,11,14-heptadecatrienyl, 8-nonenyl, 8-decenyl, 8-undecenyl, 10-undecenyl, 8-dodecenyl, 12-tridecenyl, 12-tetradecenyl, 12-pentadecenyl, 12-hexadecenyl, 9-methyl-8-decenyl, 9-methyl-8-undecenyl, 10-methyl-8-undecenyl, 13-methyl-12-tetradecenyl, 13-methyl-12-pentadecenyl, 14-methyl-12-pentadecenyl, 8,11-dodecadienyl, 8,11-tridecadienyl, 8,11-tetradecadienyl, 8,11-pentadecadienyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 8,11,14-pentadecatrienyl, 8,11,14-hexadecatrienyl, 8,11,14-heptadecatrienyl, or 8,11,14-octadecatrienyl. In some further such embodiments, $R^4$ is, in at least one instance, 8-heptadecenyl, 10-heptadecenyl, 8,11-heptadecadienyl, or 8,11,14-heptadecatrienyl. In some further such embodiments, $R^4$ is, in at least one instance, 8-heptadecenyl, 8,11-heptadecadienyl, or 8,11,14-heptadecatrienyl. In some such embodiments, $R^4$ is, in at least one instance, 8-nonenyl, 8-decenyl, 8-undecenyl, 10-undecenyl, 8-dodecenyl, 8,11-dodecadienyl, 8,11-tridecadienyl, 12-tridecenyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^4$ is, in at least one instance, 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^4$ is, in at least one instance, 8-nonenyl, 8-undecenyl, 8,11-dodecadienyl, 8,11-tetradecadienyl, or 8,11,14-pentadecatrienyl. In some embodiments, $R^4$, in at least one instance, is an oligomeric glyceride moiety.

$R^5$ can have any suitable value. In some embodiments of any of the aforementioned embodiments, $R^5$ is $C_{1-24}$ alkyl, or $C_{11-24}$ alkyl, or $C_{13-24}$ alkyl, or $C_{15-24}$ alkyl. In some such embodiments, $R^5$ is undecyl, tridecyl, pentadecyl, or heptadecyl. In some further such embodiments, $R^5$ is pentadecyl or heptadecyl. In some embodiments of any of the aforementioned embodiments, $R^5$ is $C_{2-24}$ alkenyl or $C_{9-24}$ alkenyl. In some such embodiments, $R^5$ is 8-heptadecenyl, 10-heptadecenyl, 12-heneicosenyl, 8,11-heptadecadienyl, 8,11,14-heptadecatrienyl, 8-nonenyl, 8-decenyl, 8-undecenyl, 10-undecenyl, 8-dodecenyl, 12-tridecenyl, 12-tetradecenyl, 12-pentadecenyl, 12-hexadecenyl, 9-methyl-8-decenyl, 9-methyl-8-undecenyl, 10-methyl-8-undecenyl, 13-methyl-12-tetradecenyl, 13-methyl-12-pentadecenyl, 14-methyl-12-pentadecenyl, 8,11-dodecadienyl, 8,11-tridecadienyl, 8,11-tetradecadienyl, 8,11-pentadecadienyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 8,11,14-pentadecatrienyl, 8,11,14-hexadecatrienyl, 8,11,14-heptadecatrienyl, or 8,11,14-octadecatrienyl. In some further such embodiments, $R^5$ is 8-heptadecenyl, 10-heptadecenyl, 8,11-heptadecadienyl, or 8,11,14-heptadecatrienyl. In some further such embodiments, $R^5$ is 8-heptadecenyl, 8,11-heptadecadienyl, or 8,11,14-heptadecatrienyl. In some such embodiments, $R^5$ is 8-nonenyl, 8-decenyl, 8-undecenyl, 10-undecenyl, 8-dodecenyl, 8,11-dodecadienyl, 12-tridecenyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^5$ is 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, $R^5$ is 8-nonenyl, 8-undecenyl, 8,11-dodecadienyl, 8,11-tetradecadienyl, or 8,11,14-pentadecatrienyl. In some embodiments, $R^5$ is an oligomeric glyceride moiety.

The variable n can have any suitable value. In some embodiments of any of the aforementioned embodiments, n is an integer from 3 to 250, or from 5 to 180, or from 6 to 140, or from 8 to 70, or from 9 to 40, or from 9 to 26. In some other embodiments, n is an integer from 3 to 35, or from 5 to 30, or from 7 to 25, or from 10 to 20.

In some embodiments of any of the aforementioned embodiments, the glyceride polymers include only compounds wherein at least one of $R^1$, $R^2$, $R^3$, and $R^5$, or at least one instance of $R^4$, is selected from the group consisting of: 8-nonenyl; 8-decenyl; 8-undecenyl; 10-undecenyl, 12-tridecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-heptadecatrienyl; and 8,11,14-octadecatrienyl. In some other embodiments of any of the aforementioned embodiments, the glyceride polymers include only compounds wherein at least one of $R^1$, $R^2$, $R^3$, and $R^5$, or at least one instance of $R^4$, is selected from the group consisting of: 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-heptadecatrienyl; and 8,11,14-octadecatrienyl. In some other embodiments of any of the aforementioned embodiments, the glyceride polymers include only compounds wherein at least one of $R^1$, $R^2$, $R^3$, and $R^5$, or at least one instance of $R^4$, is selected from the group consisting of: 8-nonenyl; 8-undecenyl; 8,11-dodecadienyl; 8,11-tetradecadienyl; or 8,11,14-pentadecatrienyl. In some embodiments of any of the aforementioned embodiments, the glyceride polymers include only compounds wherein at least one of $R^1$, $R^2$, $R^3$, and $R^5$, or at least one instance of $R^4$, is selected from the group consisting of: 8-nonenyl; 8-decenyl; 8-undecenyl; 10-undecenyl; 12-tridecenyl; 8-dodecenyl; 8,11-dodecadienyl; 8,11-tridecadienyl; 8,11-tetradecadienyl; 8,11-pentadecadienyl; 8,11,14-pentadecatrienyl; and 8,11,14-hexadecatrienyl. In some other embodiments of any of the aforementioned embodiments, the glyceride polymers include only compounds wherein at least one of $R^1$, $R^2$, $R^3$, and $R^5$, or at least one instance of $R^4$, is selected from the group consisting of: 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; and 8,11,14-hexadecatrienyl. In some other embodiments of any of the aforementioned embodiments, the glyceride polymers include only compounds wherein at least one of $R^1$, $R^2$, $R^3$, and $R^5$, or at least one instance of $R^4$, is $C_{2-15}$ alkenyl, or $C_{2-14}$ alkenyl, or $C_{5-14}$ alkenyl, or $C_{2-13}$ alkenyl, or $C_{2-12}$ alkenyl, or $C_{5-12}$ alkenyl.

In a another aspect, glyceride copolymers, which comprises constitutional units formed from reacting two or more monomers in the presence of a metathesis catalyst, the two or more monomers comprise monomer compounds of formula (IIa):

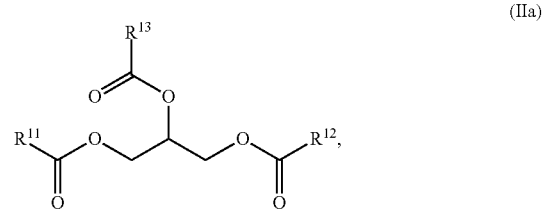

(IIa)

and monomer compounds of formula (IIb):

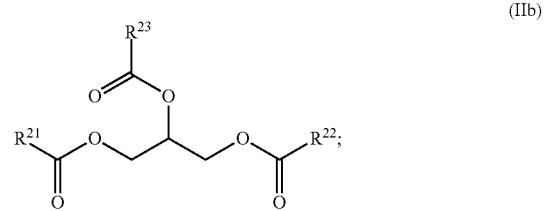

(IIb)

wherein, each $R^{11}$, $R^{12}$, and $R^{13}$ is independently a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties with the proviso that at least one of $R^{11}$, $R^{12}$, and $R^{13}$ is a $C_{2-24}$ alkenyl or a substituted $C_{2-24}$ alkenyl wherein the substituent is one or more —OH moieties; each $R^{21}$, $R^{22}$, and $R^{23}$ is independently a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties, with the proviso that at least one of $R^{21}$, $R^{22}$, and $R^{23}$ is 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-octadecatrienyl; 9-methyl-8-decenyl; 9-methyl-8-undecenyl; 10-methyl-8-undecenyl; 12-methyl-8,11-tridecadienyl; 12-methyl-8,11-tetradecadienyl; 13-methyl-8,11-tetradecadienyl; 15-methyl-8,11,14-hexadecatrienyl; 15-methyl-8,11,14-heptadecatrienyl; 16-methyl-8,11,14-heptadecatrienyl; 12-tridecenyl; 12-tetradecenyl; 12-pentadecenyl; 12-hexadecenyl; 13-methyl-12-tetradecenyl; 13-methyl-12-pentadecenyl; and 14-methyl-12-pentadecenyl.

The variables $R^{11}$, $R^{12}$, and $R^{13}$ can have any suitable value. In some embodiments, $R^{11}$, $R^{12}$, and $R^{13}$ are independently $C_{1-24}$ alkyl, or $C_{11-24}$ alkyl, or $C_{13-24}$ alkyl, or $C_{15-24}$ alkyl. In some such embodiments, $R^{11}$, $R^{12}$, and $R^{13}$ are independently undecyl, tridecyl, pentadecyl, or heptadecyl. In some further such embodiments, $R^{11}$, $R^{12}$, and $R^{13}$ are independently pentadecyl or heptadecyl. In some embodiments of any of the aforementioned embodiments, $R^{11}$, $R^{12}$, and $R^{13}$ are independently $C_{2-24}$ alkenyl, or $C_{9-24}$ alkenyl, or $C_{11-24}$ alkenyl, or $C_{13-24}$ alkenyl, or $C_{15-24}$ alkenyl. In some such embodiments, $R^{11}$, $R^{12}$ and $R^{13}$ are independently 8-heptadecenyl, 10-heptadecenyl, 8,11-heptadecadienyl or 8,11,14-heptadecatrienyl. In some further such embodiments, $R^{11}$, $R^{12}$ and $R^{13}$ are independently 8-heptadecenyl, 8,11-heptadecadienyl, or 8,11,14-heptadecatrienyl.

The variables $R^{21}$, $R^{22}$, and $R^{23}$ can have any suitable value. In some embodiments of any of the foregoing embodiments, zero, one, or two of $R^{21}$, $R^{22}$, and $R^{23}$ are independently $C_{1-24}$ alkyl, or $C_{11-24}$ alkyl, or $C_{13-24}$ alkyl, or $C_{15-24}$ alkyl. In some such embodiments, zero, one, or two of $R^{21}$, $R^{22}$, and $R^{23}$ are independently undecyl, tridecyl, pentadecyl, or heptadecyl. In some further such embodiments, zero, one, or two of $R^{21}$, $R^{22}$, and $R^{23}$ are independently pentadecyl or heptadecyl. In some embodiments of any of the aforementioned embodiments, zero, one, or two of $R^{21}$, $R^{22}$, and $R^{23}$ are independently $C_{2-24}$ alkenyl, or $C_{9-24}$ alkenyl, or $C_{11-24}$ alkenyl, or $C_{13-24}$ alkenyl, or $C_{15-24}$ alkenyl. In some such embodiments, zero, one, or two of $R^{21}$, $R^{22}$, and $R^{23}$ are independently 8-heptadecenyl, 10-heptadecenyl, 8,11-heptadecadienyl or 8,11,14-heptadecatrienyl. In some further such embodiments, zero, one, or two of $R^{21}$, $R^{22}$, and $R^{23}$ are independently 8-heptadecenyl, 8,11-heptadecadienyl, or 8,11,14-heptadecatrienyl.

In some other embodiments of any of the foregoing embodiments, one, two, or three of $R^{21}$, $R^{22}$, and $R^{23}$ are independently $C_{2-15}$ alkenyl, or $C_{2-14}$ alkenyl, $C_{5-14}$ alkenyl, or $C_{2-13}$ alkenyl, or $C_{2-12}$ alkenyl, or $C_{5-12}$ alkenyl. In some such embodiments, one, two, or three of $R^{21}$, $R^{22}$, and $R^{23}$ are independently 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-octadecatrienyl, 9-methyl-8-decenyl, 9-methyl-8-undecenyl, 10-methyl-8-undecenyl, 12-methyl-8,11-tridecadienyl, 12-methyl-8,11-tetradecadienyl, 13-methyl-8,11-tetradecadienyl, 15-methyl-8,11,14-hexadecatrienyl, 15-methyl-8,11,14-heptadecatrienyl, 16-methyl-8,11,14-heptadecatrienyl, 12-tridecenyl, 12-tetradecenyl, 12-pentadecenyl, 12-hexadecenyl, 13-methyl-12-tetradecenyl, 13-methyl-12-pentadecenyl, and 14-methyl-12-pentadecenyl, 10-undecenyl, 8,11,14-heptadecatrienyl, or 8,11,14-octadecatrienyl. In some further such embodiments, one, two, or three of $R^{21}$, $R^{22}$, and $R^{23}$ are independently 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, one, two, or three of $R^{21}$, $R^{22}$, and $R^{23}$ are independently 8-nonenyl, 8-undecenyl, 8,11-dodecadienyl, 8,11-tetradecadienyl, or 8,11,14-pentadecatrienyl.

The glyceride copolymers disclosed herein can have any suitable molecular weight. In some embodiments of any of the aforementioned embodiments, the glyceride copolymer has a weight average molecular weight ranging from 4,000 g/mol to 150,000 g/mol, or from 5,000 g/mol to 130,000 g/mol, or from 6,000 g/mol to 100,000 g/mol, or from 7,000 g/mol to 50,000 g/mol, or from 8,000 g/mol to 30,000 g/mol, or from 8,000 g/mol to 20,000 g/mol.

In some embodiments, the glyceride copolymer has a number-average molecular weight ($M_n$) from 2,000 g/mol to 150,000 g/mol, or from 3,000 g/mol to 30,000 g/mol, or from 4,000 g/mol to 20,000 g/mol.

The glyceride copolymers disclosed herein can have any suitable ratio of constitutional units formed from monomer compounds of formula (IIa) to constitutional units formed from monomer compounds of formula (IIb). In some embodiments of any of the aforementioned embodiments, the number ratio of constitutional units formed from monomer compounds of formula (IIa) to constitutional units formed from monomer compounds of formula (IIb) is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. The glyceride copolymers disclosed herein can include additional constitutional units not formed from monomer compounds of either formula (IIa) or formula (IIb), including, but not limited to, constitutional units formed from other unsaturated polyol esters, such as unsaturated diols, triols, and the like.

Or, in some other embodiments of any of the foregoing embodiments, the two or more monomers are reacted in the presence of the metathesis catalyst as part of a reaction mixture, wherein the weight-to-weight ratio of the monomer compounds of formula (IIa) to the monomer compounds of formula (IIb) in the reaction mixture is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. In some embodiments, the reaction mixture includes additional monomer compounds besides monomer compounds of formula (IIa) and formula (IIb).

Any suitable metathesis catalyst can be used, as described in more detail below. In some embodiments of any of the aforementioned embodiments, the metathesis catalyst is an organoruthenium compound, an organoosmium compound, an organotungsten compound, or an organomolybdenum compound.

In another aspect, the disclosure provides glyceride copolymers, which comprises constitutional units formed from reacting two or more monomers in the presence of a first metathesis catalyst; wherein the first monomer is an unsaturated natural oil glyceride, and the second monomer is an unsaturated alkenylized natural oil glyceride. In another aspect, the disclosure provides glyceride copolymers, which comprises constitutional units formed from reacting two or more monomers in the presence of a first metathesis catalyst; wherein the first monomer is an unsaturated synthetic polyol ester, and the second monomer is an unsaturated alkenylized natural oil glyceride. In another aspect, the disclosure provides glyceride copolymers, which comprises constitutional units formed from reacting two or more monomers in the presence of a first metathesis catalyst; wherein the first monomer is an unsaturated natural oil glyceride, and the second monomer is an unsaturated alkenylized synthetic polyol ester. In another aspect, the disclosure provides glyceride copolymers, which comprises constitutional units formed from reacting two or more monomers in the presence of a first metathesis catalyst; wherein the first monomer is an unsaturated synthetic polyol ester, and the second monomer is an unsaturated alkenylized synthetic polyol ester. In another aspect, the disclosure provides glyceride copolymers, which comprises constitutional units formed from reacting two or more monomers in the presence of a first metathesis catalyst; wherein the first monomer is a first unsaturated alkenylized synthetic polyol ester, and the second monomer is a second unsaturated alkenylized synthetic polyol ester. In another aspect, the disclosure provides glyceride copolymers, which comprises constitutional units formed from reacting two or more monomers in the presence of a first metathesis; wherein the first monomer is a first unsaturated alkenylized natural oil glyceride, and the second monomer is a second unsaturated alkenylized natural oil glyceride. In another aspect, the disclosure provides glyceride copolymers, which comprises constitutional units formed from reacting two or more monomers in the presence of a first metathesis; wherein the first monomer is an unsaturated alkenylized natural oil glyceride, and the second monomer is an unsaturated alkenylized synthetic polyol ester.

In some embodiments, the unsaturated alkenylized natural oil glyceride is formed from the reaction of a second unsaturated natural oil glyceride with a short-chain alkene in the presence of a second metathesis catalyst. In some such embodiments, the unsaturated alkenylized natural oil glyceride has a lower molecular weight than the second unsaturated natural oil glyceride. Any suitable short-chain alkene can be used, according to the embodiments described above. In some embodiments, the short-chain alkene is a $C_{2-8}$ olefin, or a $C_{2-6}$ olefin. In some such embodiments, the short-chain alkene is ethylene, propylene, 1-butene, 2-butene, isobutene, 1-pentene, 2-pentene, 1-hexene, 2-hexene, or 3-hexene. In some further such embodiments, the short-chain alkene is ethylene, propylene, 1-butene, 2-butene, or isobutene. In some embodiments, the short-chain alkene is ethylene. In some embodiments, the short-chain alkene is propylene. In some embodiments, the short-chain alkene is 1-butene. In some embodiments, the short-chain alkene is 2-butene. In some other embodiments, the short-chain alkene is a branched short-chain alkene. Non-limiting examples of such branched short-chain alkenes include, but are not limited to, isobutylene, 3-methyl-1-butene, 3-methyl-1-pentene, and 4-methyl-1-pentene.

The unsaturated natural oil glyceride can be obtained from any suitable natural oil source. In some embodiments of any of the aforementioned embodiments, the unsaturated natural oil glycerides are obtained from synthesized oils, natural oils (e.g., vegetable oils, algae oils, bacterial and/or fungal derived oils, and animal fats), combinations of these, and the like. In some embodiments, the natural oil is obtained from a vegetable oil, such as a seed oil. Recycled used vegetable oils may also be used. In some further embodiments, the vegetable oil is Abyssinian oil, Almond Oil, Apricot Oil, Apricot Kernel oil, Argan oil, Avocado Oil, Babassu Oil, Baobab Oil, Black Cumin Oil, Black Currant Oil, Borage Oil, Camelina oil, Carinata oil, Canola (low erucic acid rapeseed) oil, Castor oil, Cherry Kernel Oil, Coconut oil, Corn oil, Cottonseed oil, Echium Oil, Evening Primrose Oil, Flax Seed Oil, Grape Seed Oil, Grapefruit Seed Oil, Hazelnut Oil, Hemp Seed Oil, Jatropha oil, Jojoba Oil, Kukui Nut Oil, Linseed Oil, Macadamia Nut Oil, Meadowfoam Seed Oil, Moringa Oil, Mustard Seed Oil, Neem Oil, Olive Oil, Palm Oil, Palm Kernel Oil, Peach Kernel Oil, Peanut Oil, Pecan Oil, Pennycress oil, Perilla Seed Oil, Pistachio Oil, Pomegranate Seed Oil, Pongamia oil, Pumpkin Seed Oil, Raspberry Oil, Red Palm Olein, Rice Bran Oil, Rosehip Oil, Safflower Oil, Seabuckthorn Fruit Oil, Sesame Seed Oil, Shea Olein, Sunflower Oil, Soybean Oil, Tonka Bean Oil, Tung Oil, Walnut Oil, Wheat Germ Oil, High Oleoyl Soybean Oil, High Oleoyl Sunflower Oil, High Oleoyl Safflower Oil, High Erucic Acid Rapeseed Oil, and mixtures thereof. In some embodiments, the vegetable oil is palm oil. In some embodiments, the vegetable oil is soybean oil. In some embodiments, the vegetable oil is canola oil. In some embodiments, a representative, non-limiting example of animal fat is lard, tallow, chicken fat, yellow grease, fish oil, emu oil, combinations of these, and the like. In some embodiments, a representative non-limiting example of a synthesized oil includes tall oil, which is a byproduct of wood pulp manufacture. In some embodiments, the natural oil is refined, bleached, and/or deodorized.

Natural oils of the type described herein typically are composed of triglycerides of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a $C_{16}$ acid), and oleic acid (a $C_{18}$ acid); polyunsaturated acids include such fatty acids as linoleic acid (a di-unsaturated $C_{18}$ acid), linolenic acid (a tri-unsaturated $C_{18}$ acid), and arachidonic acid (a tetra-unsubstituted $C_{20}$ acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example soybean oil contains a mixture of predominantly C16 and C18 acid groups where stearic acid, oleic acid, linoleic acid, and linolenic acid are in the ratio of about 15:24:50:11, and an average number of double bonds of 4.4-4.7 per triglyceride. One method of quantifying the number of double bonds is the iodine value (IV) which is defined as the number of grams of iodine that will react with 100 grams of oil. Therefore for soybean oil, the average iodine value range is from 120-140. Soybean oil may comprise about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12octadecadienoic acid), and linolenic acid (9,12,15-octadecatrienoic acid).

In an exemplary embodiment, the vegetable oil is canola oil, for example, refined, bleached, and deodorized canola oil (i.e., RBD canola oil). Canola oil is an unsaturated polyol ester of glycerol that typically comprises about 95% weight or greater (e.g., 99% weight or greater) triglycerides of fatty acids. Major fatty acids in the polyol esters of canola oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Canola oil is a highly unsaturated vegetable oil with many of the triglyceride molecules having at least two unsaturated fatty acids (i.e., a polyunsaturated triglyceride).

In some embodiments, the unsaturated alkenylized synthetic polyol ester is formed from the reaction of an unsaturated synthetic polyol ester with a short-chain alkene in the presence of a second metathesis catalyst. In some such embodiments, the unsaturated alkenylized synthetic polyol ester has a lower molecular weight than the second unsaturated synthetic polyol ester. Any suitable short-chain alkene can be used, according to the embodiments described above. In some embodiments, the short-chain alkene is a $C_{2-8}$ olefin, or a $C_{2-6}$ olefin. In some such embodiments, the short-chain alkene is ethylene, propylene, 1-butene, 2-butene, isobutene, 1-pentene, 2-pentene, 1-hexene, 2-hexene, or 3-hexene. In some further such embodiments, the short-chain alkene is ethylene, propylene, 1-butene, 2-butene, or isobutene. In some embodiments, the short-chain alkene is ethylene. In some embodiments, the short-chain alkene is propylene. In some embodiments, the short-chain alkene is 1-butene. In some embodiments, the short-chain alkene is 2-butene. In some other embodiments, the short-chain alkene is a branched short-chain alkene. Non-limiting examples of such branched short-chain alkenes include, but are not limited to, isobutylene, 3-methyl-1-butene, 3-methyl-1-pentene, and 4-methyl-1-pentene.

The unsaturated synthetic polyol ester includes esters such as those derived from ethylene glycol or propylene glycol, polyethylene glycol, polypropylene glycol, or poly (tetramethylene ether) glycol, esters such as those derived from pentaerythritol, dipentaerythritol, tripentaerythritol, trimethylolpropane, or neopentyl glycol, or sugar esters such as SEFOSE®. Sugar esters such as SEFOSE® include one or more types of sucrose polyesters, with up to eight ester groups that could undergo a metathesis exchange reaction. Sucrose polyesters are derived from a natural resource and therefore, the use of sucrose polyesters can result in a positive environmental impact. Sucrose polyesters are polyester materials, having multiple substitution positions around the sucrose backbone coupled with the chain length, saturation, and derivation variables of the fatty chains. Such sucrose polyesters can have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, such sucrose polyesters may have an unsaturation or iodine value ("IV") of about 3 to about 140. In another embodiment the sucrose polyester may have an IV of about 10 to about 120. In yet another embodiment the sucrose polyester may have an IV of about 20 to 100. Further, such sucrose polyesters have a chain length of about $C_{12-20}$ but are not limited to these chain lengths.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio.

Other examples of suitable unsaturated polyol esters may include but not be limited to sorbitol esters, maltitol esters, sorbitan esters, maltodextrin derived esters, xylitol esters, polyglycerol esters, and other sugar derived esters.

The glyceride copolymers disclosed herein can have any suitable molecular weight. In some embodiments of any of the aforementioned embodiments, the glyceride copolymer has a weight average molecular weight ranging from 4,000 g/mol to 150,000 g/mol, or from 5,000 g/mol to 130,000 g/mol, or from 6,000 g/mol to 100,000 g/mol, or from 7,000 g/mol to 50,000 g/mol, or from 8,000 g/mol to 30,000 g/mol, or from 8,000 g/mol to 20,000 g/mol.

In some embodiments, the glyceride copolymer has a number-average molecular weight ($M_n$) from 2,000 g/mol to 150,000 g/mol, or from 3,000 g/mol to 30,000 g/mol, or from 4,000 g/mol to 20,000 g/mol.

The glyceride copolymers disclosed herein can have any suitable ratio of constitutional units formed from the first monomer to constitutional units formed from the second monomer. In some embodiments of any of the aforementioned embodiments, the number ratio of constitutional units formed from the first monomer to constitutional units formed from the second monomer is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. The glyceride copolymers disclosed herein can include additional constitutional units not formed from the first monomer or the second monomer, including, but not limited to, constitutional units formed from other unsaturated polyol esters, such as unsaturated diols, triols, and the like.

Or, in some other embodiments of any of the foregoing embodiments, the two or more monomers are reacted in the presence of the metathesis catalyst as part of a reaction mixture, wherein the weight-to-weight ratio of the first monomer to the second monomer in the reaction mixture is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. In some embodiments, the reaction mixture includes additional monomer compounds besides the first monomer and the second monomer.

Any suitable metathesis catalyst can be used as either the first metathesis catalyst or the second metathesis catalyst, as described in more detail below. In some embodiments of any of the aforementioned embodiments, the first and second metathesis catalysts are an organoruthenium compound, an organoosmium compound, an organo-tungsten compound, or an organomolybdenum compound.

Additional glyceride copolymers are contemplated as products of the synthetic methods and examples disclosed herein.

Synthetic Methods

In a fifth aspect, the disclosure provides methods of forming a glyceride copolymer composition, the methods comprising: (a) providing a reaction mixture comprising a metathesis catalyst and monomer compounds of formula (IIIa):

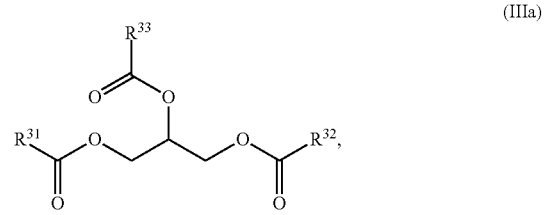

and monomer compounds of formula (IIIb):

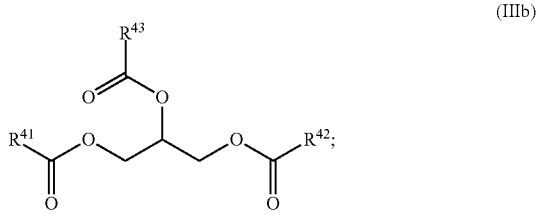

(IIIb)

wherein, $R^{31}$, $R^{32}$, and $R^{33}$ are independently $C_{1-24}$ alkyl or $C_{2-24}$ alkenyl, each of which is optionally substituted one or more times by —OH, provided that at least one of $R^{31}$, $R^{32}$, and $R^{33}$ is $C_{2-24}$ alkenyl, which is optionally substituted one or more times by —OH; and $R^{41}$, $R^{42}$, and $R^{43}$ are independently $C_{1-24}$ alkyl or $C_{2-24}$ alkenyl, each of which is optionally substituted one or more times by —OH, provided that at least one of $R^{41}$, $R^{42}$, and $R^{43}$ is 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl; and (b) reacting the monomer compounds of formula (IIIa) with the monomer compounds of formula (IIIb) in the presence of the metathesis catalyst to form the glyceride polymer composition.

The variables $R^{31}$, $R^{32}$, and $R^{33}$ can have any suitable value. In some embodiments, $R^{31}$, $R^{32}$, and $R^{33}$ are independently $C_{1-24}$ alkyl, or $C_{11-24}$ alkyl, or $C_{13-24}$ alkyl, or $C_{15-24}$ alkyl. In some such embodiments, $R^{31}$, $R^{32}$, and $R^{33}$ are independently undecyl, tridecyl, pentadecyl, or heptadecyl. In some further such embodiments, $R^{31}$, $R^{32}$, and $R^{33}$ are independently pentadecyl or heptadecyl. In some embodiments of any of the aforementioned embodiments, $R^{31}$, $R^{32}$, and $R^{33}$ are independently $C_{2-24}$ alkenyl, or $C_{9-24}$ alkenyl, or $C_{11-24}$ alkenyl, or $C_{13-24}$ alkenyl, or $C_{15-24}$ alkenyl. In some such embodiments, $R^{31}$, $R^{32}$, and $R^{33}$ are independently 8-heptadecenyl, 10-heptadecenyl, 8,11-heptadecadienyl or 8,11,14-heptadecatrienyl. In some further such embodiments, $R^{31}$, $R^{32}$, and $R^{33}$ are independently 8-heptadecenyl, 8,11-heptadecadienyl, or 8,11,14-heptadecatrienyl.

The variables $R^{41}$, $R^{42}$, and $R^{43}$ can have any suitable value. In some embodiments of any of the foregoing embodiments, zero, one, or two of $R^{41}$, $R^{42}$, and $R^{43}$ are independently $C_{1-24}$ alkyl, or $C_{11-24}$ alkyl, or $C_{13-24}$ alkyl, or $C_{15-24}$ alkyl. In some such embodiments, zero, one, or two of $R^{41}$, $R^{42}$, and $R^{43}$ are independently undecyl, tridecyl, pentadecyl, or heptadecyl. In some further such embodiments, zero, one, or two of $R^{41}$, $R^{42}$, and $R^{43}$ are independently pentadecyl or heptadecyl. In some embodiments of any of the aforementioned embodiments, zero, one, or two of $R^{41}$, $R^{42}$, and $R^{43}$ are independently $C_{2-24}$ alkenyl, or $C_{9-24}$ alkenyl, or $C_{11-24}$ alkenyl, or $C_{13-24}$ alkenyl, or $C_{15-24}$ alkenyl. In some such embodiments, zero, one, or two of $R^{41}$, $R^{42}$, and $R^{43}$ are independently 8-heptadecenyl, 10-heptadecenyl, 8,11-heptadecadienyl or 8,11,14-heptadecatrienyl. In some further such embodiments, zero, one, or two of $R^{41}$, $R^{42}$, and $R^{43}$ are independently 8-heptadecenyl, 8,11-heptadecadienyl, or 8,11,14-heptadecatrienyl.

In some other embodiments of any of the foregoing embodiments, one, two, or three of $R^{41}$, $R^{42}$, and $R^{43}$ are independently $C_{2-15}$ alkenyl, or $C_{2-14}$ alkenyl, or $C_{2-13}$ alkenyl, or $C_{2-12}$ alkenyl, or $C_{5-12}$ alkenyl. In some such embodiments, one, two, or three of $R^{41}$, $R^{42}$, and $R^{43}$ are independently 8-nonenyl, 8-decenyl, 8-undecenyl, 10-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, one, two, or three of $R^{41}$, $R^{42}$, and $R^{43}$ are independently 8-nonenyl, 8-decenyl, 8-undecenyl, 8-dodecenyl, 8,11-dodecadienyl, 8,11-tridecadienyl, 8,11-tetradecadienyl, 8,11-pentadecadienyl, 8,11,14-pentadecatrienyl, 8,11,14-hexadecatrienyl, 8,11,14-heptadecatrienyl, or 8,11,14-octadecatrienyl. In some further such embodiments, one, two, or three of $R^{41}$, $R^{42}$, and $R^{43}$ are independently 8-nonenyl, 8-undecenyl, 8,11-dodecadienyl, 8,11-tetradecadienyl, or 8,11,14-pentadecatrienyl.

The glyceride copolymers formed by the methods disclosed herein can have any suitable molecular weight. In some embodiments of any of the aforementioned embodiments, the glyceride copolymer has a weight average molecular weight ranging from 4,000 g/mol to 150,000 g/mol, or from 5,000 g/mol to 130,000 g/mol, or from 6,000 g/mol to 100,000 g/mol, or from 7,000 g/mol to 50,000 g/mol, or from 8,000 g/mol to 30,000 g/mol, or from 8,000 g/mol to 20,000 g/mol.

The glyceride copolymers formed by the methods disclosed herein can have any suitable ratio of constitutional units formed from monomer compounds of formula (IIIa) to constitutional units formed from monomer compounds of formula (IIIb). In some embodiments of any of the aforementioned embodiments, the number ratio of constitutional units formed from monomer compounds of formula (IIIa) to constitutional units formed from monomer compounds of formula (IIIb) is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. The glyceride copolymers disclosed herein can include additional constitutional units not formed from monomer compounds of either formula (IIIa) or formula (IIIb).

Or, in some other embodiments of any of the foregoing embodiments, the two or more monomers are reacted in the presence of the metathesis catalyst as part of a reaction mixture, wherein the weight-to-weight ratio of the monomer compounds of formula (IIIa) to the monomer compounds of formula (IIIb) in the reaction mixture is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. In some embodiments, the reaction mixture includes additional monomer compounds besides monomer compounds of formula (IIIa) and formula (IIIb).

Any suitable metathesis catalyst can be used, as described in more detail below. In some embodiments of any of the aforementioned embodiments, the metathesis catalyst is an organoruthenium compound, an organoosmium compound, an organotungsten compound, or an organomolybdenum compound.

The methods disclosed herein can include additional chemical and physical treatment of the resulting glyceride copolymers. For example, in some embodiments, the resulting glyceride copolymers are subjected to full or partial hydrogenation, such as diene-selective hydrogenation. Also, in some embodiments, the unspent metathesis catalyst and/or the spent metathesis catalyst residues are recovered. In some embodiments of any of the foregoing embodiments, the resulting glyceride polymers are subjected to methods that induce isomerization, such as olefin isomerization.

In another aspect, the disclosure provides methods of forming a glyceride copolymer, the methods comprising: (a) providing a reaction mixture comprising a first metathesis catalyst, unsaturated natural oil glycerides, and unsaturated alkenylized natural oil glycerides; and (b) reacting the unsaturated natural oil glycerides and unsaturated alkenylized natural oil glycerides in the presence of the first metathesis catalyst to form the glyceride copolymer.

In some embodiments, the unsaturated alkenylized natural oil glyceride is formed from the reaction of a second unsaturated natural oil glyceride with a short-chain alkene in the presence of a second metathesis catalyst. In some such embodiments, the unsaturated alkenylized natural oil glyceride has a lower molecular weight than the second unsaturated natural oil glyceride. Any suitable short-chain alkene can be used, according to the embodiments described above. In some embodiments, the short-chain alkene is a $C_{2-14}$ olefin, $C_{2-12}$ olefin, $C_{2-10}$ olefin, $C_{2-8}$ olefin, $C_{2-6}$ olefin, or a $C_{2-4}$ olefin. In some such embodiments, the short-chain alkene may comprise at least one of the following: ethylene, propylene, 1-butene, 2-butene, isobutene, 1-pentene, 2-pentene, 1-hexene, 2-hexene, 3-hexene, cyclohexene, 2-methyl-1-butene, 2-methyl-2-butene, 3-methyl-1-butene, cyclopentene, 2-methyl-1-pentene, 3-methyl-1-pentene, 4-methyl-1-pentene, 2-methyl-2-pentene, 3-methyl-2-pentene, 4-methyl-2-pentene, or 4,4-dimethyl-2-pentene. In some further such embodiments, the short-chain alkene is ethylene, propylene, 1-butene, 2-butene, or isobutene. In some embodiments, the short-chain alkene is ethylene. In some embodiments, the short-chain alkene is propylene. In some embodiments, the short-chain alkene is 1-butene. In some embodiments, the short-chain alkene is 2-butene.

As noted, it is possible to use a mixture of various linear or branched low-molecular-weight olefins in the reaction to achieve the desired metathesis product distribution. In one embodiment, a mixture of butenes (1-butene, 2-butenes, and, optionally, isobutene) may be employed as the low molecular-weight olefin, offering a low cost, commercially available feedstock instead a purified source of one particular butene. Such low cost mixed butene feedstocks are typically diluted with n-butane and/or isobutane.

The first unsaturated natural oil glyceride and the second unsaturated natural oil glyceride can be obtained from any suitable natural oil source. In some embodiments of any of the aforementioned embodiments, the first or second unsaturated natural oil glycerides are obtained from a vegetable oil, such as a seed oil. In some further embodiments, the vegetable oil is rapeseed oil, canola oil (low erucic acid rapeseed oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, or castor oil. In some embodiments, the vegetable oil is palm oil. In some embodiments, the vegetable oil is soybean oil. In some embodiments, the vegetable oil is canola oil.

The glyceride copolymers formed by the methods disclosed herein can have any suitable molecular weight. In some embodiments of any of the aforementioned embodiments, the glyceride copolymer has a weight average molecular weight ranging from 4,000 g/mol to 150,000 g/mol, or from 5,000 g/mol to 130,000 g/mol, or from 6,000 g/mol to 100,000 g/mol, or from 7,000 g/mol to 50,000 g/mol, or from 8,000 g/mol to 30,000 g/mol, or from 8,000 g/mol to 20,000 g/mol.

In some embodiments, the glyceride copolymer has a number-average molecular weight ($M_n$) from 2,000 g/mol to 150,000 g/mol, or from 3,000 g/mol to 30,000 g/mol, or from 4,000 g/mol to 20,000 g/mol.

The glyceride copolymers formed by the methods disclosed herein can have any suitable ratio of constitutional units formed from the first monomer to constitutional units formed from the second monomer. In some embodiments of any of the aforementioned embodiments, the number ratio of constitutional units formed from the first monomer to constitutional units formed from the second monomer is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. The glyceride copolymers disclosed herein can include additional constitutional units not formed from the first monomer or the second monomer.

Or, in some other embodiments of any of the foregoing embodiments, the two or more monomers are reacted in the presence of the metathesis catalyst as part of a reaction mixture, wherein the weight-to-weight ratio of the first monomer to the second monomer in the reaction mixture is no more than 10:1, or no more than 9:1, or no more than 8:1, or no more than 7:1, or no more than 6:1, or no more than 5:1, or no more than 4:1, or no more than 3:1, or no more than 2:1, or no more than 1:1. In some embodiments, the reaction mixture includes additional monomer compounds besides the first monomer and the second monomer.

Any suitable metathesis catalyst can be used as either the first metathesis catalyst or the second metathesis catalyst, as described in more detail below. In some embodiments of any of the aforementioned embodiments, the first and second metathesis catalysts are an organoruthenium compound, an organoosmium compound, an organo-tungsten compound, or an organomolybdenum compound.

The methods disclosed herein can include additional chemical and physical treatment of the resulting glyceride copolymers. For example, in some embodiments, the resulting glyceride copolymers are subjected to full or partial hydrogenation, such as diene-selective hydrogenation.

Derivation from Renewable Sources

The compounds employed in any of the aspects or embodiments disclosed herein can, in certain embodiments, be derived from renewable sources, such as from various natural oils or their derivatives. Any suitable methods can be used to make these compounds from such renewable sources.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include low erucic acid rapeseed oil (canola oil), high erucic acid rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Such natural oils, or derivatives thereof, contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain alkenes, e.g., ethylene, propylene, or 1-butene, and where the natural oil includes esters of oleic acid, an amount of 1-decene and 1-decenoid acid (or an ester thereof), among other products, are formed.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275595, and 2014/0275681, all three of which are hereby incorporated by reference as though fully set forth herein.

In certain embodiments, prior to the metathesis reaction, the natural oil and/or unsaturated polyol ester feedstock may be treated to render the natural oil more suitable for the subsequent metathesis reaction. In one embodiment, the treatment of the the natural oil and/or unsaturated polyol ester involves the removal of catalyst poisons, such as peroxides, which may potentially diminish the activity of the metathesis catalyst. Non-limiting examples of the natural oil and/or unsaturated polyol ester feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the the natural oil and/or unsaturated polyol ester feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the the natural oil and/or unsaturated polyol ester feedstock with nitrogen, wherein the nitrogen gas is pumped into the feedstock treatment vessel at a pressure of approximately 10 atm (150 psig).

In certain embodiments, the the natural oil and/or unsaturated polyol ester feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, and combinations thereof.

In certain embodiments, the natural oil and/or unsaturated polyol ester feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the the natural oil and/or unsaturated polyol ester feedstock's reactivity with the metathesis catalyst. Additional non-limiting examples of feedstock treatment are also described below when discussing the various metathesis catalysts.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions.

In some embodiments, the natural oil is winterized. Winterization refers to the process of: (1) removing waxes and other non-triglyceride constituents, (2) removing naturally occurring high-melting triglycerides, and (3) removing high-melting triglycerides formed during partial hydrogenation. Winterization may be accomplished by known methods including, for example, cooling the oil at a controlled rate in order to cause crystallization of the higher melting components that are to be removed from the oil. The crystallized high melting components are then removed from the oil by filtration resulting in winterized oil. Winterized soybean oil is commercially available from Cargill, Incorporated (Minneapolis, Minn.).

The conditions for such metathesis reactions, and the reactor design, and suitable catalysts are as described below with reference to the metathesis of the olefin esters. That discussion is incorporated by reference as though fully set forth herein.

Olefin Metathesis

In some embodiments, one or more of the unsaturated monomers can be made by metathesizing a natural oil or natural oil derivative. The terms "metathesis" or "metathesizing" can refer to a variety of different reactions, including, but not limited to, cross-metathesis, self-metathesis, ring-opening metathesis, ring-opening metathesis polymerizations ("ROMP"), ring-closing metathesis ("RCM"), and acyclic diene metathesis ("ADMET"). Any suitable metathesis reaction can be used, depending on the desired product or product mixture.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above).

In some embodiments, the unsaturated polyol ester is partially hydrogenated before being metathesized. For example, in some embodiments, the unsaturated polyol ester is partially hydrogenated to achieve an iodine value (IV) of about 120 or less before subjecting the partially hydrogenated polyol ester to metathesis.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. In some embodiments, the metathesis process may be conducted under an inert atmosphere. Similarly, in embodiments where a reagent is supplied as a gas, an inert gaseous diluent can be used in the gas stream. In such embodiments, the inert atmosphere or inert gaseous diluent typically is an inert gas, meaning that the gas does not interact with the metathesis catalyst to impede catalysis to a substantial degree. For example, non-limiting examples of inert gases include helium, neon, argon, methane, and nitrogen, used individually or with each other and other inert gases.

The rector design for the metathesis reaction can vary depending on a variety of factors, including, but not limited to, the scale of the reaction, the reaction conditions (heat, pressure, etc.), the identity of the catalyst, the identity of the materials being reacted in the reactor, and the nature of the feedstock being employed. Suitable reactors can be designed by those of skill in the art, depending on the relevant factors, and incorporated into a refining process such, such as those disclosed herein.

The metathesis reactions disclosed herein generally occur in the presence of one or more metathesis catalysts. Such methods can employ any suitable metathesis catalyst. The metathesis catalyst in this reaction may include any catalyst or catalyst system that catalyzes a metathesis reaction. Any known or future developed metathesis catalyst may be used, alone or in combination with one or more additional catalysts. Examples of metathesis catalysts and process conditions are described in US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveyda-Grubbs-type olefin metathesis catalyst and/or an entity derived therefrom. In some embodiments, the metathesis catalyst includes a second-generation Hoveyda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) Angew. Chem. Int. Ed. Engl., 2003, 42, 4592-4633; (b) Chem. Rev., 2002, 102, 145-179; and/or (c) Chem. Rev., 2009, 109, 3211-3226, each of which is incorporated by reference herein in its entirety, except that in the event of any inconsistent disclosure or definition from the present specification, the disclosure or definition herein shall be deemed to prevail.

Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru or W. These include first and second-generation Grubbs catalysts, Grubbs-Hoveyda catalysts, and the like. Suitable alkylidene catalysts

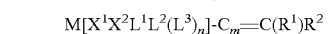

$$M[X^1X^2L^1L^2(L^3)_n]\text{-}C_m\text{=}C(R^1)R^2$$

have the general structure:
where M is a Group 8 transition metal, $L^1$, $L^2$, and $L^3$ are neutral electron donor ligands, n is 0 (such that $L^3$ may not be present) or 1, m is 0,1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first-and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^1$ are linked. Typically, a neutral oxygen or nitrogen coordinates to the metal while also being bonded to a carbon that is α-, β, or γ- with respect to the carbene carbon to provide the bidentate ligand. Examples of suitable Grubbs-Hoveyda catalysts appear in the '086 publication.

The structures below provide just a few illustrations of suitable catalysts that may be used:

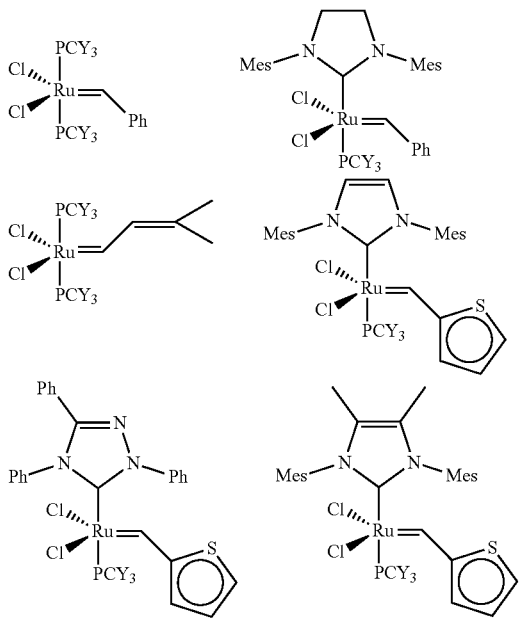

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 20 ppm, or about 2 ppm to about 15 ppm, of the metathesis catalyst per double bond of the starting composition (i.e., on a mole/mole basis) is used.

In some embodiments, the metathesis reaction is catalyzed by a system containing both a transition and a non-transition metal component. The most active and largest number of catalyst systems are derived from Group 6 and Group 8 transition metals, for example, tungsten, molybdenum, and ruthenium.

In certain embodiments, the metathesis catalyst is dissolved in a solvent prior to conducting the metathesis reaction. In certain such embodiments, the solvent chosen may be selected to be substantially inert with respect to the metathesis catalyst. For example, substantially inert solvents include, without limitation: aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In some embodiments, the solvent comprises toluene.

In other embodiments, the metathesis catalyst is not dissolved in a solvent prior to conducting the metathesis reaction. The catalyst, instead, for example, can be slurried with the natural oil or unsaturated ester, where the natural oil or unsaturated ester is in a liquid state. Under these conditions, it is possible to eliminate the solvent (e.g., toluene) from the process and eliminate downstream olefin losses when separating the solvent. In other embodiments, the metathesis catalyst may be added in solid state form (and not slurried) to the natural oil or unsaturated ester (e.g., as an auger feed).

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

The metathesis reaction temperature may, in some instances, be a rate-controlling variable where the temperature is selected to provide a desired product at an acceptable rate. In certain embodiments, the metathesis reaction temperature is greater than about −40° C., or greater than about −20° C., or greater than about 0° C., or greater than about 10° C. In certain embodiments, the metathesis reaction temperature is less than about 200° C., or less than about 150° C., or less than about 120° C. In some embodiments, the metathesis reaction temperature is between about 0° C. and about 150° C., or is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa). In certain embodiments it may be desirable to run the metathesis reactions under an atmosphere of reduced pressure. Conditions of reduced pressure or vacuum may be used to remove olefins as they are generated in a metathesis reaction, thereby driving the metathesis equilibrium towards the formation of less volatile products. In the case of a self-metathesis of a natural oil, reduced pressure can be used to remove $C_{12}$ or lighter olefins including, but not limited to, hexene, nonene, and dodecene, as well as byproducts including, but not limited to cyclohexadiene and benzene as the metathesis reaction proceeds. The removal of these species can be used as a means to drive the reaction towards the formation of diester groups and cross linked triglycerides.

In some embodiments, after metathesis has occurred, the metathesis catalyst is removed from the resulting product. One method of removing the catalyst is treatment of the metathesized product with an adsorbent bed. Representative adsorbents for use in accordance with the present teachings include but are not limited to carbon, silica, silica-alumina, alumina, clay, magnesium silicates (e.g., Magnesols), the synthetic silica adsorbent sold under the tradename TRISYL by W. R. Grace & Co., diatomaceous earth, polystyrene, macroporous (MP) resins, and the like, and combinations thereof. In one embodiment, the adsorbent is a clay bed. The clay bed will adsorb the metathesis catalyst, and after a filtration step, the metathesized product can be sent to a separation unit for further processing. The separation unit may comprise a distillation unit. In some embodiments, the distillation may be conducted, for example, by steam stripping the metathesized product. Distilling may be accomplished by sparging the mixture in a vessel, typically agitated, by contacting the mixture with a gaseous stream in a column that may contain typical distillation packing (e.g., random or structured), by vacuum distillation, or evaporating the lights in an evaporator such as a wiped film evaporator. Typically, steam stripping will be conducted at reduced pressure and at temperatures ranging from about 100° C. to 250° C. The temperature may depend, for example, on the level of vacuum used, with higher vacuum allowing for a lower temperature and allowing for a more efficient and complete separation of volatiles.

In another embodiment, the adsorbent is a water soluble phosphine reagent such as tris hydroxymethyl phosphine (THMP). THMP may be added at a rate equivalent to at least 1:1, 5:1, 10:1, 25:1, or 50:1 molar ratio relative to the catalyst. Catalyst may be separated with a water soluble phosphine through known liquid-liquid extraction mechanisms by decanting the aqueous phase from the organic phase. In other embodiments, the catalyst separation comprises washing or extracting the mixture with a polar solvent (e.g., particularly, though not exclusively, for embodiments in which the reagent is at least partially soluble in the polar solvent). Representative polar solvents for use in accordance with the present teachings include but are not limited to water, alcohols (e.g., methanol, ethanol, etc.), ethylene glycol, glycerol, DMF, multifunctional polar compounds including but not limited to polyethylene glycols and/or glymes, ionic liquids, and the like, and combinations thereof. In some embodiments, the mixture is extracted with water. In some embodiments, when a phosphite ester that is at least partially hydrolyzable (e.g., in some embodiments, a phosphite ester having a low molecular weight, including but not limited to trimethyl phosphite, triethyl phosphite, and a combination thereof) is used as a reagent, washing the mixture with water may convert the phosphite ester into a corresponding acid. In other embodiments, the metathesized product may be contacted with a reactant to deactivate or to extract the catalyst.

The metathesis reaction also results in the formation of internal olefin compounds that may be linear or cyclic. If the metathesized polyol ester is fully or partially hydrogenated, the linear and cyclic olefins would typically be fully or partially converted to the corresponding saturated linear and cyclic hydrocarbons. The linear/cyclic olefins and saturated linear/cyclic hydrocarbons may remain in the metathesized polyol ester or they may be removed or partially removed from the metathesized polyol ester using one or more known stripping techniques, including but not limited to wipe film evaporation, falling film evaporation, rotary evaporation, steam stripping, vacuum distillation, etc.

Multiple, sequential metathesis reaction steps may be employed. For example, the glyceride copolymer product may be made by reacting an unsaturated polyol ester in the presence of a metathesis catalyst to form a first glyceride copolymer product. The first glyceride copolymer product may then be reacted in a self-metathesis reaction to form another glyceride copolymer product. Alternatively, the first glyceride copolymer product may be reacted in a cross-metathesis reaction with a unsaturated polyol ester to form another glyceride copolymer product. Also in the alternative, the transesterified products, the olefins and/or esters may be further metathesized in the presence of a metathesis catalyst. Such multiple and/or sequential metathesis reactions can be performed as many times as needed, and at least one or more times, depending on the processing/compositional requirements as understood by a person skilled in the art. As used herein, a "glyceride copolymer product" may include products that have been once metathesized and/or multiply metathesized. These procedures may be used to form metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers). These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups. In certain embodiments, it may be desirable to use the glyceride copolymer products produced by cross metathesis of an unsaturated polyol ester, or blend of unsaturated polyol esters, with a $C_{2-14}$ olefin, preferably $C_{2-6}$ olefin, more preferably $C_4$ olefin, and mixtures and isomers thereof, as the reactant in a self-metathesis reaction to produce another glyceride copolymer product. Alternatively, metathesized products produced by cross metathesis of an unsaturated polyol ester, or blend of unsaturated polyol esters, with a $C_{2-14}$ olefin, preferably $C_{2-6}$ olefin, more preferably $C_4$ olefin, and mixtures and isomers thereof, can be combined with an unsaturated polyol ester, or blend of unsaturated polyol esters, and further metathesized to produce another glyceride copolymer product.

In some embodiments, the glyceride copolymer may be hydrogenated (e.g., fully or partially hydrogenated) in order to improve the stability of the oil or to modify its viscosity or other properties. Representative techniques for hydrogenating unsaturated polyol esters are known in the art and are discussed herein.

In other embodiments, the glyceride copolymers can be used as a blend with one or more fabric care benefit agents and/or fabric softening actives.

Hydrogenation:

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a glyceride copolymer, and the glyceride copolymer is then hydrogenated (e.g., partially or fully hydrogenated) to form a hydrogenated glyceride copolymer.

Hydrogenation may be conducted according to any known method for hydrogenating double bond-containing compounds such as vegetable oils. In some embodiments, the unsaturated polyol ester, natural oil or glyceride copolymer is hydrogenated in the presence of a nickel catalyst that has been chemically reduced with hydrogen to an active state. Commercial examples of supported nickel hydrogenation catalysts include those available under the trade designations "NYSOFACT", "NYSOSEL", and "NI 5248 D" (from Englehard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

In some embodiments, the hydrogenation catalyst comprising, for example, nickel, copper, palladium, platinum, molybdenum, iron, ruthenium, osmium, rhodium, or iridium. Combinations of metals may also be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt. % nickel.

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50 deg. C. to 350 deg. C., for example, about 100 deg. C. to 300 deg. C. or about 150 deg. C. to 250 deg. C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of $H_2$ gas. Typically, the $H_2$ gas pressure ranges from about 15 to 3000 psig or, for example, about 15 psig to 150 psig. As the gas pressure increases, more specialized high-pressure processing equipment may be required. Under these conditions the hydrogenation reaction begins and the temperature is allowed to increase to the desired hydrogenation temperature (e.g., about 120 deg. C. to 200 deg. C.) where it is maintained by cooling the reaction mass, for example, with cooling coils. When the desired degree of hydrogenation is reached, the reaction mass is cooled to the desired filtration temperature.

The amount of hydrogenation catalysts is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the $H_2$ gas pressure. In some embodiments, the hydrogenation catalyst is used in an amount of about 10 wt. % or less, for example, about 5 wt. % or less or about 1 wt. % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter. Representative examples of filtering aids include diatomaceous earth, silica, alumina, and carbon. Typically, the filtering aid is used in an amount of about 10 wt. % or less, for example, about 5 wt. % or less or about 1 wt. % or less. Other filtering techniques and filtering aids may also be employed to remove the used hydrogenation catalyst. In other embodiments the hydrogenation catalyst is removed using centrifugation followed by decantation of the product.

Potential Processing Aids and/or Impurities

Unsaturated polyol esters, particularly those derived or synthesized from natural sources, are known to those skilled in the art to contain a wide range of minor components and impurities. These may include tocopherols, carotenes, free fatty acids, free glycerin, sterols, glucosinolates, phospholipids, peroxides, aldehydes and other oxidation products, and the like. The impurities and reactions products present in a wide range of natural oils are described in "Bailey's Industrial Oil and Fat Products," Fifth edition, Y. H. Hui, Ed., Wiley (1996) and references cited therein; "Lipid Analysis in Oil and Fats," R. J. Hamilton, Ed., Chapman Hall (1998) and references cited therein; and "Flavor Chemistry of Fats and Oils," D. B. Min and T. H. Smouse, Ed., American Oil Chemists Society (1985) and references cited therein.

It is understood by one skilled in the art that any of these methods of making the glyceride copolymers claimed and described in this specification may result in the presence of impurities in the final glyceride copolymer and in the compositions/consumer products claimed and described in this specification as a result of the use of the glyceride copolymers. These nonlimiting examples include metathesis catalysts including metals and ligands described herein; immobilized catalyst supports including silica or alumina; oil pretreatment agents including reducing agents, cation-inorganic base compositions and adsorbents; structures which result from oil thermal pretreatment; process aids including solvents such as aromatic hydrocarbons, halogenated aromatic hydrocarbons, aliphatic solvents, and chlorinated alkanes; aliphatic olefins including hexane, nonene, dodecene, and cyclohexadiene; catalyst kill agents and/or catalyst removal agents including adsorbents such as clay, carbon, silica, silica-alumina, alumina, clay, magnesium silicates, synthetic silica, diatomaceous earth, polystyrene, macroporous (MP) resins, or water soluble phosphine reagents such as tris hydroxymethyl phosphine (THMP); polar solvents including water, alcohols (e.g., methanol, ethanol, etc.), ethylene glycol, glycerol, DMF, multifunctional polar compounds including but not limited to polyethylene glycols and/or glymes, or ionic liquids; phosphite ester hydolysis byproducts; hydrogenation catalysts, including metals and ligands described herein; immobilized hydrogenation catalyst supports including porous silica or alumina; adjuncts necessary to protect, activate and/or remove the hydrogenation catalyst; and/or water.

The glyceride copolymers claimed and described in this specification may contain the following processing aids and/or impurities:

TABLE 1

Potential Processing Aids and/or Impurities in Glyceride copolymers

| Processing aids and/or impurities | Range (ppm by weight) | Preferred Range (ppm by weight) |
|---|---|---|
| Ruthenium | 0-100 | 0-30 |
| Phosphorus | 1-2000 | 2-100 |
| Chloride | 2-200 | 3-20 |

TABLE 2

Potential Processing Aids and/or Impurities in Consumer Products Arising from Glyceride Copolymers
The following processing aids and/or impuities may be brought into or generated during storage in the compositions/consumer products claimed and described in this specification as a result of the use of the glyceride coplymers, at the levels provided in this specification:

| Processing aids and/or impurities | Range (ppm by weight) | Preferred Range (ppm by weight) | More Preferred Range (ppm by weight) |
|---|---|---|---|
| Ruthenium (ppmwt) | 0-50 | 0-10 | 0-3 |
| Phosphorus (ppmwt) | 0.5-1000 | 0.1-200 | 0.2-10 |
| Chloride (ppmwt) | 1-100 | 0.2-20 | 0.3-2 |

Test Methods

Molecular Weight Distribution

Weight-average molecular weight ($M_w$) values were determined as follows. Sample molecular weights were determined on an Agilent 1260 HPLC system equipped with autosampler, column oven, and refractive index detector. The operating system was OpenLAB CDS ChemStation Workstation (A.01.03). Data storage and analysis were performed with Cirrus GPC offline, GPC/SEC Software for ChemStation, version 3.4. Chromatographic conditions are given in Table 3. In carrying out the calculation, the results were calibrated using polystyrene reference samples having known molecular weights. Measurements of $M_w$ values vary by 5% or less. The molecular weight analyses were determined using a chloroform mobile phase.

TABLE 3

| Parameter | Conditions |
|---|---|
| Column Set | Three ResiPore columns (Agilent #1113-6300) in series with guard column (Agilent #1113-1300) Particle size: 3 μm Column dimensions: 300 × 7.5 mm |
| Mobile Phase | Chloroform |
| Flow Rate | 1 mL/min, needle wash is included |
| Column Temperature | 40° C. |
| Injection Volume | 20 μL |
| Detector | Refractive Index |
| Detector Temperature | 40° C. |

Table 4 shows the molecular weights and the retention times of the polystyrene standards.

TABLE 4

| Standard Number | Average Reported MW | Retention Time (min) |
|---|---|---|
| 1 | 150,000 | 19.11 |
| 2 | 100,000 | 19.63 |
| 3 | 70,000 | 20.43 |
| 4 | 50,000 | 20.79 |
| 5 | 30,000 | 21.76 |
| 6 | 9,000 | 23.27 |
| 7 | 5,000 | 23.86 |
| 8 | 1,000 | 27.20 |
| 9 | 500 | 28.48 |

Iodine Value

Another aspect of the invention provides a method to measure the iodine value of the glyceride copolymer. The iodine value is determined using AOCS Official Method Cd 1-25 with the following modifications: carbon tetrachloride solvent is replaced with chloroform (25 ml), an accuracy check sample (oleic acid 99%, Sigma-Aldrich; IV=89.86±2.00 cg/g) is added to the sample set, and the reported IV is corrected for minor contribution from olefins identified when determining the free hydrocarbon content of the glyceride copolymer.

Free Hydrocarbon Content

Another aspect of this invention provides a method to determine both the free hydrocarbon content of the glyceride copolymer. The method combines gas chromatography/mass spectroscopy (GC/MS) to confirm identity of the free hydrocarbon homologs and gas chromatography with flame ionization detection (GC/FID) to quantify the free hydrocarbon present in the glyceride copolymer.

Sample Prep: The sample to be analyzed was typically trans-esterified by diluting (e.g. 400:1) in methanolic KOH (e.g. 0.1N) and heating in a closed container until the reaction was complete (i.e. 90° C. for 30 min.) then cooled to room temperature. The sample solution could then be treated with 15% boron tri-fluoride in methanol and again heated in a closed vessel until the reaction was complete (i.e. at 60° C. for 30 min.) both to acidify (methyl orange-red) and to methylate any free acid present in the sample. After allowing to cool to room temperature, the reaction was quenched by addition of saturated NaCl in water. An organic extraction solvent such as cyclohexane containing a known level internal standard (e.g. 150 ppm dimethyl adipate) was then added to the vial and mixed well. After the layers separated, a portion of the organic phase was transferred to a vial suitable for injection to the gas chromatograph. This sample extraction solution was analyzed by GC/MS to confirm identification of peaks matching hydrocarbon retention times by comparing to reference spectra and then by GC/FID to calculate concentration of hydrocarbons, fatty acid, and fatty diacid by comparison to standard FID response factors.

A hydrocarbon standard of known concentrations, such as 50 ppm each, of typically observed hydrocarbon compounds (i.e. 1-dodecene, 1-tridecene, 1-tetradecene, 1-pentadecene, 1-hexadecene, 1-heptadecene, 1-octadecene, dodecane, tridecane, tetradecane, pentadecane, hexadecane, heptadecane and octadecane) was prepared by dilution in the same solvent containing internal standard as was used to extract the sample reaction mixture. This hydrocarbon standard was analyzed by GC/MS to generate retention times and reference spectra and then by GC/FID to generate retention times and response factors.

GC/MS: An Agilent 7890 GC equipped with a split/splitless injection port coupled with a Waters QuattroMicroGC mass spectrometer set up in EI+ ionization mode was used to carry out qualitative identification of peaks observed. A non-polar DB1-HT column (15 m×0.25 mm×0.1 um df) was installed with 1.4 mL/min helium carrier gas. In separate runs, 1 uL of the hydrocarbon standard and the sample extract solution were injected to a 300° C. injection port with a split ratio of 25:1. The oven was held at 40° C. for 1 minute then ramped 15 C.°/minute to a final temperature of 325° C. which was held for 10 minutes resulting in a total run time of 30 minutes. The transfer line was kept at 330° C. and the temperature of the EI source was 230° C. The ionization energy was set at 70 eV and the scan range was 35-550 m/z.

GC/FID: An Agilent 7890 GC equipped with a split/splitless injection port and a flame ionization detector was used for quantitative analyses. A non-polar DB1-HT column (5 m×0.25 mm×0.1 um df) was installed with 1.4 mL/min helium carrier gas. In separate runs, 1 uL of the hydrocarbon standard and the sample extract solution was injected to a 330° C. injection port with a split ratio of 100:1. The oven was held at 40° C. for 0.5 minutes then ramped at 40 C.°/minute to a final temperature of 380° C. which was held for 3 minutes resulting in a total run time of 12 minutes. The FID was kept at 380° C. with 40 mL/minute hydrogen gas flow and 450 mL/min air flow. Make up gas was helium at 25 mL/min. The hydrocarbon standard was used to create calibration tables in the Chemstation Data Analysis software including known concentrations to generate response factors. These response factors were applied to the corresponding peaks in the sample chromatogram to calculate total amount of free hydrocarbon found in each sample.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Non-limiting examples of product formulations disclosed in the present specification are summarized below.

Example 1—Reaction with Butenylyzed Canola Oil (BCO): Effect of BCO Content

The experimental apparatus consisted of a three-necked round-bottom flask equipped with a magnetic stir bar, a septum cap, and an outlet to a vacuum system. External heating was provided via a silicone oil bath. The septum was used to add metathesis catalyst and withdraw samples. The vacuum system consisted of a TEFLON diaphragm pump and a pressure controller.

Butenylyzed canola oil (BCO) was made by cross-metathesizing canola oil (Wesson) with 1-butene (1 mol of 1-butene per mol of C=C double bonds in the oil) according to the methods described in U.S. Pat. No. 8,957,268. The BCO was mixed with canola oil (Wesson) and charged to a 500-mL round-bottom flask. The oil mixture was purged with nitrogen gas (Airgas, UHP) for about 15 minutes. The reaction flask was heated to about 70° C. and evacuated to the desired pressure (see below: 200 or 450 torr absolute.) A toluene (Sigma-Aldrich, anhydrous 99.8%) solution of C827 metathesis catalyst (10 mg/mL; Materia, Inc., Pasadena, Calif., USA) was added to the oil mixture to achieve a catalyst level of 100 ppmwt. The reaction was held at 70° C. while maintaining a dynamic vacuum at the desired pressure for 2 hours. A small sample of the reaction mixture was removed by syringe, quenched with ethyl vinyl ether (Sigma-Aldrich), and analyzed by GPC to determine the weight-average molecular weight ($M_w$) of the resulting glyceride oligomers.

Table 5 shows the resulting weight average $M_w$ for 13 different reactions, where the percentage of BCO was increased. The percentage of BCO reported is a weight percentage of BCO relative to the total weight of oil (BCO and canola oil combined). The weight average molecular weights are reported in units of g/mol.

TABLE 5

| Percentage BCO (wt %) | $M_w$ 450 Torr (absolute) Experiments | $M_w$ 200 Torr (absolute) Experiments |
|---|---|---|
| 0 | 11,700 | 12,300 |
| 10 | 12,800 | 13,100 |

TABLE 5-continued

| Percentage BCO (wt %) | $M_w$ 450 Torr (absolute) Experiments | $M_w$ 200 Torr (absolute) Experiments |
|---|---|---|
| 30 | 13,600 | 14,800 |
| 50 | 14,400 | 18,000 |
| 70 | 14,100 | 22,500 |
| 90 | 14,500 | — |
| 100 | 25,900 | 56,600 |

Example 2—Reaction with Butenylyzed Canola Oil (BCO): Effect of Reaction Time

Using the same apparatus and procedures as those described in Example 1, 50 wt %/50 wt % mixtures of BCO and canola oil were reacted for four hours while maintaining a dynamic vacuum at either 200 or 450 torr (absolute) with samples being taken hourly. Table 6 shows the weight averaged molecular weight ($M_w$) over time. The molecular weight ($M_w$) is reported in units of g/mol.

TABLE 6

| Time (hr) | $M_w$ 450 Torr (absolute) Experiments | $M_w$ 200 Torr (absolute) Experiments |
|---|---|---|
| 1 | 13,600 | 16,100 |
| 2 | 13,600 | 18,000 |
| 3 | 13,100 | 19,000 |
| 4 | 13,000 | 20,000 |

Example 3—Cross-Metathesis of Canola Oil with Butenylyzed Palm Oil (BPO): Effect of Feedstock Composition Using the same apparatus and procedures as those described in Example 1, mixtures of BPO (Wilmar) and canola oil were reacted for two hours. Table 7 shows the molecular weight ($M_w$) after two hours. The molecular weight ($M_w$) is reported in units of g/mol.

TABLE 7

| Percentage BPO (wt %) | $M_w$ 200 Torr (absolute) Experiment |
|---|---|
| 15 | 9,400 |
| 25 | 8,100 |
| 35 | 5,900 |

Example 4—Canola Oil Self-Metathesis (Comparative Example)

Using the same apparatus (except that a two-stage rotary vane pump was used for experiments run under dynamic vacuums of less than 10 torr absolute and procedure described in Example 1, canola oil was reacted for two hours. Table 8 shows the molecular weight ($M_w$) after two hours. The molecular weight ($M_w$) is reported in units of g/mol.

TABLE 8

| Absolute Pressure (Torr) | 100-g Scale ($M_w$) | 1-kg Scale ($M_w$) |
|---|---|---|
| 450 | 11,700 | — |
| 200 | 12,300 | — |
| 75 | 12,600 | — |
| 8 | 14,500 | 13,600 |
| 3.2 | — | 15,100 |
| 2.5 | — | 15,900 |

A portion (473 g) of the product from the 1 kg experiment run at 2.5 torr was diluted with heptane (BDH, laboratory reagent, 500 mL). Magnesol-600-R (Dallas Group of Am., 10 g) was added and the resulting mixture was stirred under nitrogen at ambient temperature for 30 minutes. The Magnesol-600-R was removed by vacuum filtration. A fresh charge of Magnesol-600-R (10 g) was added and the resulting mixture was stirred under nitrogen at ambient temperature for 30 minutes. Heptane was removed by rotovap. Olefins were removed by vacuum distillation in a 1 L three-neck round-bottom equipped with a short-path distillation head; a condenser chilled to 5° C.; a 20 mL round bottom flask chiller with dry-ice/isopropanol; a magnetic stir bar; and thermometers to measure liquid temperature and vapor temperature. Heating was supplied through a resistive heating mantle. Vacuum was supplied by a two-stage rotary vane vacuum pump. The bulk of olefinic material was removed by gradually increasing the heat input. A very small nitrogen purge was maintained on the system for the initial part of the distillation. The final pressure was about 0.1 torr absolute and the final liquid temperature was 192° C. The olefin content was less than 1% by mass. A sample of the final product was trans-esterified and analyzed by GC to determine the Fatty Acid Residues as described above. See Table 9 (below).

Example 5—Cross-Metathesis of Canola with Butenylyzed Canola Oil (BCO) on One-Kilogram Scale with Catalyst Removal and Olefin Stripping Using a similar metathesis procedure and apparatus to the one described in Example 1, a 1 kg mixture of BCO and canola oil (50 wt %/50 wt %) was reacted for two hours. Catalyst removal was accomplished by THMP treatment. THMP treatments consisted of adding 1 M tris(hydroxymethyl)phosphine (THMP, 1.0 M, 50 mol THMP/mol C827) in water, stirring at ambient temperature for 2 hours, and then washing the product with water (2×100 mL) in a separatory funnel. Olefin by-products and traces of residual water were removed from the product by the same procedure and distillation apparatus as described in Example 4 except that no nitrogen purge was used. The final pressure was about 0.2 torr absolute and the final liquid temperature was 195° C. The olefin content was less than 1% by mass and the $M_w$ of the glyceride oligomer was 16,700 g/mol. A sample of the final product was trans-esterified and analyzed by GC to determine the Fatty Acid Residues as described above. See Table 9 (below).

Example 6—Cross-Metathesis of Soybean Oil with Butenylyzed Soybean Oil (BSO) on a Two-Kilogram Scale with Catalyst Removal and Olefin Stripping Using the same procedure and an apparatus similar to that described in Example 1 except that a 3 L flask was used in place of the 500 mL flask, a 1 kg, 50/50 wt % mixture of butenylyzed soybean oil and soybean oil (Costco) was reacted for about four hours using 100 ppm wt C827 catalyst. An additional 40 ppm of catalyst was added and after about two more hours the reaction was quenched with ethyl vinyl ether. Olefin by-products and traces of residual water were removed from a 265 g sample of the product by a similar distillation procedure and apparatus as described in Example 5. The final pressure was about 0.1 torr absolute and the final liquid temperature was 195° C. The olefin content was less than 1% by mass. A sample of the final product was trans-esterified and analyzed by GC to determine the Fatty Acid Residues as described above. See Table 9 (below).

Example 7—Cross-Metathesis of Canola Oil with Butenylyzed Canola Oil (BCO) on a Twelve-Kilogram Scale with Catalyst Removal and Olefin Stripping This example was conducted in a 5 gallon Stainless Steel Reactor (Parr) equipped with an impeller, a port for air-free catalyst addition, and a Strahman valve for sampling. The reactor system was completely purged with nitrogen before beginning.

The BCO (6.16 kg) was produced by a procedure similar to that used in Example 1 and mixed with canola oil (6.12 kg) and charged to the reactor. The oil mixture was stirred at 200 rpm while purging with nitrogen gas for about 30 minutes through a dip tube at a rate of 0.5 SCFM. The reactor was evacuated to 200 torr (absolute) and heated to 70° C. The C827 metathesis catalyst (1.0 g, Materia, Inc., Pasadena, Calif., USA) was suspended in canola oil (50 mL) and added to the oil mixture. The reaction was maintained at 70° C. and at 200 torr for four hours. An additional charge of C827 catalyst (0.25 g) suspended in canola oil (50 mL) was added to the reaction. After an additional two hours, the reactor was back filled with nitrogen.

Catalyst removal was conducted in a 5 gallon jacketed glass reactor equipped with an agitator, a bottom drain valve, and ports for adding reagents. A 0.12 M aqueous solution of THMP (0.31 kg) was charged to the glass reactor and pre-heated to about 90° C. The crude metathesis reaction product, still at 70° C., was transferred to the glass reactor and the mixture was stirred (150 rpm) at about 80-90° C. for 20 minutes. The following wash procedure was done twice. Deionized water (1.9 kg at 60° C.) was added to the reactor which was heated to 80-90° C. and the resulting mixture was stirred (100 rpm) for 20 minutes. The stirrer was stopped and the reactor contents were allowed to settle for 16 hours at a constant temperature of 80-90° C. The bottom aqueous layer was carefully drained off. Following the second wash, the washed product was cooled and then drained to a container.

The washed product was divided into two portions to remove olefins and residual water, which was done using a similar distillation procedure and apparatus as described in Example 5. The final distillation pressure was about 0.1 torr absolute and the final liquid temperature was about 190° C. Following distillation, the two portions were recombined. A small sample of the recombined product was trans-esterified and analyzed by GC to determine the Fatty Acid Residues as described above. See Table 9 (below).

The fatty acid residues in the final glyceride oligomer products produced in examples 4, 5, 6, and 7 were analyzed by the method described above after olefins were vacuum distilled to below 1% by weight. The $C_{10-14}$ unsaturated fatty acid esters, $C_{10-13}$ unsaturated fatty acid esters, and $C_{1-11}$ unsaturated fatty acid esters were calculated and are reported in Table 10.

TABLE 9

| Fatty Acid Methyl Ester Component | Example 4 Product (wt %) | Example 5 Product (wt %) | Example 6 Product (wt %) | Example 7 Product (wt %) |
|---|---|---|---|---|
| C10:1 | — | 6.72 | 2.97 | 4.58 |
| C12:1 | 1.74 | 7.33 | 4.77 | 6.25 |
| C13:2 | — | 1.33 | 0.71 | 0.72 |
| C15:1 | 8.53 | 5.05 | 12.21 | 5.05 |
| C16:0 | 5.89 | 6.12 | 14.69 | 5.65 |
| C16:1 | 1.97 | 1.08 | 0.43 | 1.06 |
| C18:0 | 2.53 | 2.65 | 6.05 | 2.58 |
| C18:1 | 35.87 | 19.52 | 6.31 | 19.80 |
| C18:2 | 0.80 | 1.33 | 3.46 | 0.89 |
| C18:3 | 0.64 | 0.39 | 0.42 | 0.27 |
| C20:0 | 1.30 | 0.85 | 0.48 | 0.90 |
| C20:1 | 2.10 | 1.08 | 0.29 | 1.15 |
| C21:2 | 2.82 | 3.59 | 1.76 | 3.61 |
| C22:0 | 0.53 | 0.56 | 0.08 | 0.60 |
| C18:1 diester | 26.80 | 29.10 | 21.84 | 29.85 |
| C20:1 diester | 3.09 | 3.11 | 1.02 | 3.08 |
| C21:2 diester | 1.00 | 5.10 | 6.40 | 4.95 |

TABLE 10

| Unsaturated Fatty Acid Ester Component | Example 4 Product (wt %) | Example 5 Product (wt %) | Example 6 Product (wt %) | Example 7 Product (wt %) |
|---|---|---|---|---|
| $C_{10-14}$ unsaturated fatty acid esters | 1.74 | 15.38 | 8.45 | 11.55 |
| $C_{10-13}$ unsaturated fatty acid esters | 1.74 | 15.38 | 8.45 | 11.55 |
| $C_{10-11}$ unsaturated fatty acid esters | — | 6.72 | 2.97 | 4.58 |

Example 8—Diene-Selective Hydrogenation of Crude Glyceride Polymer

In a 600 mL Parr reactor, 170 g of crude metathesis product from Example 6, 170 g of n-decane (Sigma-Aldrich, anhydrous, ≥99%), and 0.60 g PRICAT 9908 (Johnson Matthey Catalysts); saturated triglyceride wax removed before reaction via a toluene wash) were purged with $N_2$, then $H_2$, for 15 minutes each, then reacted at 160° C. under 100 psig $H_2$ (Airgas, UHP) with 1000 rpm stirring with a gas dispersion impeller. The $H_2$ pressure was monitored and the reactor was refilled to 100 psig when it decreased to about 70 psig. After six hours, the reaction was cooled below 50° C. and the hydrogen was displaced by nitrogen gas. The reaction mixture was vacuum filtered through diatomaceous earth to remove the catalyst solids. Olefin by-products and n-decane were removed from the product by a similar distillation procedure and apparatus as described in Example 5. The final distillation pressure was about 0.1 torr absolute and the final liquid temperature was 195° C. The olefin content was less than 1% by mass. A sample of the final product was trans-esterified with methanol and analyzed by GC. The level of polyunsaturated C18 fatty acid methyl esters (C18:2 plus C18:3) were reduced from 3.88% in the starting material to 1.13% and the C21:2 diester was reduced from 6.40% in the starting material to 3.72%. Examples 9 through 21 are exemplary topsheet lotions.

Example 9

| | % |
|---|---|
| Glyceride Copolymer of Examples 1-8 | 71% |
| Beeswax | 18% |
| Isostearyl Isostearate | 11% |
| | 100% |

Example 10

| | % |
|---|---|
| Glyceride Copolymer of Examples 1-8 | 63% |
| Cetyl Alcohol | 22% |
| Jojoba Oil | 15% |
| | 100% |

Example 11

| | % |
|---|---|
| Glyceride Copolymer of Examples 1-8 | 52% |
| ZnO | 7% |
| Ester Wax | 33% |
| Innotec Wetting Agent | 3% |
| Olive Oil | 5% |
| | 100% |

Example 12

| | % |
|---|---|
| Glyceride Copolymer of Examples 1-8 | 62% |
| Ozokerite Wax | 29% |
| Sunflower Oil | 9% |
| | 100% |

Example 13

| | % |
|---|---|
| Metathesized Glyceride Copolymer of Examples 1-8 | 59% |
| Kraton G-1650 | 12% |
| ZnO | 6% |
| Ester Wax | 7% |
| C12-C15 Alkyl Benzoate | |
| Innotec Wetting Agent | 3% |
| Petrolatum | 9% |
| | 100% |

Example 14

| | % |
|---|---|
| Glyceride Copolymer of Examples 1-8 | 44% |
| Candillila Wax | 15% |
| Lanolin | 7% |
| Stearyl Alcohol | 25% |
| Microcrystalline Wax | 9% |
| | 100% |

Example 15

| | % |
|---|---|
| Glyceride Copolymer of Examples 1-8 | 50% |
| Beeswax (420 ORG from Strahl & Pitsch) | 23% |
| Octyldodecylneopentanoate (Elefac I-205 from Alzo) | 6% |
| Di(C12-C15)Alkyl Fumarate (Marrix SF from Alzo) | 12% |
| Zinc Oxide (Zoco 112 USP from Zochem Inc.) | 9% |
| | 100% |

Example 16

| | % |
|---|---|
| Glyceride Copolymer of Examples 1-8 | 51% |
| Cetostearyl Alcohol (TA-1618 from P&G Chemicals) | 11% |
| Carnauba Wax (#63P from Strahl & Pitsch Inc.) | 19% |
| Jojoba Butter (#SP560 from Strahl & Pitsch Inc.) | 9% |
| Neopentyl glycol diethylhexanoate and neopentyl glycol diisostearate (Minno 21 from Alzo) | 4% |
| Zinc Oxide (Zoco 112 USP from Zochem Inc.) | 6% |
| | 100% |

Example 17

| | % |
|---|---|
| Glyceride Copolymer of Examples 1-8 | 42% |
| Petrolatum (Perfecta from Sonneborn) | 11% |
| Arachidyl Behenate (Waxenol 822 from Alzo) | 11% |
| Candellila Wax Powder (#75P from Strahl & Pitsch) | 17% |
| Methylheptyl Isostearate (Beantree from Alzo) | 6% |
| Octyldodecyl Neopentanoate (Elefac I-205 from Alzo) | 5% |
| Zinc Oxide (Zoco 112 USP from Zochem Inc.) | 8% |
| | 100% |

Example 18

| | % |
|---|---|
| Glyceride Copolymer of Examples 1-8 | 28% |
| Petrolatum (Perfecta from Sonneborn) | 19% |
| Microcrystalline Wax (Multiwax W-835 from Sonneborn) | 15% |
| Ozokerite Wax (#1025 from Strahl & Pitsch) | 13% |
| Mineral Oil (Carnation Mineral Oil from Sonneborn) | 9% |
| Neopentyl glycol diethylhexanoate and neopentyl glycol diisostearate (Minno 21 from Alzo) | 5% |
| Zinc Oxide (Zoco 112 USP from Zochem Inc.) | 11% |
| | 100% |

Example 19

| | % |
|---|---|
| Glyceride Copolymer of Examples 1-8 | 45% |
| White Petrolatum (SnowWhite from Sonneborn) | 18% |
| Di-C12-15 Alkyl Fumarate (Marrix SF from Alzo) | 5% |
| Arachidyl Behenatie (Waxenol 822 from Alzo) | 9% |
| Cetostearyl Fatty Alcohol (TA-1618 from Procter&Gamble Chemicals) | 11% |
| Octyldodecyl Neopentanoate (Elefac I-205 from Alzo) | 4% |
| Zinc Oxide (Zoco 112 USP from Zochem Inc.) | 8% |
| | 100% |

Example 20

| | % |
|---|---|
| Glyceride Copolymer of Examples 1-8 | 33% |
| Di-C12-15 Alkyl Fumarate (Marrix SF from Alzo) | 15% |
| Ozokerite Wax (#1025 from Strahl & Pitsch) | 24% |
| Cetearyl Methicone (SF1632 from Momentive) | 19% |

-continued

| | % |
|---|---|
| Caprylyl Isostearate (Beantree from Alzo) | 9% |
| | 100% |

Example 21

| | % |
|---|---|
| Glyceride Copolymer of Examples 1-8 | 30% |
| Di-C12-15 Alkyl Fumarate (Marrix SF from Alzo) | 13% |
| Ozokerite Wax (#1025 from Strahl & Pitsch) | 22% |
| Petrolatum (G-1958 from Sonneborn Inc.) | 14% |
| Mineral Oil (Lilac from Sonneborn Inc.) | 12% |
| Vegetable Oil (SonneNatural H-203 from Sonneborn Inc.) | 9% |
| | 100% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a composition, said composition comprising
A) a glyceride copolymer having formula (I):

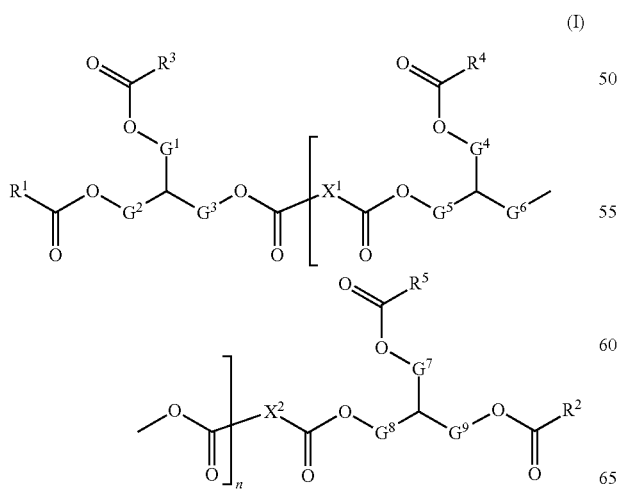

wherein:
each $R^1$, $R^2$, $R^3$, $R^4$, and $R^5$ in the glyceride copolymer is independently selected from the group consisting of an oligomeric glyceride moiety, a $C_{1-24}$ alkyl, a substituted $C_{1-24}$ alkyl wherein the substituent is one or more —OH moieties, a $C_{2-24}$ alkenyl, or a substituted $C_{2-24}$ alkenyl wherein the substituent is one or more —OH moieties; and/or wherein each of the following combinations of moieties may each independently be covalently linked:
$R^1$ and $R^3$,
$R^2$ and $R^5$,
$R^1$ and an adjacent $R^4$,
$R^2$ and an adjacent $R^4$,
$R^3$ and an adjacent $R^4$,
$R^5$ and an adjacent $R^4$, or
any two adjacent $R^4$
such that the covalently linked moieties form an alkenylene moiety;
each $X^1$ and $X^2$ in said glyceride copolymer is independently selected from the group consisting of a $C_{1-32}$ alkylene, a substituted $C_{1-32}$ alkylene wherein the substituent is one or more —OH moieties, a $C_{2-32}$ alkenylene or a substituted $C_{2-32}$ alkenylene wherein the substituent is one or more —OH moieties;
two of $G^1$, $G^2$, and $G^3$ are —$CH_2$—, and one of $G^2$, and $G^3$ is a direct bond;
for each individual repeat unit in the repeat unit having index n, two of $G^4$, $G^5$, and $G^6$ are —$CH_2$—, and one of $G^4$, $G^5$, and $G^6$ is a direct bond, and the values $G^4$, $G^5$, and $G^6$ for each individual repeat unit are independently selected from the values of $G^4$, $G^5$, and $G^6$ in other repeating units;
two of $G^7$, $G^8$, and $G^9$ are —$CH_2$—, and one of $G^7$, $G^8$, and $G^9$ is a direct bond;
n is an integer from 3 to 250;
with the proviso for each of said glyceride copolymers at least one of $R^1$, $R^2$, $R^3$, and $R^5$, and/or at least one $R^4$ in one individual repeat unit of said repeat unit having index n, is selected from the group consisting of: 8-nonenyl; 8-decenyl; 8-undecenyl; 8-dodecenyl; 8,11-dodecadienyl; 8,11-tridecadienyl; 8,11-tetradecadienyl; 8,11-pentadecadienyl; 8,11,14-pentadecatrienyl; 8,11,14-hexadecatrienyl; 8,11,14-octadecatrienyl; 9-methyl-8-decenyl; 9-methyl-8-undecenyl; 10-methyl-8-undecenyl; 12-methyl-8,11-tridecadienyl; 12-methyl-8,11-tetradecadienyl; 13-methyl-8,11-tetradecadienyl; 15-methyl-8,11,14-hexadecatrienyl; 15-methyl-8,11,14-heptadecatrienyl; 16-methyl-8,11,14-heptadecatrienyl; 12-tridecenyl; 12-tetradecenyl; 12-pentadecenyl; 12-hexadecenyl; 13-methyl-12-tetradecenyl; 13-methyl-12-pentadecenyl; and 14-methyl-12-pentadecenyl; and
mixtures thereof; and
B) optionally a material selected from the group consisting of emollients, structuring agents, viscosity enhancers, surfactants, skin care ingredients, vitamins, moisturizers, perfumes, aesthetic ingredients, enzyme inhibitors, and combinations thereof.

* * * * *